US008940277B2

(12) United States Patent
Wang et al.

(10) Patent No.: US 8,940,277 B2
(45) Date of Patent: Jan. 27, 2015

(54) INTRACELLULAR MICROBUBBLE FOR IMAGING AN ANATOMICAL SITE

(75) Inventors: Jianjun Wang, Glenshaw, PA (US); Flordeliza Villanueva, Pittsburgh, PA (US); Xucai Chen, Glenshaw, PA (US); Andrew Fisher, Pittsburgh, PA (US); William Richard Wagner, Wexford, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 385 days.

(21) Appl. No.: 12/613,400

(22) Filed: Nov. 5, 2009

(65) Prior Publication Data

US 2010/0158815 A1 Jun. 24, 2010

Related U.S. Application Data

(60) Provisional application No. 61/111,971, filed on Nov. 6, 2008.

(51) Int. Cl.
*A61B 8/00* (2006.01)
*A61B 8/08* (2006.01)
*A61K 49/22* (2006.01)

(52) U.S. Cl.
CPC ............... *A61K 49/222* (2013.01); *A61B 8/481* (2013.01)
USPC .......................................... 424/9.52; 424/9.1

(58) Field of Classification Search
None
See application file for complete search history.

(56) References Cited

U.S. PATENT DOCUMENTS

| 5,709,209 A | 1/1998 | Friemel et al. ................. 600/447 |
| 6,730,036 B2 | 5/2004 | Rafter et al. ................... 600/458 |
| 6,919,068 B2 | 7/2005 | Short ........................... 424/9.52 |
| 2001/0012522 A1* | 8/2001 | Ottoboni et al. .............. 424/501 |
| 2005/0283098 A1 | 12/2005 | Conston et al. .................... 601/2 |
| 2008/0200862 A1 | 8/2008 | Unger et al. ..................... 604/22 |
| 2009/0081130 A1 | 3/2009 | Ottoboni et al. ............. 424/9.52 |
| 2009/0098168 A1* | 4/2009 | Hettiarachchi et al. ....... 424/400 |
| 2011/0044903 A1* | 2/2011 | Borrelli .......................... 424/9.1 |

FOREIGN PATENT DOCUMENTS

WO WO 2006062664 A2 * 6/2006

OTHER PUBLICATIONS

Caplan, Review: mesenchymal stem cells: cell-based reconstructive therapy in orthopedics, Tissue Eng. 11(7-8):1198-211, 2005.*
Dayton et al., Application of ultrasound to selectively localize nanodroplets for targeted imaging and therapy, Mol Imaging. 5(3):160-74, 2006.*
Weller et al. "Modulating Targeted Adhesion of an Ultrasound Contrast Agent to Dysfunctional Endothelium." Annals of Biomedical Engineering, 2002; 30:1012-1019.*
Villanueva et al. "Myocardial Ischemic Memory Imaging With Molecular Echocardiography." Circulation. 2007;115:345-352.*
Song et al. "Ultrasound-mediated microbubble destruction enhances the efficacy of bone marrow mesenchymal stem cell transplantation and cardiac function." Clinical and Experimental Pharmacology and Physiology, Mar. 2009, online Sep. 10, 2008; vol. 36, Issue 3: 267-271.*
Song et al."Ultrasound-mediated microbubble destruction enhances the efficacy of bone marrow mesenchymal stem cell transplantation and cardiac function." Date Verification Sheet, accessed May 31, 2013.*
Foreign Document, WO2006062664 A2.*
Intercellular. Dictionary.com. Collins English Dictionary—Complete & Unabridged 10th Edition. HarperCollins Publishers. http://dictionary.reference.com/browse/intercellular (accessed: May 27, 2014).*
Intracellular. Dictionary.com. Collins English Dictionary—Complete & Unabridged 10th Edition. HarperCollins Publishers. http://dictionary.reference.com/browse/intercellular (accessed: May 27, 2014).*
Aicher, A. et al. (2003) "Assessment of the Tissue Distribution of Transplanted Human Endothelial Progenitor Cells by Radioactive Labeling", *Circulation 107*(16), 2134-2139.
Amado, L. C. et al. (2005) "Cardiac repair with intramyocardial injection of allogeneic mesenchymal stem cells after myocardial infarction", *Proc. Natl. Acad. Sci. U. S. A. 102*(32), 11474-11479.
Barbash, I. M. et al. (2003) "Systemic Delivery of Bone Marrow-Derived Mesenchymal Stem Cells to the Infarcted Myocardium", *Circulation 108*(7), 863-868.
Bartunek, J. et al. (2005) "Intracoronary Injection of CD133-Positive Enriched Bone Marrow Progenitor Cells Promotes Cardiac Recovery After Recent Myocardial Infarction", *Circulation 112*(9 suppl), I-178-I-183.
Beeres, S. L. M. A. et al. (2007) "Role of Imaging in Cardiac Stem Cell Therapy", *J. Am. Coll. Cardiol. 49*(11), 1137-1148.
Boyle, A. J. et al. (2006) "Stem Cell Therapy for Cardiac Repair", *Circulation 114*(4), 339-352.
Britten, M. B. et al. (2003) "Infarct Remodeling After Intracoronary Progenitor Cell Treatment in Patients With Acute Myocardial Infarction (TOPCARE-AMI)", *Circulation 108*(18), 2212-2218.

(Continued)

*Primary Examiner* — Thaian N Ton
*Assistant Examiner* — Titilayo Moloye
(74) *Attorney, Agent, or Firm* — Medlen & Carroll, LLP

(57) ABSTRACT

This invention addresses the clinical problem of how to optimize biological cell based therapies, such as stem cell therapy. Currently, cell therapies administered by intravenous, intra-arterial, and/or direct tissue injection are limited by the lack of clinically available imaging methods to detect the in vivo fate of the administered cells. There are many efforts underway to develop imaging strategies for stem cells in vivo, including radionuclide and MRI-based approaches. However, these approaches are limited by potential safety issues (e.g. radioactive exposure of stem cells, toxicity of iron particles used for MRI) and difficulty in serial tracking due to complex instrumentation and/or the requirement for repetitive radiation exposure.

7 Claims, 43 Drawing Sheets

(56) References Cited

OTHER PUBLICATIONS

Bulte, J. W. M. et al. (2002) "Monitoring stem cell therapy in vivo using magnetodendrimers as a new class of cellular MR contrast agents", *Acad. Radiol.* 9(Supplement 2), S332-335.
Bulte, J. W. M. et al. (2001) "Magnetodendrimers allow endosomal magnetic labeling and in vivo tracking of stem cells", *Nat. Biotechnol.* 19, 1141-1147.
Cao, Y.-A. et al. (2004) "Shifting foci of hematopoiesis during reconstitution from single stem cells", *Proc. Natl. Acad. Sci. U. S. A.* 101(1), 221-226.
Chin, B. B. et al. (2003) "$^{111}$In oxine labelled mesenchymal stem cell SPECT after intravenous administration in myocardial infarction", *Nucl. Med. Commun.* 24(11), 1149-1154.
Chithrani, B. D. et al. (2006) "Determining the Size and Shape Dependence of Gold Nanoparticle Uptake into Mammalian Cells", *Nano Lett.* 6(4), 662-668.
Christiansen, J. P. et al. (2002) "Noninvasive Imaging of Myocardial Reperfusion Injury Using Leukocyte-Targeted Contrast Echocardiography", *Circulation* 105(15), 1764-1767.
Daldrup-Link, H. E. et al. (2003) "Targeting of Hematopoietic Progenitor Cells with MR Contrast Agents", *Radiology* 228(3), 760-767.
De Jong, N. et al. (2002) "Basic Acoustic Properties of Microbubbles", *Echocardiography* 19(3), 229-240.
de Vries, I. J. M. et al. (2005) "Magnetic resonance tracking of dendritic cells in melanoma patients for monitoring of cellular therapy", *Nat. Biotechnol.* 23(11), 1407-1413.
Desai, M. P. et al. (1997) "The Mechanism of Uptake of Biodegradable Microparticles in Caco-2 Cells Is Size Dependent", *Pharm. Res.* 14(11), 1568-1573.
Ferguson, B. et al. (2002) "Towards functional 3D T-ray imaging", *Phys. Med. Biol.* 47(21), 3735-3742.
Frangioni, J. V. (2003) "In vivo near-infrared fluorescence imaging", *Curr. Opin. Chem. Biol.* 7(5), 626-634.
Frangioni, J. V. and Hajjar, R. J. (2004) "In Vivo Tracking of Stem Cells for Clinical Trials in Cardiovascular Disease", *Circulation* 110(21), 3378-3383.
Frank, J. A. et al. (2003) "Clinically Applicable Labeling of Mammalian and Stem Cells by Combining Superparamagnetic Iron Oxides and Transfection Agents", *Radiology* 228(2), 480-487.
Freyman, T. et al. (2006) "A quantitative, randomized study evaluating three methods of mesenchymal stem cell delivery following myocardial infarction", *Eur. Heart J.* 27(9), 1114-1122.
Fuchs, S. et al. (2006) "Safety and Feasibility of Transendocardial Autologous Bone Marrow Cell Transplantation in Patients With Advanced Heart Disease", *The American journal of cardiology* 97(6), 823-829.
Gambhir, S. S. et al. (2000) "Imaging Transgene Expression with Radionuclide Imaging Technologies", *Neoplasia* 2(1-2), 118-138.
Gao, J. et al. (2001) "The Dynamic in vivo Distribution of Bone Marrow-Derived Mesenchymal Stem Cells after Infusion", *Cells Tissues Organs* 169(1), 12-20.
Garot, J. é. et al. (2003) "Magnetic resonance imaging of targeted catheter-based implantation of myogenic precursor cells into infarcted left ventricular myocardium", *J. Am. Coll. Cardiol.* 41(10), 1841-1846.
Hacein-Bey-Abina, S. et al. (2003) "LMO2-associated clonal T cell proliferation in two patients after gene therapy for SCID-X1", *Science* 302(5644), 415-419.
Hill, J. M. et al. (2003) "Serial Cardiac Magnetic Resonance Imaging of Injected Mesenchymal Stem Cells", *Circulation* 108(8), 1009-1014.
Hinds, K. A. et al. (2003) "Highly efficient endosomal labeling of progenitor and stem cells with large magnetic particles allows magnetic resonance imaging of single cells", *Blood* 102(3), 867-872.
Hoshino, K. et al. (2007) "In vivo tracking in cardiac stem cell-based therapy", *Prog. Cardiovasc. Dis.* 49(6), 414-420.
Josephson, L. et al. (2002) "Near-Infrared Fluorescent Nanoparticles as Combined MR/Optical Imaging Probes", *Bioconjug. Chem.* 13(3), 554-560.
Josephson, L. et al. (1999) "High-Efficiency Intracellular Magnetic Labeling with Novel Superparamagnetic-Tat Peptide Conjugates", *Bioconjug. Chem.* 10(2), 186-191.
Kaul, S. (2008) "Myocardial Contrast Echocardiography", *Circulation* 118(3), 291-308.
Kim, S. et al. (2004) "Near-infrared fluorescent type II quantum dots for sentinel lymph node mapping", *Nat. Biotechnol.* 22(1), 93-97.
Kinnaird, T. et al. (2004) "Marrow-Derived Stromal Cells Express Genes Encoding a Broad Spectrum of Arteriogenic Cytokines and Promote In Vitro and In Vivo Arteriogenesis Through Paracrine Mechanisms", *Circ. Res.* 94(5), 678-685.
Klatzmann, D. et al. (1998) "A Phase I/II Study of Herpes Simplex Virus Type 1 Thymidine Kinase "Suicide" Gene Therapy for Recurrent Glioblastoma", *Hum. Gene Ther.* 9(17), 2595-2604.
Klibanov, A. L. et al. (2004) "Detection of individual microbubbles of ultrasound contrast agents: Imaging of free-floating and targeted bubbles", *Investig. Radiol.* 39(3), 187-195.
Kostarelos, K. et al. (2007) "Cellular uptake of functionalized carbon nanotubes is independent of functional group and cell type", *Nat. Nanotechnol.* 2(2), 108-113.
Langer, R. et al. (2008) "Human Embryoid Bodies Containing Nano- and Microparticulate Delivery Vehicles", *Adv. Mater.* 20(12), 2285-2291.
Langer, R. and Peppas, N. (1983) "Chemical and Physical Structure of Polymers as Carriers for Controlled Release of Bioactive Agents: A Review", *J. Macromol. Sci. Rev. Macromol. Chem. Phys.* C23, 61-126.
Lewin, M. et al. (2000) "Tat peptide-derivatized magnetic nanoparticles allow in vivo tracking and recovery of progenitor cells", *Nat Biotech* 18(4), 410-414.
Lindner, J. R. et al. (2000) "Noninvasive Imaging of Inflammation by Ultrasound Detection of Phagocytosed Microbubbles", *Circulation* 102(5), 531-538.
Main, M. L. et al. (2006) "Pulmonary Hemodynamic Effects of Dipyridamole Infusion in Patients with Normal and Elevated Pulmonary Artery Systolic Pressure Receiving PB127", *Journal of the American Society of Echocardiography : official publication of the American Society of Echocardiography* 19(8), 1038-1044.
Mazhari, R. and Hare, J. M. (2007) "Mechanisms of action of mesenchymal stem cells in cardiac repair: potential influences on the cardiac stem cell niche", *Nat. Clin. Pract. Cardiovasc. Med.* 4, S21-S25.
Modo, M. et al. (2002) "Tracking Transplanted Stem Cell Migration Using Bifunctional, Contrast Agent-Enhanced, Magnetic Resonance Imaging", *Neuroimage* 17(2), 803-811.
Murry, C. E. et al. (2004) "Haematopoietic stem cells do not transdifferentiate into cardiac myocytes in myocardial infarcts", *Nature* 428(6983), 664-668.
Nagaya, N. et al. (2005) "Transplantation of Mesenchymal Stem Cells Improves Cardiac Function in a Rat Model of Dilated Cardiomyopathy", *Circulation* 112(8), 1128-1135.
Nakayama, A. et al. (2002) "Functional near-infrared fluorescence imaging for cardiac surgery and targeted gene therapy", *Molecular Imaging* 1(4), 365-377.
Ntziachristos, V. et al. (2003) "Fluorescence imaging with near-infrared light: new technological advances that enable in vivo molecular imaging", *Eur. Radiol.* 13(1), 195-208.
Partlow, K. C. et al. (2007) "Abstract 1108: Ultrasound Facilitates Stem/Progenitor Cell Labeling and Tracking with Perfluorocarbon Nanobeacons via Fundamental Cell Transport Mechanisms", *Circulation* 116, II_222.
Patel, A. N. et al. (2007) "Improved cell survival in infarcted myocardium using a novel combination transmyocardial laser and cell delivery system", *Cell Transplant.* 16(9), 899-905.
Perin, E. C. et al. (2003) "Transendocardial, Autologous Bone Marrow Cell Transplantation for Severe, Chronic Ischemic Heart Failure", *Circulation* 107(18), 2294-2302.
Pittenger, M. F. et al. (1999) "Multilineage potential of adult human mesenchymal stem cells", *Science* 284 5411(143-7).
Psaltis, P. J. et al. (2008) "Concise Review: Mesenchymal Stromal Cells: Potential for Cardiovascular Repair", *Stem Cells* 26(9), 2201-2210.

(56) References Cited

OTHER PUBLICATIONS

Raisinghani, A. et al. (2003) "Myocardial contrast echocardiography (MCE) with triggered ultrasound does not cause premature ventricular complexes: evidence from PB127 MCE studies", *J. Am. Soc. Echocardiogr. 16*(10), 1037-1042.

Reynolds, J. S. et al. (1999) "Imaging of Spontaneous Canine Mammary Tumors Using Fluorescent Contrast Agents", *Photochem. Photobiol. 70*(1), 87-94.

Rice, B. W. et al. (2001) "In vivo imaging of light-emitting probes", *J. Biomed. Opt. 6*, 432.

Sevick-Muraca, E. M. et al. (2002) "Fluorescence-enhanced, near infrared diagnostic imaging with contrast agents", *Curr. Opin. Chem. Biol. 6*(5), 642-650.

Simonova, M. et al. (2003) "Engineering of technetium-99m-binding artificial receptors for imaging gene expression", *The Journal of Gene Medicine 5*(12), 1056-1066.

Tang, Y. et al. (2003) "In Vivo Tracking of Neural Progenitor Cell Migration to Glioblastomas", *Hum. Gene Ther. 14*(13), 1247-1254.

Toma, C. et al. (2007) "Positive effect of darbepoetin on peri-infarction remodeling in a porcine model of myocardial ischemia—reperfusion", *J. Mol. Cell. Cardiol. 43*(2), 130-136.

Toma, C. et al. (2002) "Human Mesenchymal Stem Cells Differentiate to a Cardiomyocyte Phenotype in the Adult Murine Heart", *Circulation 105*(1), 93-98.

Toma, C. et al. (2009) "Fate of Culture-Expanded Mesenchymal Stem Cells in the Microvasculature", *Circ. Res. 104*(3), 398-402.

van den Bos, E. J. et al. (2003) "Improved Efficacy of Stem Cell Labeling for Magnetic Resonance Imaging Studies by the Use of Cationic Liposomes", *Cell Transplant. 12*(7), 743-756.

Villanueva, F. S. et al. (2001) "Detection of Coronary Artery Stenosis With Power Doppler Imaging", *Circulation 103*(21), 2624-2630.

Wang, X. et al. (2003) "Dynamic tracking of human hematopoietic stem cell engraftment using in vivo bioluminescence imaging", *Blood 102*(10), 3478-3482.

Wickline, S. A. and Lanza, G. M. (2003) "Nanotechnology for Molecular Imaging and Targeted Therapy", *Circulation 107*(8), 1092-1095.

Wu, J. C. et al. (2003) "Molecular Imaging of Cardiac Cell Transplantation in Living Animals Using Optical Bioluminescence and Positron Emission Tomography", *Circulation 108*(11), 1302-1305.

Yanagisawa, K. et al. (2007) "Phagocytosis of ultrasound contrast agent microbubbles by Kupffer cells", *Ultrasound Med. Biol. 33*(2), 318-325.

Yin Win, K. and Feng, S.-S. (2005) "Effects of particle size and surface coating on cellular uptake of polymeric nanoparticles for oral delivery of anticancer drugs", *Biomaterials 26*(15), 2713-2722.

Zhang, S. et al. (2003) "PARACEST Agents: Modulating MRI Contrast via Water Proton Exchange", *Acc. Chem. Res. 36*(10), 783-790.

\* cited by examiner

A.

B.

A.

B.

A.

B.

A.

B.

A.

B.

A.

B.

A.

B.

A.

B.

INTRACELLULAR MICROBUBBLE FOR IMAGING AN ANATOMICAL SITE

FIELD OF INVENTION

The present invention is related to the field of clinical imaging techniques. Improvements in contrast agent technology are described wherein contrast microbubbles are internalized into functional biological cells. The cell-microbubble complexes may be used to track cell migration from one anatomical area to another by ultrasound imaging, or monitor treatment of a diseased and/or injured tissue.

BACKGROUND

Currently, cell therapies administered by intravenous, intra-arterial, and/or direct tissue injection are limited by the lack of clinically available imaging methods to detect the in vivo fate of the administered cells. Current approaches to solve these problems are limited by potential safety issues including, but not limited to, radioactive exposure and/or heavy ion toxicity, and difficulty in serial tracking due to complex instrumentation and/or the requirement for repetitive radiation exposure.

The absence of a reliable technology for in vivo tracking of delivered biological cells has limited the progress and conduct of clinical trials of stem cell therapy. A robust imaging technology for serial, non-invasive, in vivo assessment of stem cell fate after delivery in humans would be a powerful tool, both for pharmaceutical companies conducting trials of cell therapies, as well as for clinicians who would ultimately implement the imaging technology to guide clinical decision making. Furthermore, such an imaging technology would be expected to be useful in the research arena, giving new physiologic insights into stem cell trafficking.

There are currently no reliable in vivo imaging methods for serial tracking of the fate of biological cells delivered for therapeutic purposes. Existing technologies for in vivo cell tracking, still in research stages, include magnetic resonance and nuclear imaging approaches which have disadvantages in terms of radioactive exposure of stem cells and complex instrumentation. What is needed in the art is a portable, non-invasive technique with relatively simple instrumentation, to allow safe, serial, imaging of systemically injected biological cells.

SUMMARY OF THE INVENTION

The present invention is related to the field of clinical imaging techniques. Improvements in contrast agent technology are described wherein contrast microbubbles are internalized into functional biological cells. The cell-microbubble complexes may be used to track cell migration from one anatomical area to another by ultrasound imaging, or monitor treatment of a diseased and/or injured tissue.

In one embodiment, the present invention contemplates a method comprising providing a non-invasive, portable, ultrasound device that can be used to serially image patients undergoing biological cell therapy.

In one embodiment, the present invention contemplates a composition comprising a biological cell with an internalized polymer contrast microbubble. In one embodiment, the microbubble comprises an acoustically active gas. In one embodiment, the biological cell is viable. In one embodiment, the biological cell comprises a stem cell. In one embodiment, the stem cell comprises a mesenchymal stem cell. In one embodiment, the acoustically active gas is selected from the group comprising air, nitrogen, or a perfluorocarbon gas. In one embodiment, the acoustically active gas is a liquid. In one embodiment, the acoustically active liquid comprises a perfluorocarbon. In one embodiment, the contrast microbubble comprises a biodegradable polymer. In one embodiment, the biodegradable polymer comprises a synthetic polymer. In one embodiment, the synthetic polymer is selected from the group comprising polyethylene glycol, polyethylene oxide, polypropylene glycol, amino acids, nucleic acids, or combinations or derivatives thereof. In one embodiment, the contrast microbubble is a controlled fragility microbubble. In one embodiment, the contrast microbubble is a bi-layer microbubble. In one embodiment, the bi-layer microbubble comprises an inner layer and an outer layer. In one embodiment, the biodegradable polymer is selected from the group comprising polycaprolactone, polylactic acid, polylactic-polyglycolic acid co-polymers, co-polymers of lactides and lactones, such as epsilon-caprolactone, delta-valerolactone, polyalkylcyanoacrylates, polyamides, polyhydroxybutryrates, polydioxanones, poly-beta-aminoketones, polyanhydrides, poly-(ortho)esters, polyamino acids, such as polyglutamic and polyaspartic acids or esters of polyglutamic, polyaspartic acids, amino acids, or nucleic acids. In one embodiment, the microbubble comprises an amphiphilic biocompatible material. In one embodiment, the amphiphilic biocompatible material is selected from the group comprising albumin, collagen, gelatin, globulins, glycosamininoglycans, heparin, or chondrotin sulphate.

In one embodiment, the present invention contemplates a method comprising: a) providing; i) a biological cell comprising an internalized contrast microbubble; ii) a patient comprising an anatomical site; iii) an ultrasound device emitting a frequency that is harmonic to the microbubbles; b) administering the internalized microbubble to the patient; and iv) oscillating the microbubbles with the frequency under conditions such that an image of the microbubbles is created. In one embodiment, the biological cell is viable. In one embodiment, the internalized microbubble comprises an acoustically active gas. In one embodiment, the acoustically active gas may be selected from the group comprising air, nitrogen, or a perfluorocarbon gas. In one embodiment, the acoustically active gas is a liquid. In one embodiment, the acoustically active liquid comprises a perfluorocarbon. In one embodiment, the biological cell is viable. In one embodiment, the biological cell comprises a stem cell. In one embodiment, the stem cell comprises a mesenchymal stem cell. In one embodiment, the anatomical site comprises diseased tissue. In one embodiment, the anatomical site comprises injured tissue. In one embodiment, the method further comprises treating the diseased tissue with the stem cell. In one embodiment, the method further comprises treating the injured tissue with the stem cell. In one embodiment, the microbubble comprises a polymer microbubble. In one embodiment, the polymer microbubble comprises a biodegradable polymer. In one embodiment, the biodegradable polymer comprises a synthetic polymer. In one embodiment, the synthetic polymer is selected from the group comprising polyethylene glycol, polyethylene oxide, polypropylene glycol, amino acids, nucleic acids, or combinations or derivatives thereof. In one embodiment, the bi-layer microbubble comprises an inner layer and an outer layer. In one embodiment, the biodegradable polymer is selected from the group comprising polycaprolactone, polylactic acid, polylactic-polyglycolic acid co-polymers, co-polymers of lactides and lactones, such as epsilon-caprolactone, delta-valerolactone, polyalkylcyanoacrylates, polyamides, polyhydroxybutryrates, polydioxanones, poly-beta-aminoketones, polyanhydrides, poly- (ortho)esters, polyamino acids, such as polyglutamic and polyaspartic acids or esters of polyglutamic, polyaspartic acids, amino acids, or nucleic acids. In one embodiment, the microbubble comprises an amphiphilic biocompatible material. In one embodiment, the amphiphilic biocompatible material is selected from the group comprising albumin, collagen, gelatin, globulins, glycosamininoglycans, heparin, or chondrotin sulphate. In one embodiment, the microbubble is a controlled fragility microbubble. In one embodiment, the microbubble comprises a controlled fragility microbubble. In one embodiment, the microbubble is a bi-layer microbubble. In one embodiment, the bi-layer microbubble comprises an inner layer and an outer layer. In one embodiment, the inner layer of the shell comprises a biodegradable polymer. In one embodiment, the outer layer comprises an amphiphilic biocompatible material. In one embodiment, the amphiphilic biocompatible material comprises albumin.

In one embodiment, the present invention contemplates a method comprising: a) providing; i) a biological cell comprising an internalized contrast microbubble; ii) a patient comprising an anatomical site, wherein said anatomical site has an affinity for the biological cell; iii) an ultrasound device capable of scanning the anatomical site; b) contacting the anatomical site with the biological cell; and c) imaging said anatomical site with said ultrasound device. In one embodiment, the biological cell is viable. In one embodiment, the biological cell comprises a stem cell. In one embodiment, the stem cell comprises an mesenchymal stem cell. In one embodiment, the internalized microbubble comprises an acoustically active gas. In one embodiment, the acoustically active gas comprises air, nitrogen, or a perfluorocarbon gas. In one embodiment, the acoustically active gas is a liquid. In one embodiment, the acoustically active liquid comprises a perfluorocarbon. In one embodiment, the biological cell comprises a stem cell. In one embodiment, the anatomical site comprises diseased tissue. In one embodiment, the anatomical site comprises injured tissue. In one embodiment, the method further comprises treating the diseased tissue with the stem cell. In one embodiment, the method further comprises treating the injured tissue with the stem cell. In one embodiment, the microbubble comprises a polymer microbubble. In one embodiment, the polymer microbubble comprises a synthetic polymer. In one embodiment, the synthetic polymer is selected from the group comprising polyethylene glycol, polyethylene oxide, polypropylene glycol, amino acids, nucleic acids, or combinations or derivatives thereof. In one embodiment, the polymer microbubble comprises a biodegradable polymer. In one embodiment, the biodegradable polymer is selected from the group comprising polycaprolactone, polylactic acid, polylactic-polyglycolic acid co-polymers, co-polymers of lactides and lactones, such as epsilon-caprolactone, delta-valerolactone, polyalkylcyanoacrylates, polyamides, polyhydroxybutryrates, polydioxanones, poly-beta-aminoketones, polyanhydrides, poly-(ortho)esters, polyamino acids, such as polyglutamic and polyaspartic acids or esters of polyglutamic, polyaspartic acids, amino acids, or nucleic acids. In one embodiment, the microbubble comprises an amphiphilic biocompatible material. In one embodiment, the amphiphilic biocompatible material is selected from the group comprising albumin, collagen, gelatin, globulins, glycosamininoglycans, heparin, or chondrotin sulphate. In one embodiment, the microbubble comprises a bi-layer microbubble. In one embodiment, the bi-layer microbubble comprises an inner layer and an outer layer. In one embodiment, the inner layer of the shell comprises a biodegradable polymer. In one embodiment, the outer layer comprises an amphiphilic biocompatible material. In one embodiment, the amphiphilic biocompatible material comprises albumin. In one embodiment, the microbubble comprises a controlled fragility microbubble.

In one embodiment, the present invention contemplates a method comprising: a) providing; i) a biological cell comprising an internalized contrast microbubble; ii) a patient comprising at least one symptom of a diseased anatomical site; and b) treating the anatomical site with the internalized microbubble such that the at least one symptom is reduced. In one embodiment, the method further comprises scanning the anatomical site with an ultrasound device to track said symptom reduction. In one embodiment, the biological cell is viable. In one embodiment, the biological cell comprises a stem cell. In one embodiment, the stem cell comprises an mesenchymal stem cell. In one embodiment, the internalized microbubble comprises an acoustically active gas. In one embodiment, the acoustically active gas may be selected from the group comprising air, nitrogen, or a perfluorocarbon gas. In one embodiment, the acoustically active gas is a liquid. In one embodiment, the acoustically active liquid comprises a perfluorocarbon. In one embodiment, the biological cell comprises a stem cell. In one embodiment, the microbubble comprises a polymer microbubble. In one embodiment, the biodegradable polymer is selected from the group comprising polycaprolactone, polylactic acid, polylactic-polyglycolic acid co-polymers, co-polymers of lactides and lactones, such as epsilon-caprolactone, delta-valerolactone, polyalkylcyanoacrylates, polyamides, polyhydroxybutryrates, polydioxanones, poly-beta-aminoketones, polyanhydrides, poly-(ortho)esters, polyamino acids, such as polyglutamic and polyaspartic acids or esters of polyglutamic or polyaspartic acids In one embodiment, the microbubble comprises an amphiphilic biocompatible material. In one embodiment, the amphiphilic biocompatible material is selected from the group comprising albumin, collagen, gelatin, globulins, glycosamininoglycans, heparin, or chondrotin sulphate. In one embodiment, the microbubble comprises a bi-layer microbubble. In one embodiment, the bi-layer microbubble comprises an inner layer and an outer layer. In one embodiment, the inner layer of the shell comprises a biodegradable polymer. In one embodiment, the outer layer comprises an amphiphilic biocompatible material. In one embodiment, the amphiphilic biocompatible material comprises albumin. In one embodiment, the microbubble comprises a controlled fragility microbubble.

In one embodiment, the present invention contemplates a method comprising: a) providing; i) a biological cell comprising an internalized contrast microbubble; ii) a patient comprising at least one symptom of an injured anatomical site; and b) treating the anatomical site with the internalized microbubble such that the at least one symptom is reduced. In one embodiment, the method further comprises scanning the anatomical site with an ultrasound device to track said symptom reduction. In one embodiment, the biological cell is viable. In one embodiment, the biological cell comprises a stem cell. In one embodiment, the stem cell comprises an mesenchymal stem cell. In one embodiment, the internalized microbubble comprises an acoustically active gas. In one embodiment, the acoustically active gas may be selected from the group comprising air, nitrogen, or a perfluorocarbon gas. In one embodiment, the acoustically active gas is a liquid. In one embodiment, the acoustically active liquid comprises a perfluorocarbon. In one embodiment, the biological cell comprises a stem cell. In one embodiment, the microbubble comprises a polymer microbubble. In one embodiment, the biodegradable polymer is selected from the group comprising polycaprolactone, polylactic acid, polylactic-polyglycolic acid co-polymers, co-polymers of lactides and lactones, such as epsilon-caprolactone, delta-valerolactone, polyalkylcyanoacrylates, polyamides, polyhydroxybutryrates, polydioxanones, poly-beta-aminoketones, polyanhydrides, poly-(ortho)esters, polyamino acids, such as polyglutamic and polyaspartic acids or esters of polyglutamic or polyaspartic acids In one embodiment, the microbubble comprises an amphiphilic biocompatible material. In one embodiment, the amphiphilic biocompatible material is selected from the group comprising albumin, collagen, gelatin, globulins, glycosamininoglycans, heparin, or chondrotin sulphate. In one embodiment, the microbubble comprises a controlled fragility microbubble. In one embodiment, the microbubble comprises a bi-layer microbubble. In one embodiment, the bi-layer microbubble comprises an inner layer and an outer layer. In one embodiment, the inner layer of the shell comprises a biodegradable polymer. In one embodiment, the outer layer comprises an amphiphilic biocompatible material. In one embodiment, the amphiphilic biocompatible material comprises albumin.

In one embodiment, the present invention contemplates a method comprising: a) providing; i) a biological cell comprising an internalized contrast microbubble; ii) a patient comprising a first anatomical site and a second anatomical site; iii) an ultrasound device emitting a frequency that is harmonic to the microbubbles; b) administering the internalized microbubble to the patient; and c) tracking the microbubbles with the ultrasound device from the first anatomical site to the second anatomical site. In one embodiment, the biological cell is viable. In one embodiment, the first anatomical site comprises a parental cell. In one embodiment, the second anatomical site comprises a daughter cell.

A kit comprising: a) a first container comprising a biological cell comprising an internalized contrast microbubble; b) a second container comprising a pharmaceutically acceptable vehicle compatible with the biological cell; and c) a set of instructions describing; i) administering the biological cell in the vehicle to a patient; and ii) detecting the microbubbles in the patient with an ultrasound device. In one embodiment, the biological cell is viable. In one embodiment, the biological cell comprises a stem cell. In one embodiment, the stem cell comprises an mesenchymal stem cell. In one embodiment, the internalized microbubble comprises an acoustically active gas. In one embodiment, the acoustically active gas may be selected from the group comprising air, nitrogen, or a perfluorocarbon gas. In one embodiment, the acoustically active gas is a liquid. In one embodiment, the acoustically active liquid comprises a perfluorocarbon. In one embodiment, the biological cell comprises a stem cell. In one embodiment, the microbubble comprises a polymer microbubble. In one embodiment, the microbubble comprises a controlled fragility microbubble. In one embodiment, the microbubble comprises a bi-layer microbubble. In one embodiment, the bi-layer microbubble comprises an inner layer and an outer layer. In one embodiment, the inner layer of the shell comprises a biodegradable polymer. In one embodiment, the outer layer comprises an amphiphilic biocompatible material. In one embodiment, the amphiphilic biocompatible material comprises albumin. In one embodiment, the microbubble comprises a controlled fragility microbubble.

DEFINITIONS

The term "polymer contrast microbubble" as used herein, refers to any approximately spherical structure comprising at least one polymer having a diameter of approximately 100 nanometer to 10 microns. Microbubbles may comprises a single layer surface or a bi-layer surface. The compositions of these microbubbles result in a harmonic oscillation to certain ultrasound frequencies, such that their emissions may be visualized as an image. Alteration of polymer characteristics including, but not limited to, polymer type or concentration, can modify the structural and functional characteristics of a microbubble. Polymers may comprise a linked series of individual components, wherein the components may include, but are not limited to, small organic molecules, amino acids, or nucleic acids. For example, a polymer as contemplated herein includes a peptide or protein and/or an oligonucleotide. A microbubble may contain single or multiple pockets which hold a gas (i.e, for example, an acoustically active gas) or a liquid (i.e., for example, an acoustically active liquid, for example those by Wickline). In general, microbubbles are roughly spherical or irregular shape and have at least one continuous phase comprising a polymer as defined herein. Further, the continuous phase may form one or multiple enclosures capable of entrapping a gas or liquid (i.e., for example, gases or liquids that are acoustically active). Microbubbles may be fabricated by various methods including, but not limited to, double emulsion evaporation or extraction, single emulsion evaporation or extraction, spray drying, freeze spray drying, ultrasound sonication, or microfluidics.

The term "bi-layer microbubble" as used herein, refers to any microbubble comprising a shell having an inner and outer layer. Generally, the outer layer comprises ligands that are amphiphilic and biocompatible (i.e., for example, albumin) and the inner layer comprises biodegradable polymers. The bi-layer is usually from between approximately 25-750 nm in width.

The term "controlled fragility microbubble" as used herein, refers to microbubbles within a population of microbubbles having the same wall thickness to diameter ratio.

The term "internalized microbubble" as used herein refers to any microbubble that resides within the intracellular space of a biological cell. Although it is not necessary to understand the mechanism of an invention, it is believed that such internalization may take place by endocytosis by the biological cell.

The term "microparticles" as used herein, refer to solid particles ranging from 100 nm to 10 microns in diameter which lack pores such that a gas or liquid is unable to become embedded in the solid continuous phase. Microparticles may be fabricated by various methods including, but not limited to, double emulsion evaporation or extraction, single emulsion evaporation or extraction, spray drying, freeze spray drying, ultrasound sonication, or microfluidics.

The term "biological cell' as used herein, refers to any cellular structure having biological functionality including, but not limited to, endocytosis and/or extracellular ligand binding sites. A biological cell may be naturally occurring or synthetic and is preferably viable. Such biological cells may be a stem cell including, but not limited to, bone marrow-derived stem cells, embryonic stem cells, adult stem cells, hemopoeitic stem cells, mesenchymal stem cells, epidermal stem cells, endothelial stem cells, endothelial progenitor cells, resident cardiac stem cells, pluripotent stem cells, adipose-derived stem cells, cancer stem cells (i.e., for example, a leukemic hemopoeitic stem cell) or skeletal myoblasts. Alternatively, biological cells may include, but are not limited to, brain cells, liver cells, muscle cells, nerve cells, chondrocytes, lymphocytes, intestinal cells, pancreatic cells, liver cells, heart cells, lung cells, colon cells, bladder cells, uterine cells, prostate cells, urethra cells, testicular cells, and/or epithelial cells. Further, a biological cell may be a cancerous cell, for example, a dendritic cell.

The term "parental cell" as used herein, refers to any biological cell having the capability of under going cellular division (i.e., for example, mitosis), such that at least two daughter cells are created.

The term "daughter cell" as used herein, refers to any biological cell created by cellular division (i.e., for example, mitosis) of a parental cell.

The term "contrast agent" as used herein refers to any composition capable of improving the resolution between at least two different structures having differential densities. Contrast agents contemplated herein include, but are not limited to, polymer microbubbles, stabilized microbubbles, sonicated albumin, gas-filled microspheres, gas-filled liposomes, and gas-forming emulsions.

The term "controlled fragility" as used herein, refers to any microbubble population having the characteristic of being rupturable only when exposed to acoustic energy equal to or greater than a predetermined intensity. That is, below this acoustic intensity threshold, substantially all the microbubbles remain intact while above the acoustic intensity threshold all the microbubbles rupture essentially simultaneously.

The term "acoustically active gas" as used herein, refers to any gaseous compound that has a kinetic response to the presence of an ultrasound transmission frequency. Representative acoustically active gases include but are not limited to, air, nitrogen and/or perfluorocarbon gases. The high molecular weight, low diffusivity and low solubility of the perfluorocarbon gas favors retention within a shell and also may persist even if the shell were to become disrupted to create an unencapulsated microbubble.

The term "acoustically active liquid" as used herein, refers to any liquid compound that has a kinetic response to the presence of an ultrasound transmission frequency. For example, an acoustically active liquid may comprise a perfluorocarbon.

The term "ultrasound device" as used herein, refers to any device capable of generating vibrations of the same physical nature as sound but with frequencies above the range of human hearing. See, for example, Friemel et al., "Ultrasound signal processing system" U.S. Pat. No. 5,709,209 (herein incorporated by reference). The ultrasound device may be used in the diagnostic or therapeutic uses especially a noninvasive technique involving the formation of a two-dimensional image used for the examination and measurement of internal body structures and the detection of bodily abnormalities—called also echography, sonography, ultrasonography. Alternatively, other non-linear ultrasound detection scanning systems include, but are not limited to, pulse inversion, amplitude modulation, harmonic power Doppler, ultraharmonics (Philips, GE), or subharmonics. See, for example, Rafter et al., "Ultrasonic imaging to detect coronary artery stenosis at rest" U.S. Pat. No. 6,730,036 (herein incorporated by reference).

The term "harmonic frequency" as used herein, any frequency that is an integer multiple of a fundamental frequency. As described herein, an ultrasound frequency may result in microbubble oscillations at a harmonic frequency such that an image of the microbubbles can be detected.

The term "anatomical site" as used herein, refers to any location within a biological organism comprising a tissue, organ, and/or plurality of cells.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. These terms are not intended to be limited to eliminating symptoms. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "treating" as used herein, refers to the administration of any composition and/or compound with the intent to reduce the symptoms of a medical conditions. For example, the composition and/or compound may be administered for treating a disease and/or injury.

The term "imaging" as used herein, refers to any technique wherein a visual representation of a biological cell is created. Such imaging may occur either in vitro, in situ, or in vivo. With specific reference to in vivo imaging, the resolution of the visual representations may be enhanced when performed in combination with a contrast agent.

The term "tracking" as used herein, refers to monitoring the migration of a composition from one physical location to another physical location by using imaging techniques. For example, a biological cell comprising internalized microbubbles may be monitored during a migration from a first anatomical site to a second anatomical site.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The term "injury" as used herein, denotes a bodily disruption of the normal integrity of tissue structures. In one sense, the term is intended to encompass surgery. In another sense, the term is intended to encompass irritation, inflammation, infection, and the development of fibrosis. In another sense, the term is intended to encompass wounds including, but not limited to, contused wounds, incised wounds, lacerated wounds, non-penetrating wounds (i.e., wounds in which there is no disruption of the skin but there is injury to underlying structures), open wounds, penetrating wound, perforating wounds, puncture wounds, septic wounds, subcutaneous wounds, burn injuries etc.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "administered" or "administering" as used herein, refers to any method of providing a composition (i.e., for example, a biological cell comprising an internalized microbubble) to a patient such that the composition has its intended effect on the patient. For example, one method of administering is by an indirect mechanism using a medical device such as, but not limited to a catheter, applicator gun, syringe etc. A second exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal and need not be hospitalized. For example, outpatients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "derived from" as used herein, refers to the source of a compound or sequence. In one respect, a compound or sequence may be derived from an organism or particular species. In another respect, a compound or sequence may be derived from a larger complex or sequence.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier" or "pharmaceutically acceptable vehicle", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to molecules that are removed from their natural environment, isolated or separated, and are at least 60% free, preferably 75% free, and more preferably 90% free from other components with which they are naturally associated. The term "biocompatible", as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials.

The term "biodegradable" as used herein, refers to any material that can be acted upon biochemically by living cells or organisms, or processes thereof, including water, and broken down into lower molecular weight products such that the molecular structure has been altered.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabelled A) in a reaction containing labeled "A" and the antibody will reduce the amount of labeled A bound to the antibody.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 2A: Diamonds: Polymer microbubbles at 1× concentration. Squares: Polymer contrast microbubbles at a 1× concentration. Triangles: Cells alone. Cross: Polymer contrast microbubbles at 2× concentration. FIG. 2B: Diamonds: Second determination of polymer contrast microbubbles at 2× concentration.

FIG. 3A: Diamonds: Polymer contrast microbubbles at 1× concentration. Squares: Polymer contrast microbubbles+ cells. Triangles: Cells alone. Cross: Polymer contrast microbubbles at 2× concentration. FIG. 3B: Diamonds: Second determination of polymer contrast microbubbles at 2× concentration.

FIG. 4A: Diamonds: Polymer contrast microbubbles at 1× concentration. Squares: Polymer contrast microbubbles+ cells. Triangles: Cells alone. Cross: Polymer contrast microbubbles at 2× concentration. FIG. 4B: Diamonds: Second determination of polymer contrast microbubbles at 2× concentration.

FIG. 5A: Polymer contrast microbubbles at a 1× concentration. Diamonds: 200 mV. Squares: 300 mV. Triangles: 400 mV. FIG. 5B: Polymer contrast microbubbles at a 2× concentration. Diamonds: 400 mV. Squares: 300 mV. Triangles: 200 mV.

FIG. 27A: A confocal imaging comparison of selected flourescently labeled contrast microbubble-hMSC complexes are presented under brightfield (Panel F, left) or fluorescence microscopy (Panel F, right). FIG. 27B: Representative data showing a labeling efficiency of ~91%.

FIG. 29A: Frequency profile of hMSC-microbubble complexes after a transmission fundamental frequency of 5 MHz, wherein the hMSC-microbubble complexes emit non-linear $1^{st}$ and $2^{nd}$ harmonic signals. FIG. 29B: Second harmonic frequency of hMSC-microbubbles verus hMSC comparisons at MI's=0.7, 0.9, and 1.1.

FIG. 30A: hMSCs only (upper panels); hMSCs comprising internalized microbubbles (lower panels). Video intensity is measured in regions of interest drawn in the test sample (circle). FIG. 30B: Representative data showing the measured video intensity comparing contrast pulse sequencing (CPS) ultrasound and harmonic ultrasound.

DETAILED DESCRIPTION OF THE INVENTION

The present invention is related to the field of clinical imaging techniques. Improvements in contrast agent technology are described wherein contrast microbubbles are internalized into functional biological cells. The cell-microbubble complexes may be used to track cell migration from one anatomical area to another by ultrasound imaging, or monitor treatment of a diseased and/or injured tissue.

In one embodiment, the present invention contemplates a method to track biological cells using ultrasound and polymer contrast microbubbles. In one embodiment, the microbubbles are acoustically active, biocompatible and stable. In one embodiment, the microbubbles comprise polymers including, but not limited to, biodegradable polymers, synthetic polymer, or naturally occurring polymers. Although it is not necessary to understand the mechanism of an invention, it is believed that after incubation with stem cells, the polymer microbubbles are internalized by the stem cells so as to be detected by ultrasound in a living organism in real time. Since ultrasound is a portable, non-invasive technique with relatively simple instrumentation, this application should allow safe, serial, imaging of systemically injected biological cells.

I. Polymer Microbubbles

In one embodiment, the present invention contemplates a chemical composition comprising a polymer microbubble. In one embodiment, the chemical composition comprises a pharmaceutically acceptable composition that can be used as a contrast agent.

Figure 1:
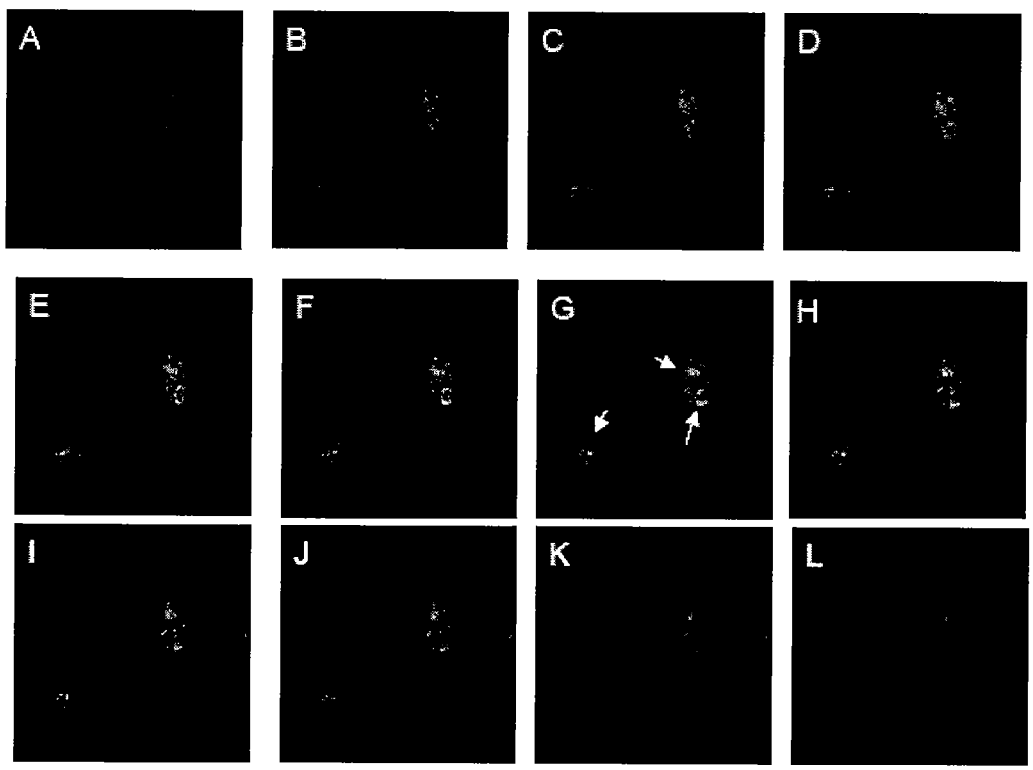
FIG. 1 presents exemplary data showing stacked confocal microscopic images of 3 stem cells (green, arrows). Flourescently-labeled polymer contrast microbubbles (boron-dipyrromethene (BODIPY)) have been internalized by the cells.
Figure 2:
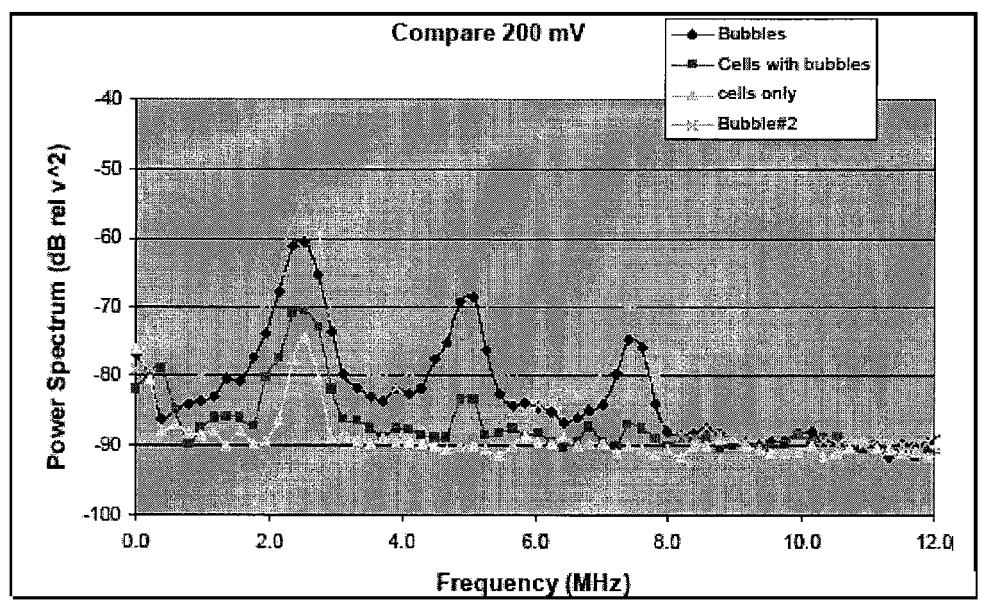
FIG. 2 presents exemplary data of 200 mV power spectra characterizations of internalized microbubbles (MI ~0.5).
Figure 2:
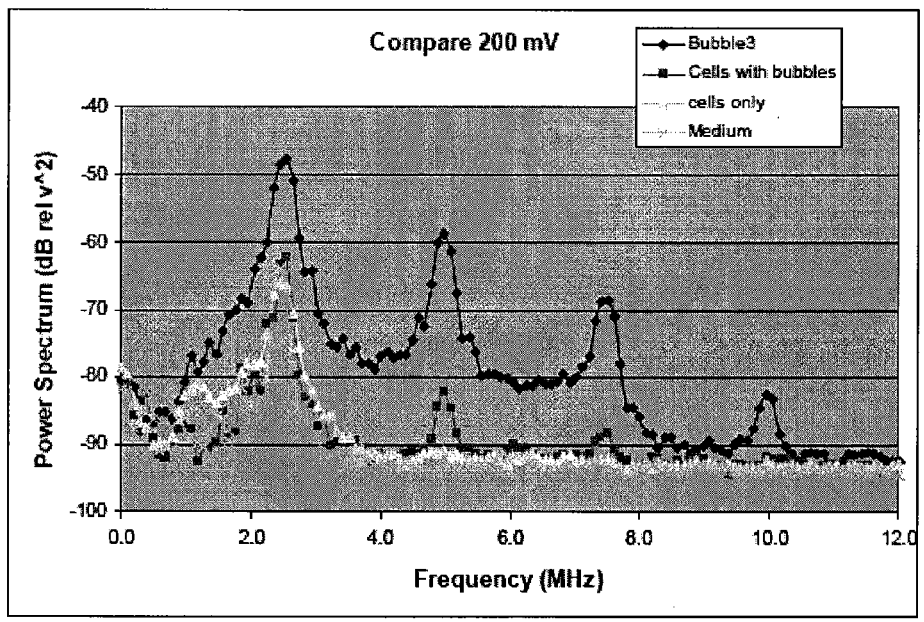
Figure 3:
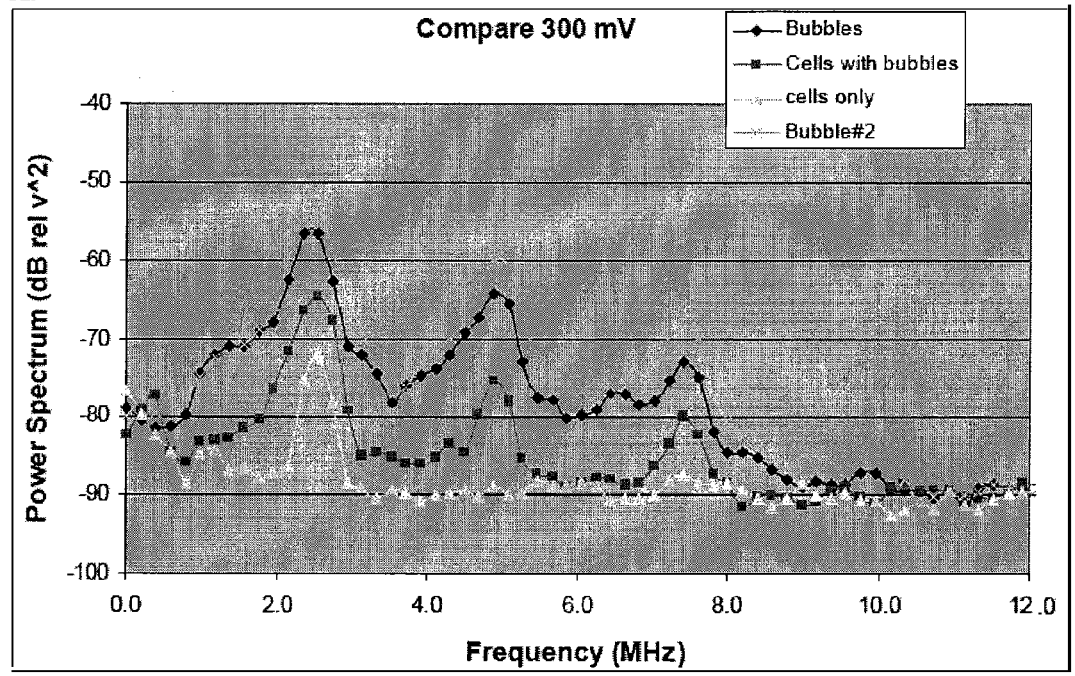
FIG. 3 presents exemplary data of 300 mV power spectra characterizations of internalized microbubbles (MI ~0.7).
Figure 3:
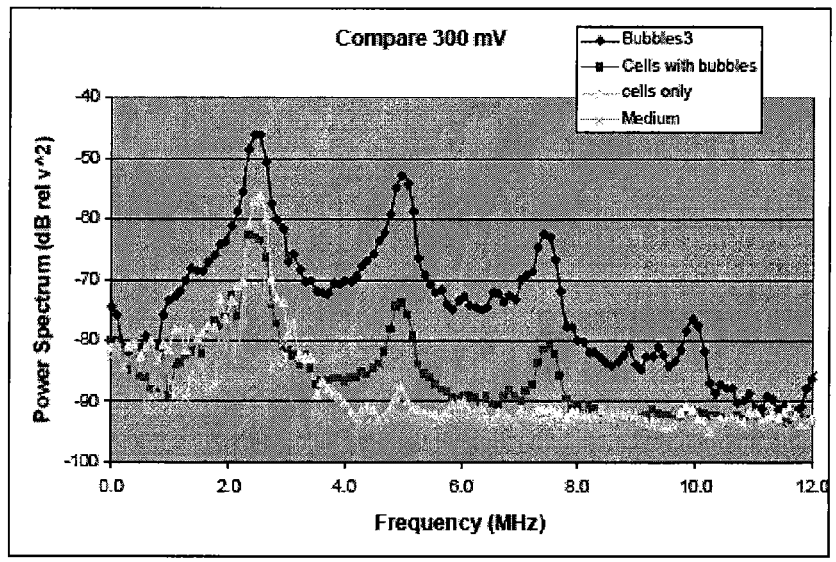
Figure 4:
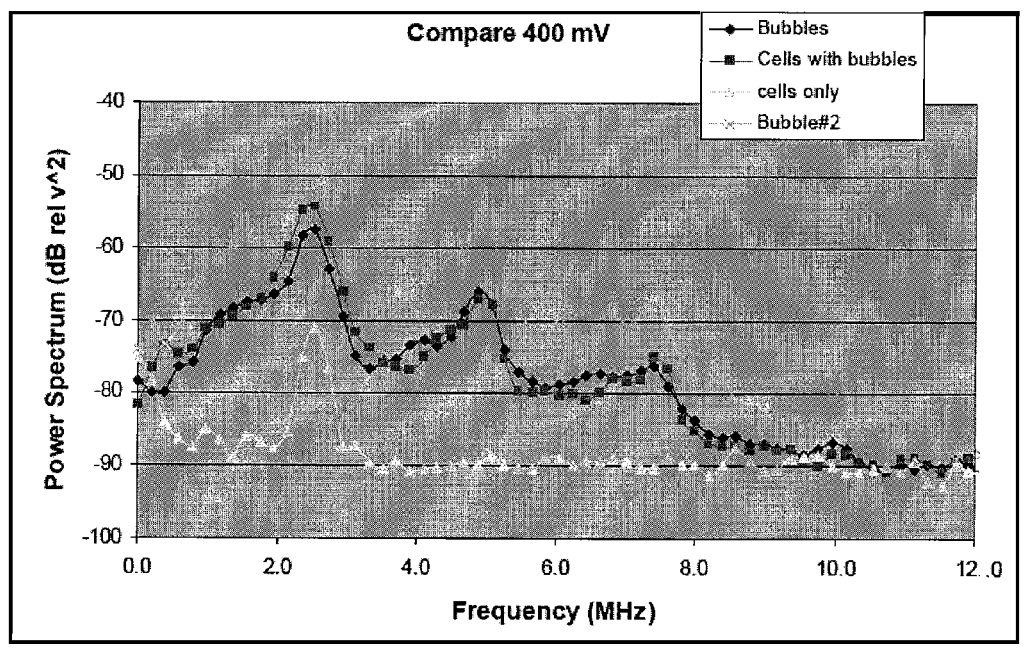
FIG. 4 presents exemplary data of 400 mV power spectra characterizations of internalized microbubbles (MI ~1.0).
Figure 4:
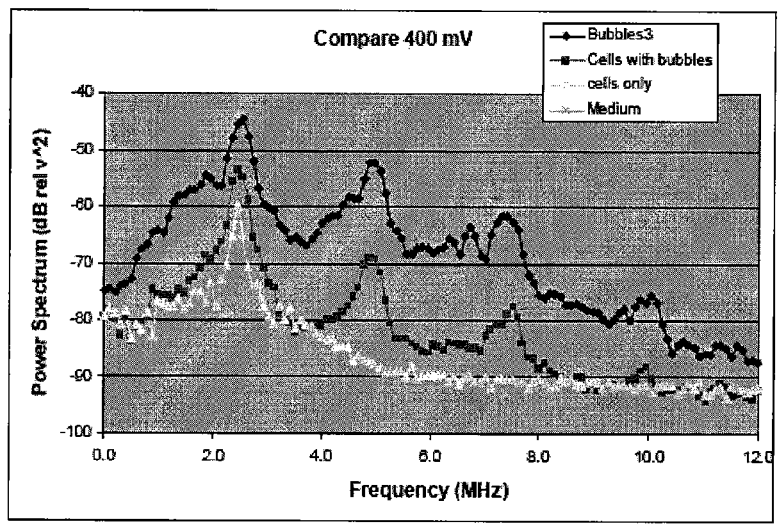
Figure 5:
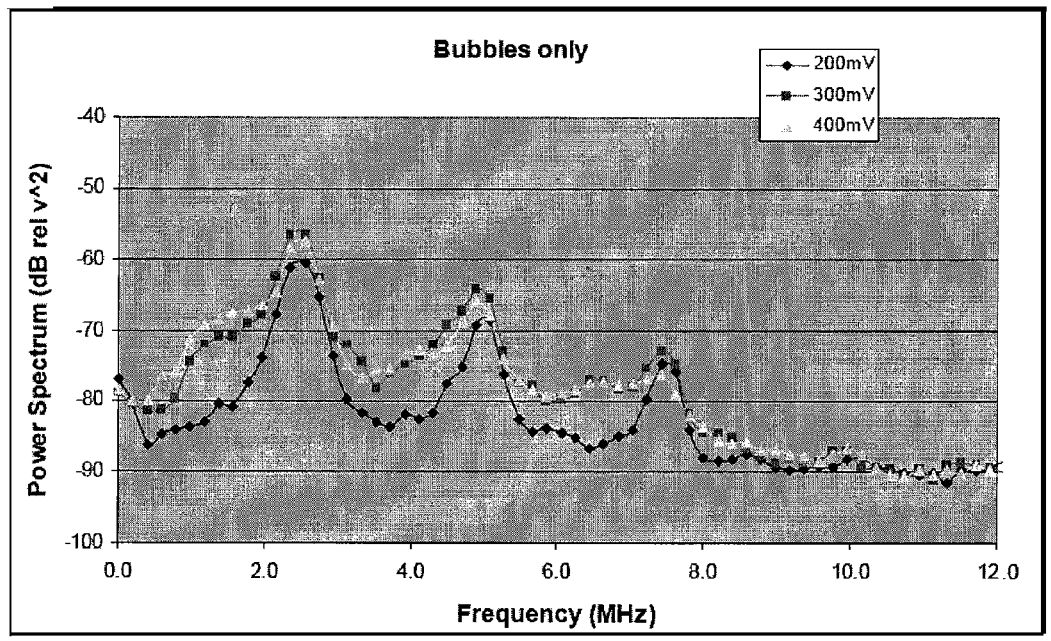
FIG. 5 presents exemplary data of 200-400 mV power spectra characterizations of microbubbles only.
Figure 5:
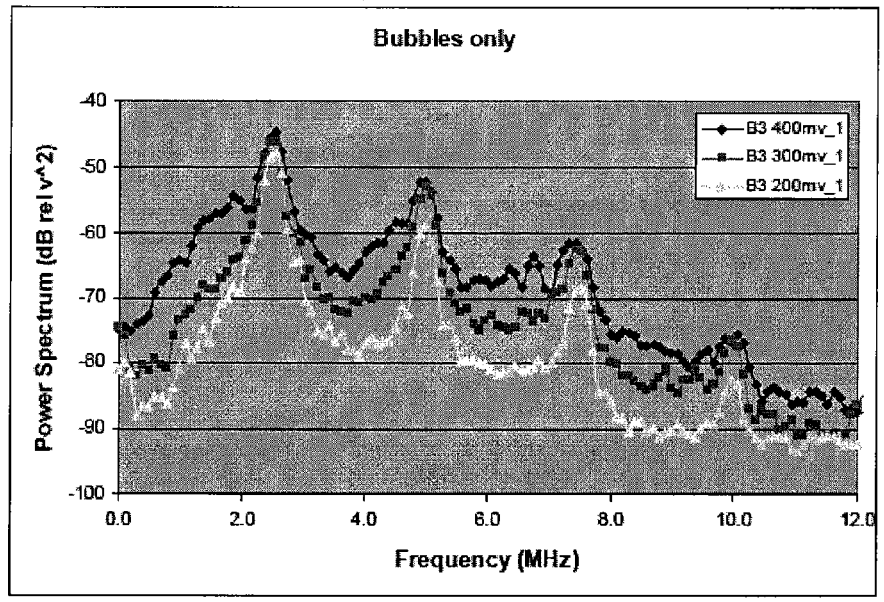
Figure 6:
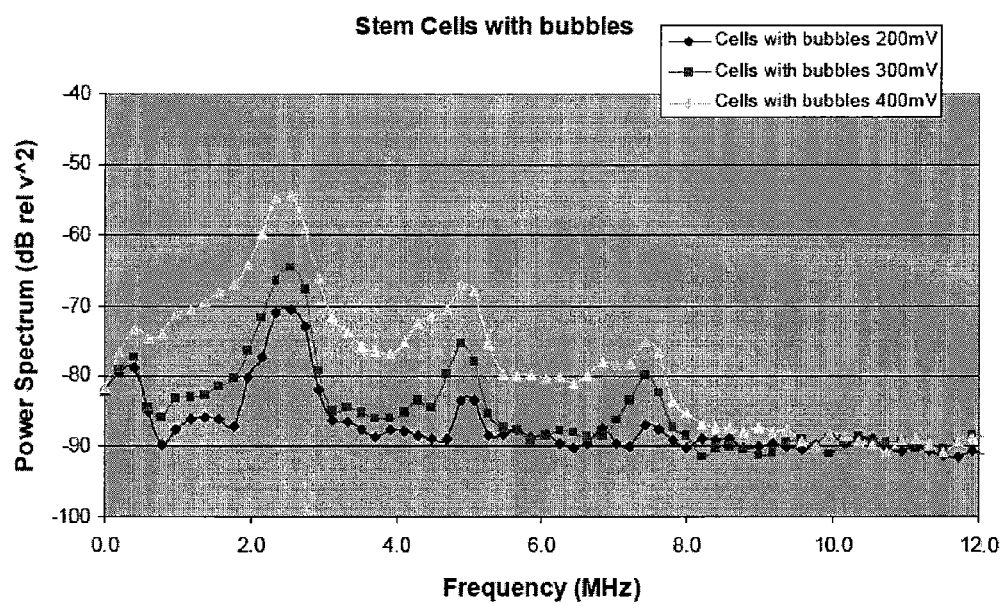
FIG. 6 presents exemplary data of 200-400 mV power spectra characterizations of internalized polymer contrast microbubbles. Diamonds: 200 mV. Squares: 300 mV. Triangles: 400 mV.
Figure 7:
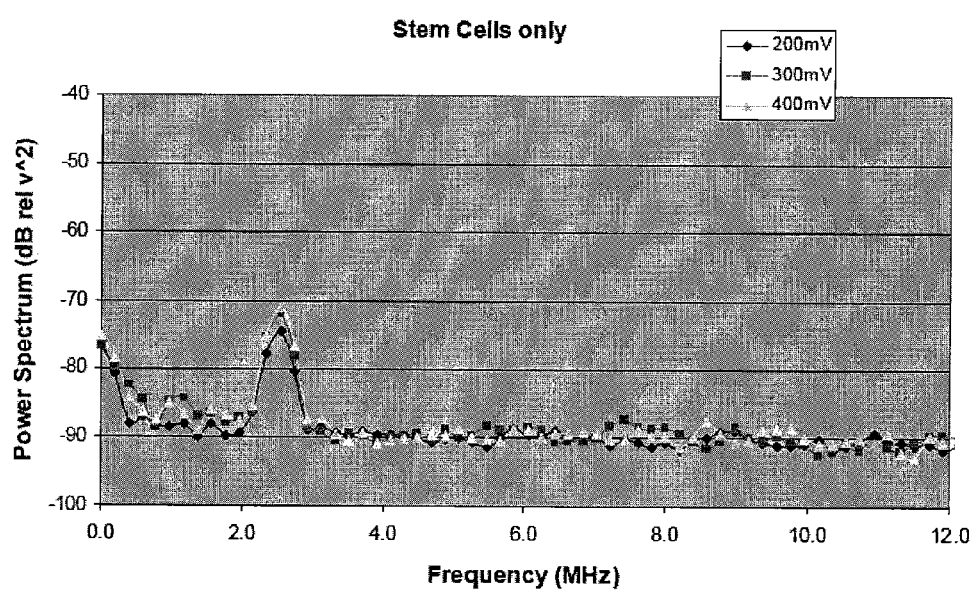
FIG. 7 presents exemplary data of 200-400 mV power spectra characterizations of free cells. Diamonds: 200 mV. Squares: 300 mV. Triangles: 400 mV.
Figure 8:
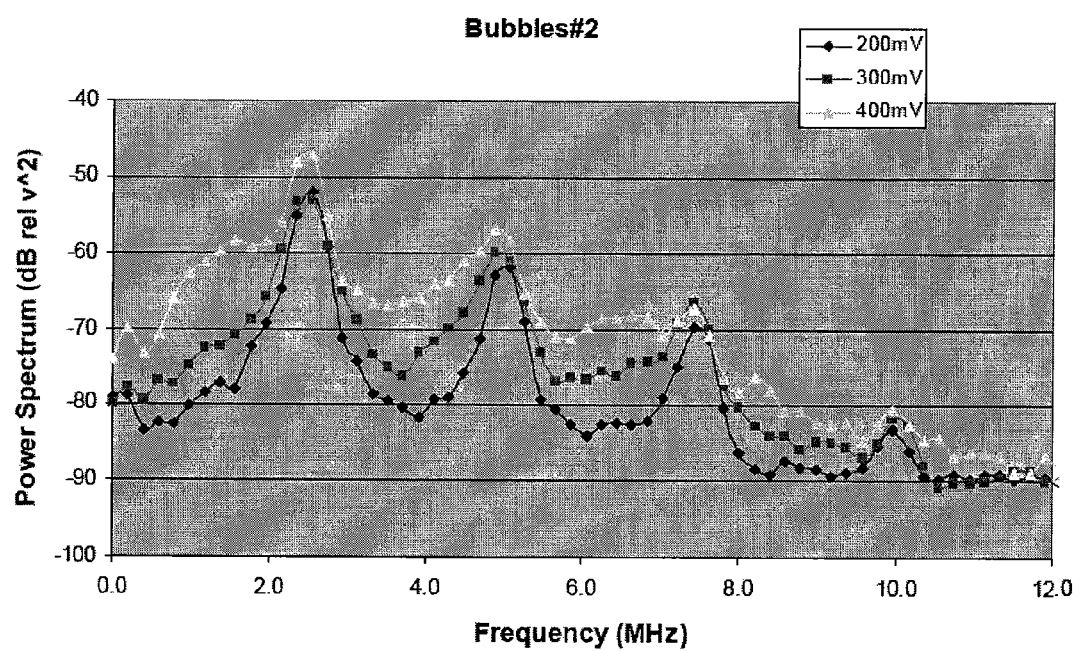
FIG. 8 presents exemplary data of 200-400 mV power spectra characterizations of free polymer contrast microbubbles (2×). Diamonds: 200 mV. Squares: 300 mV. Triangles: 400 mV.
Figure 9:
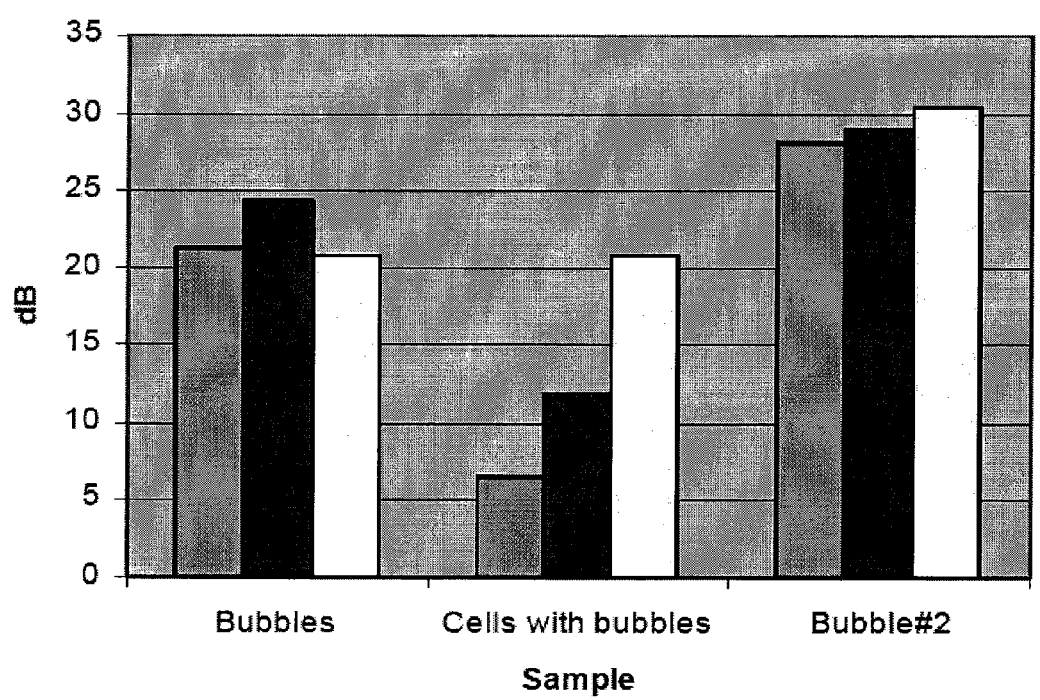
FIG. 9 presents exemplary data showing the relative harmonic level of i) free polymer contrast microbubbles (1×); ii) internalized polymer contrast microbubbles; and iii) free polymer contrast microbubbles (2×). Purple Bar: MI=0.5; Red Bar: MI=0.7. Yellow Bar: MI=1.0.

The development of methods comprising these polymer contrast microbubbles was accomplished by proceeding through an empirical series of experiments including, but not limited to: i) Internalization Of Microbubbles: Commercially available and custom chemical polymer coated microbubbles and/or microparticles were used for internalization into biological cells (i.e., for example, cultured human mesenchymal stem cells) using a reproducible protocol verified using confocal microscopy and transmission electron microscopy. See, FIG. 1.; ii) Microbubbles can remain acoustically active after biological cell internalization: This characteristic was demonstrated by: a) Acoustic testing—Cells with internalized polymer contrast microbubbles demonstrate fundamental and harmonic frequency backscatter whereas cells without internalized microbubbles do not demonstrate any harmonic backscatter. Although it is not necessary to understand the mechanism of an invention, it is believed that that the cells+ microbubble condition produces a unique acoustic signature distinguishable from cells without microbubbles; and b) Ultrasound imaging—Cells+ microbubbles vs. cells only vs. microbubbles only, corroborate the acoustic testing. That is, using non-linear (harmonic) imaging approaches, the cells containing microbubbles can be imaged with 2 dimensional ultrasound, whereas the cells without the microbubbles are not visualized during ultrasound imaging; and iii) Viability studies of the cell+ microbubble complex after exposure to ultrasound: There was no significant loss in cell viability resulting from microbubble internalization and/or exposure to ultrasound. These data establish that biological cells can be internalized with microbubbles, be rendered acoustically active, imaged with two dimensional ultrasound, and suffer no loss of viability acutely.

In one embodiment, the present invention contemplates a composition comprising an acoustically active polymer contrast microbubble. In one embodiment, the present invention also contemplates a method for imaging polymer contrast microbubbles internalized by human mesenchymal stem cells. In one embodiment, the method further comprises in vivo tracking of biological cells. In one embodiment, the polymer contrast microbubble may be a commercially available polymer contrast microbubbles (i.e., for example, Point Biomedical Corporation). Ottoboni et al., "Microparticles Useful As Ultrasonic Contrast Agents And For Delivery Of Drugs Into The Bloodstream" United States Patent Application 2009/0081130; and Conston et al., "Method for ultrasound triggered drug delivery using hollow microbubbles with controlled fragility" United States Patent Application 2005/0283098 (both herein incorporated by reference)(The University of Pittsburgh is currently the owner of the Point Biomedical portfolio's).

A. A Bi-Layer Microbubble

In one embodiment, the present invention contemplates a method of imaging providing a plurality of polymer contrast microbubbles comprising a bi-layered shell. In one embodiment, the outer layer of the shell comprises a biologically compatible material or biomaterial. In one embodiment, the inner layer of the shell comprises a biodegradable polymer, which may be a synthetic polymer. Although it is not necessary to understand the mechanism of an invention, it is believed that the synthetic polymer may be tailored to provide various mechanical and acoustic properties to the shell. In one embodiment, the bi-layer shell microbubble further comprises an acoustically active gas including, but not limited to, air, nitrogen, or a perfluorocarbon gas.

The outer shell layer can be made of a biocompatible material which is typically amphiphilic, that is, has both hydrophobic and hydrophilic characteristics. Blood compatible materials are particularly preferred. Such preferred materials are biological materials including, but not limited to, proteins such as collagen, gelatin or serum albumins or globulins, either derived from humans or having a structure similar to the human protein, glycosoaminoglycans such as hyaluronic acid, heparin and chondrotin sulphate and to combinations or derivatives thereof. Synthetic biodegradable polymers, such as polyethylene glycol, polyethylene oxide, polypropylene glycol and combinations or derivatives may also be used. The outer layer is typically amphiphilic, as well as having a chemistry which allows charge and chemical modification. The versatility of the surface allows for such modifications as altering the charge of the outer shell, such as by selecting a type A gelatin having an isoelectric point above physiological pH, or by using a type B gelatin having an isoelectric point below physiological pH. The outer surfaces may also be chemically modified to enhance biocompatibility, such as by PEGylation, succinylation or amidation, as well as being chemically binding to the surface targeting moiety for binding to selected tissues. The targeting moieties may be antibodies, cell receptors, lectins, selectins, integrins or chemical structures or analogues of the receptor targets of such materials. The mechanical properties of the outer layer may also be modified, such as by cross linking, to make the microbubbles suitable for passage to the left ventricle, to provide a particular resonant frequency for a selected harmonic of the diagnostic imaging system, or to provide stability to a threshold diagnostic imaging level of the ultrasound radiation.

The inner shell layer can be made of a biodegradable polymer, which may be a synthetic polymer. An advantage of the inner shell is that it provides additional mechanical properties to the microbubble which are not provided or insufficiently provided by the outer layer, or enhances mechanical properties not sufficiently provided by the outer layer, without being constrained by surface property requirements. For example, a biocompatible outer layer of a cross-linked proteinaceous hydrogel can be physically supported using a high modulus synthetic polymer as the inner layer. The polymer may be selected for its modulus of elasticity and elongation, which define the desired mechanical properties. Typical biodegradable polymers include polycaprolactone, polylactic acid, polylactic-polyglycolic acid co-polymers, co-polymers of lactides and lactones, such as epsilon-caprolactone, delta-valerolactone, polyalkylcyanoacrylates, polyamides, polyhydroxybutryrates, polydioxanones, poly-beta-aminoketones, polyanhydrides, poly-(ortho)esters, polyamino acids, such as polyglutamic and polyaspartic acids or esters of polyglutamic and polyaspartic acids. Langer, et. al. (1983) *Macromol. Chem. Phys*. C23, 61-125.

The combined thickness of the outer and inner layers of a microbubble shell can be varied depending upon the desired mechanical properties, but typically the total shell thickness ranges between approximately 25 to 750 nm. For example, the wall thickness of both the outer and inner layers may be adjusted by varying the concentration of the components in the microparticle-forming solutions. The mechanical properties of the microbubbles may be controlled, not only by the total wall thickness and thicknesses of the respective layers, but also by selection of materials used in each of the layers by their modulus of elasticity and elongation, and degree of cross-linking of the layers. Upon certain conditions involving rapid deposition of the inner polymer or very low inner polymer content porosity of the inner polymer shell is observed. The pores range from approximately 0.1 to 2 micron in diameter as observed under electron microscopy. Mechanical properties of the layers may also be modified with plasticizers or other additives. Adjustment of the strength of the shell may be modified, for example, by the internal pressure within the microparticles.

Precise acoustical characteristics of the microbubble may be achieved by control of the shell mechanical properties, thickness, as well as narrow size distribution. The microbubbles may be ruptured by ultrasonic energy to release gases trapped within the microparticles into the blood stream. By appropriately adjusting the mechanical properties, the microbubbles may be made to remain stable to threshold diagnostic imaging power, while being rupturable by an increase in power and/or by being exposed to its resonant frequency. The resonant frequency can be made to be within the range of transmitted frequencies of diagnostic body imaging systems or can be a harmonic of such frequencies. During the formulation process the microparticles may be prepared to contain various gases, including blood soluble or blood insoluble gases. It is a feature of the invention that microparticle compositions may be made having a resonant frequency greater or equal to 2 MHz, and typically greater or equal to 5 MHz.

The bi-layer microbubbles may be prepared by an emulsification process to control the sequential interfacial deposition of shell materials. See, Example III. Due to the amphiphilicity of the material forming the outer layer, stable oil/water emulsions may be prepared having an inner phase to outer phase ratio approaching 3:1, without phase inversion, which can be dispersable in water to form stable organic phase droplets without the need for surfactants, viscosity enhancers or high shear rates.

B. Microbubbles Having Controlled Fragility

Microbubble populations having a controlled fragility have been characterized by a uniform wall thickness to diameter ratio that defines a discrete threshold power intensity value of ultrasonic energy where microbubble rupture in the population occurs. A controlled fragility microbubble population having a constant diameter to wall thickness ratio can be produced by an emulsion solvent evaporation process. See, Example IV.

The controlled fragility characteristic of a microbubble population is derived from the provision that the wall thickness of the microbubble is linearly related to its diameter. That is, for a given microbubble population the ratio of wall thickness to diameter for each microbubble within the population is a constant. When internalized into a biological cell, the microbubble ultrasound contrast agent would exhibit essentially an equivalent resistance to the stresses imparted by the hydrostatic and acoustic forces present in the extracellular ultrasound imaging environment. It can be shown mathematically that the strength, that is resistance to a hoop stress, of a thin-walled hollow sphere is a function of the diameter of the sphere and the thickness of its wall. Further, this relationship is linearly proportional with diameter and inversely proportional with thickness. Thus, for a given applied pressure, if the ratio of thickness to diameter is constant, then the hoop stress on the sphere wall remains constant irrespective of diameter. An ultrasonic contrast agent including a spectrum of microbubbles all having the same wall thickness to diameter ratio would therefore exhibit essentially an equivalent resistance to the stresses imparted by the hydrostatic and acoustic forces present in the ultrasonic imaging environment.

Microbubble fragility may be measured by a mechanical index (MI) identified on all modern ultrasound scanners as a measure of the maximal rarefactional (negative) pressure in the propagated ultrasound field. If the MI were increased systematically from a transducer focused on a plethora of microbubbles possessing a constant h/d ratio, there would be no breakage until the rarefactional pressure of $P_{max}$ was reached. The value of MI when this event is achieved is referred to as the critical MI ($MI_{crit}$). Microbubbles continue to break for all values above this value of $MI_{crit}$. However, the rate of destruction increases as the power level rises. If the h/d ratio is not constant, then there is not a clean initiation of agent destruction. Failure begins at near zero MI and the rate of destruction increases thereafter. Thus, there is no critical MI, there is no controlled fragility. For use in an ultrasonic imaging system, the inner layer wall thickness to diameter ratio can be varied to provide varying thresholds thereby delaying or accelerating rupture.

In regards to a bi-layer microbubble, the mechanical properties of the inner layer such as ultimate elongation, modulus, stress at failure and fatigue properties can be tailored by material selection. Selection of the appropriate mechanical strength of the inner layer allows imaging at conditions which do not necessarily trigger microbubble rupture, but rupture may be triggered during imaging by altering the ultrasound characteristics. These characteristics are useful for controlling and localizing specific and localized imaging.

C. Polymer Composition Comparison Testbed

The present polymer contrast microbubble was compared to other polymer compositions using a dual transducer system that transmits at 2.5 MHz with a 10 cycle tone burst. The system receives the reflected waves at a broadband center frequency of 5 MHz, broadband. Transmission power may be calibrated and recalibrated at the users discretion. See, FIGS. 2-9.

Figure 10:
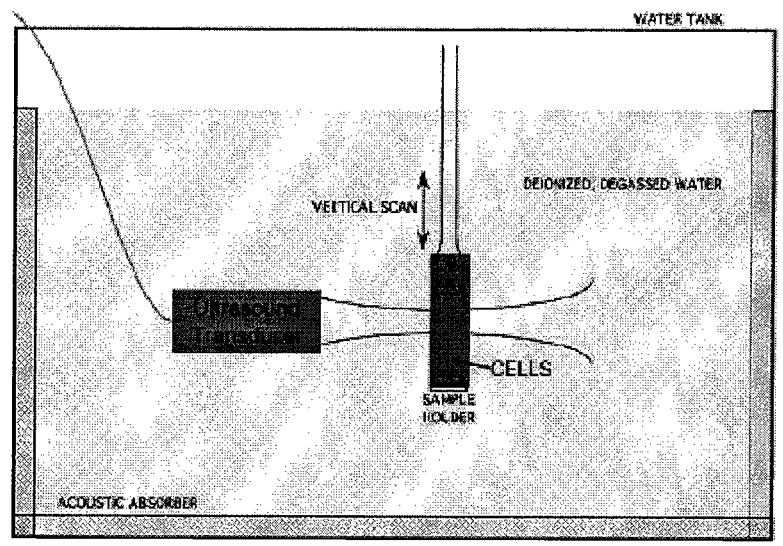
FIG. 10 presents one embodiment of an in vitro imaging platform to determine the acoustic characteristics of polymer contrast microbubbles. Transducer (i.e., for example, an Siemens AcusonSequoia 512 Imaging System).

The testbed comprised an in vitro imaging system comprising a sample holder that is scanned by a transducer immersed within a container of deionized, degassed water. See, FIG. 10. The data was collected using a Siemens AcusonSequoia 512 Imaging System set at one of three imaging modes: i) CPS7.0 Imaging Mode utilizing a transmission frequency of 7 MHz at MI=0.3, and MI=1.9; ii) Harmonic 14.0 imaging mode utilizing a transmission frequency of 7 MHz at MI=0.3, and MI=1.9; and iii) a 8 MHz Linear Imaging Mode utilizing a transmission frequency of 8 MHz at MI=0.3 and MI=1.0.

D. Comparison of In Vitro Compositions

Figure 11:
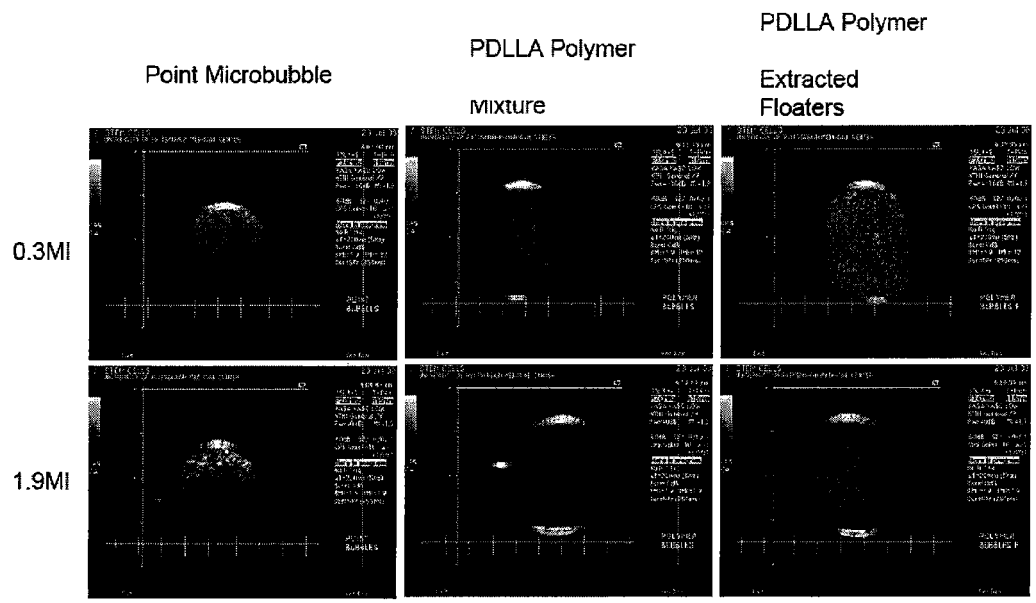
FIG. 11 presents exemplary data showing an imaging comparison of three different compositions: i) bi-layer polymer contrast microbubbles (Point Biomedical); ii) conventional PDLLA microparticles; and iii) conventional PDLLA floating microparticles, measured at two different MI's (0.3 and 1.9) using a CPS7.0 Imaging Mode.
Figure 12:
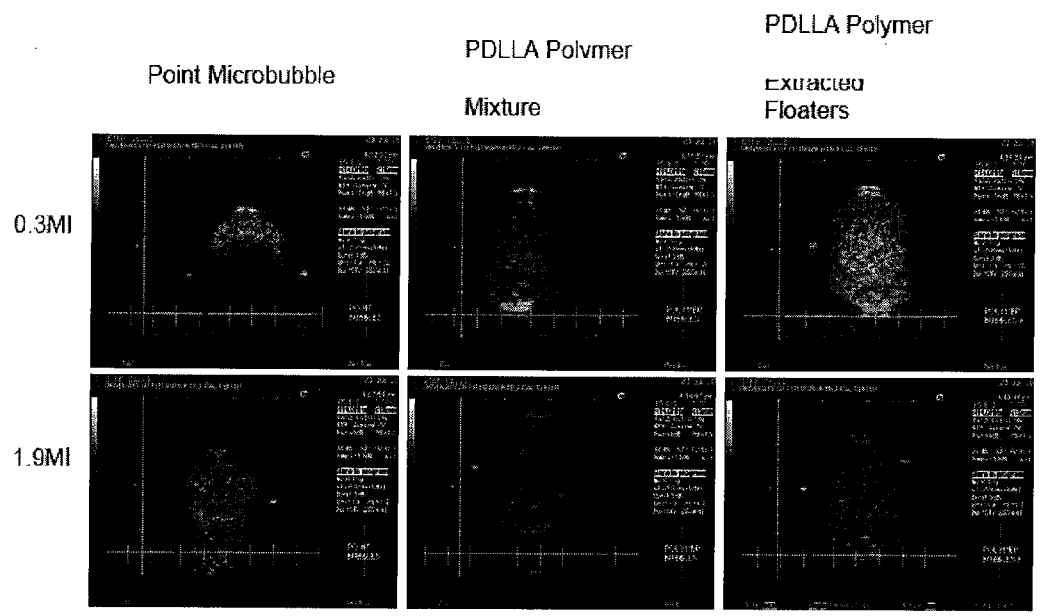
FIG. 12 presents exemplary data showing an imaging comparison of three different compositions: i) bi-layer polymer contrast microbubbles (Point Biomedical); ii) conventional PDLLA microparticles; and iii) conventional PDLLA floating microparticles, measured at two different MI's (0.3 and 1.9) using a Harmonic 14.0 Imaging Mode.
Figure 13:
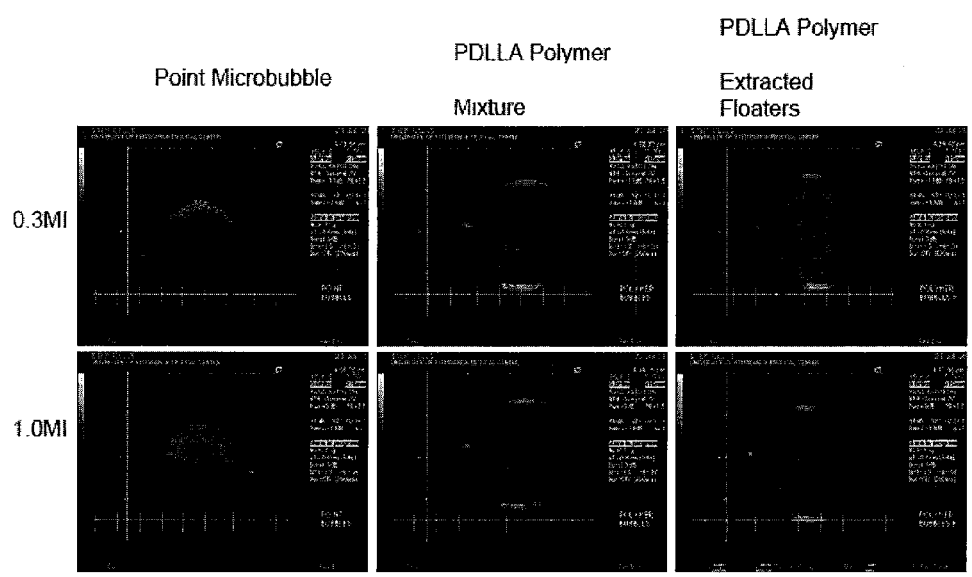
FIG. 13 presents exemplary data showing an imaging comparison of three different compositions: i) bi-layer polymer contrast microbubbles (Point Biomedical); ii) conventional PDLLA microparticles; and iii) conventional PDLLA floating microparticles, measured at two different MI's (0.3 and 1.0) using an 8 MHz Linear Imaging Mode.

Three different polymer compositions were compared at each of these mode settings; i) a bil-layer polymer contrast microbubble; ii) a PDLLA polymer microparticle; and iii) floating PDLLA polymer microparticles. The polymer contrast microbubbles produce a stronger signal for all imaging modes and MI settings than the PDLLA polymer microparticles. Further, the floating PDLLA microparticles extracted from the PDLLA microparticle mixture also produce a stronger signal than the PDLLA polymer microparticles. Polymer contrast microbubble signal saturation occurred at: i) MI=0.3 in the Harmonic 14.0 Imaging mode; ii) MI=0.3 and 1.0 in the 8 MHz Linear Imaging Mode; and iii) i to some degree at MI=0.3 and 1.9 in the CPS7.0 Imaging Mode. See, FIGS. 11-13.

E. Comparison of Internalized Polymer Compositions

Figure 14:
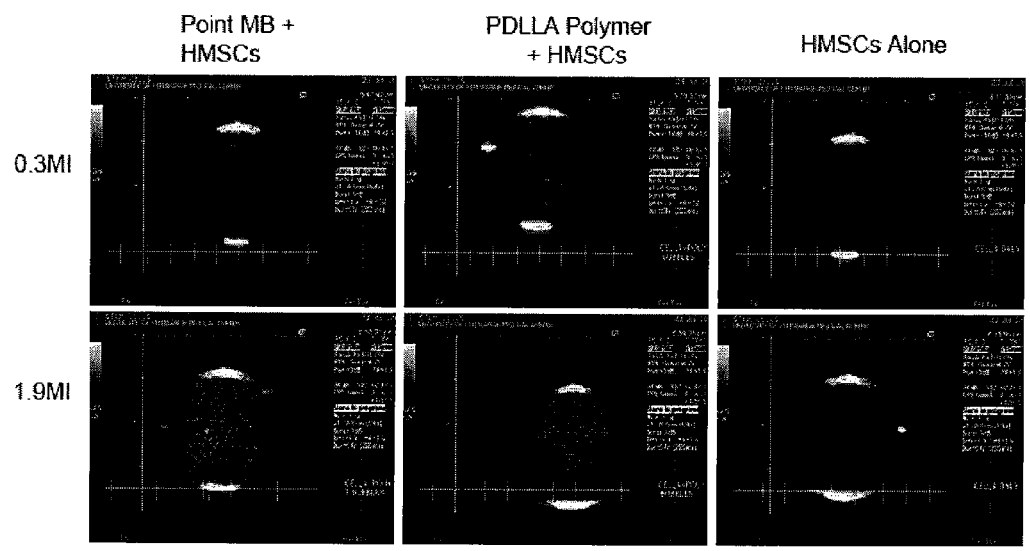
FIG. 14 presents exemplary data showing an imaging comparison of three different human mesenchymal stem cell compositions: i) internalized bi-layer polymer contrast microbubbles (Point Biomedical); ii) internalized conventional PDLLA microparticles; and iii) human mesenchymal stem cells alone, measured at two different MI's (0.3 and 1.9) using a CPS7.0 Imaging Mode.
Figure 15:
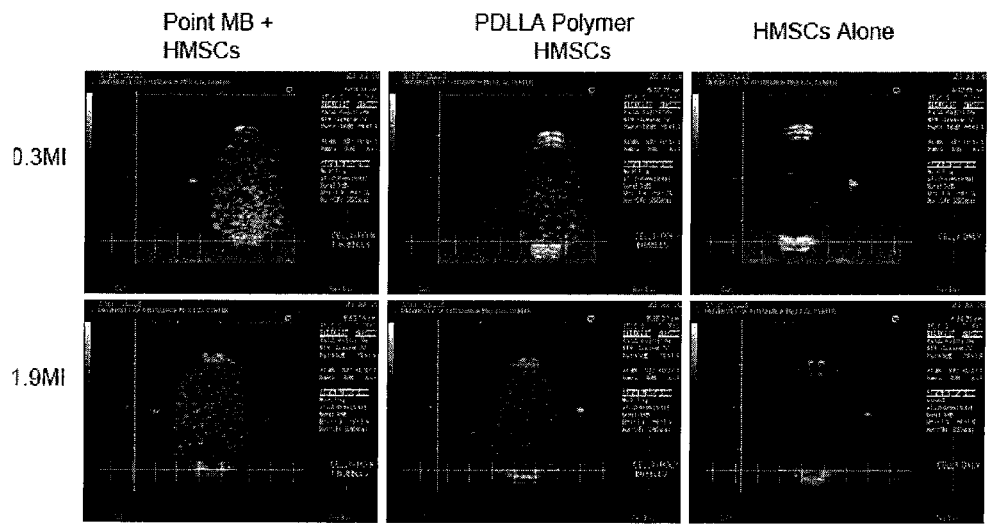
FIG. 15 presents exemplary data showing an imaging comparison of three different human mesenchymal stem cell compositions: i) internalized bi-layer polymer contrast microbubbles (Point Biomedical); ii) internalized conventional PDLLA microparticles; and iii) human mesenchymal stem cells alone, measured at two different MI's (0.3 and 1.9) using a Harmonic 14.0 Imaging Mode.
Figure 16:
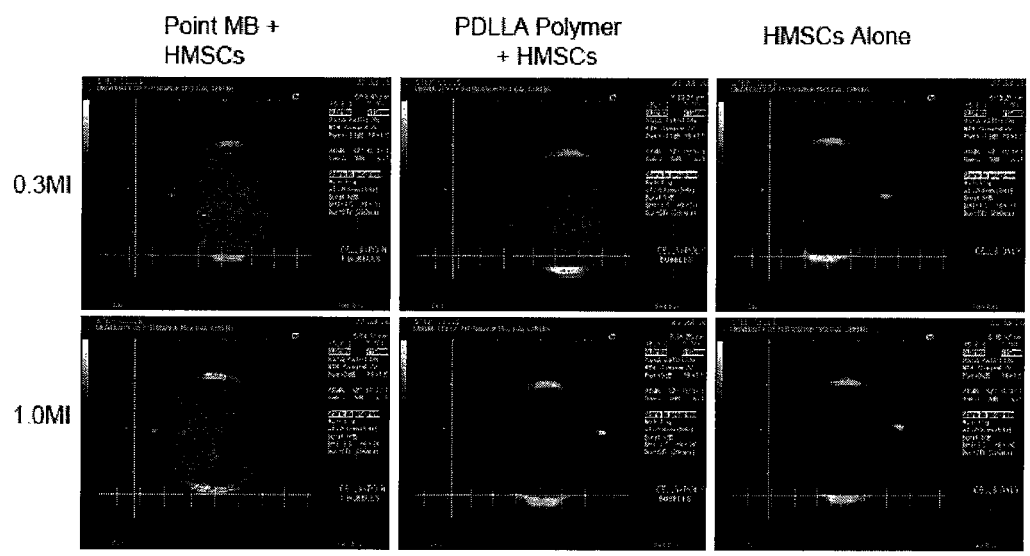
FIG. 16 presents exemplary data showing an imaging comparison of three different human mesenchymal stem cell compositions: i) internalized bi-layer polymer contrast microbubbles (Point Biomedical); ii) internalized conventional PDLLA microparticles; and iii) human mesenchymal stem cells alone, measured at two different MI's (0.3 and 1.9) using an 8 MHz Linear Imaging Mode.

Human Mesenchymal Stem Cell (hMSCs) which have internalized polymer contrast microbubbles produce a significantly stronger signal than the hMSCs alone for all imaging modes and MI settings. hMSCs which have internalized PDLLA polymer microparticles produce a stronger signal than the hMSCs alone for all imaging modes and MI settings, but less so than the cells which internalize polymer contrast microbubbles. A weaker signal was observed from the PDLLA polymer microparticles+hMSCs in the 8 MHz linear imaging mode at MI=1.0. The signal from hMSCs alone in Harmonic 14.0 imaging mode at MI=1.9 is likely a linear reflection of a distorted 7 MHz signal, which includes a 14 MHz component, as delivered by the tested system. See, FIGS. 14-16.

F. CPS7.0 Imaging Mode Acoustic Video Intensity Summary

Figure 17:
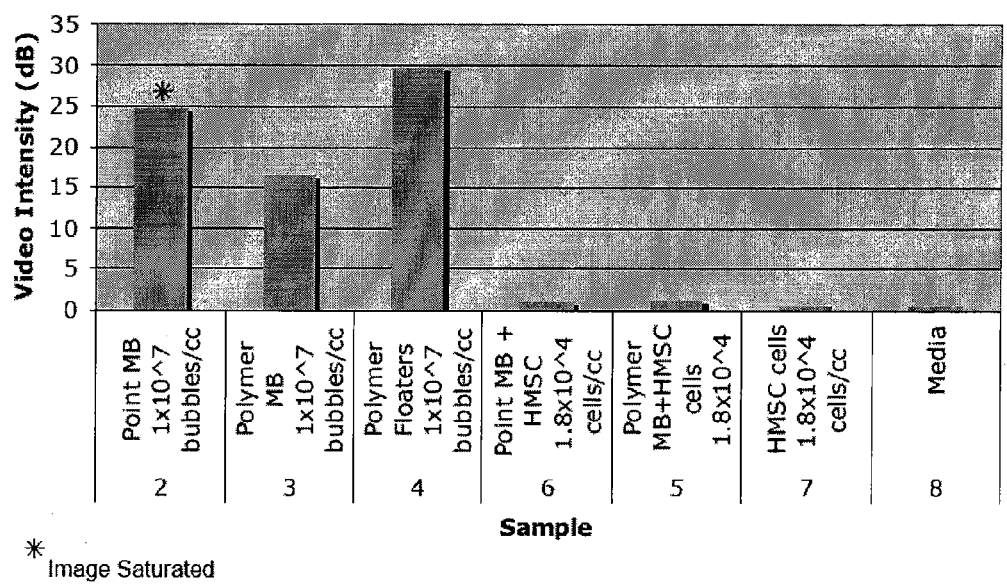
FIG. 17 presents exemplary summary data of Acoustic Video Intensity (dB) for various microbubble compositions using a CPS7 Imaging Mode at MI=0.3.
Figure 18:
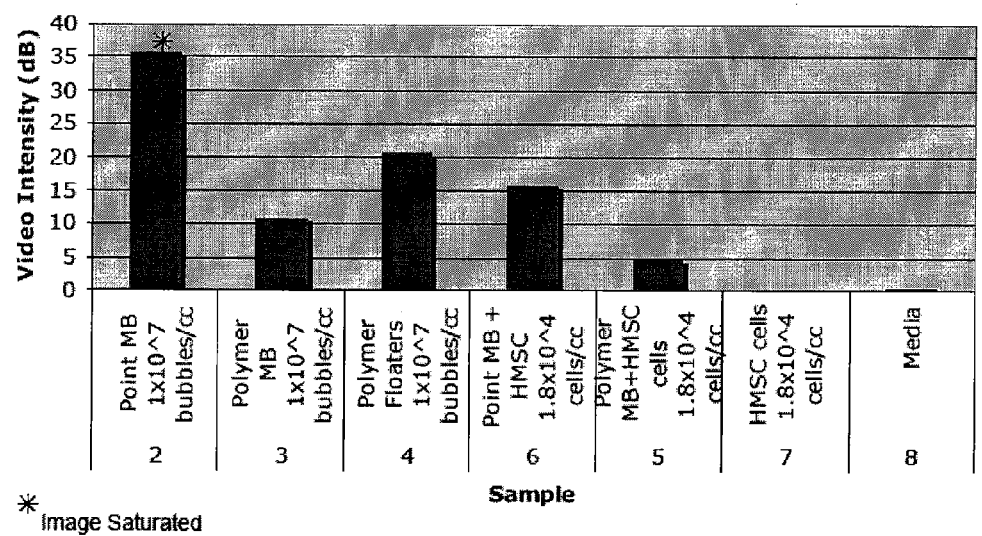
FIG. 18 presents exemplary summary data of Acoustic Video Intensity (dB) for various microbubble compositions using a CPS7 Imaging Mode at MI=1.9.

Signal saturation occurs for the polymer contrast microbubbles at MI=0.3. This effect is present but reduced at MI=1.9 due to the effect of the radiation force pushing the microbubbles away from the near interface. After accounting for attenuation, the polymer contrast microbubbles produce a stronger signal than the PDLLA microparticles and the floating PDLLA microparticles. The floating PDLLA microparticle mixture produces a stronger signal than the whole PDLLA microparticle mixture. Signal from the hMSCs with internalized microbubbles increases at MI=1.9 and are well above the signal from the hMSCs alone. See, FIG. 17 and FIG. 18.

G. Harmonic 14 Imaging Mode Acoustic Video Intensity Summary

Figure 19:
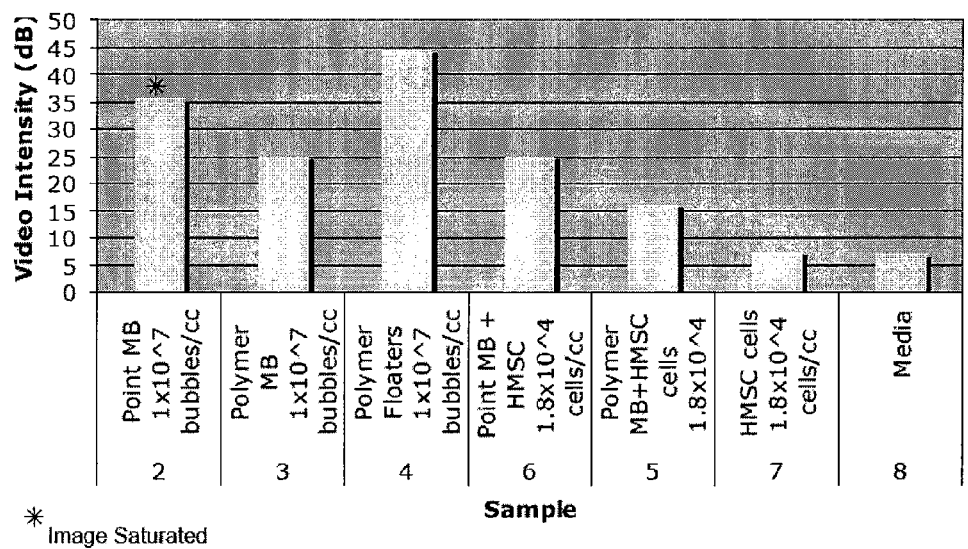
FIG. 19 presents exemplary summary data of Acoustic Video Intensity (dB) for various microbubble compositions using a Harmonic 14.0 Imaging Mode at MI=0.3.
Figure 20:
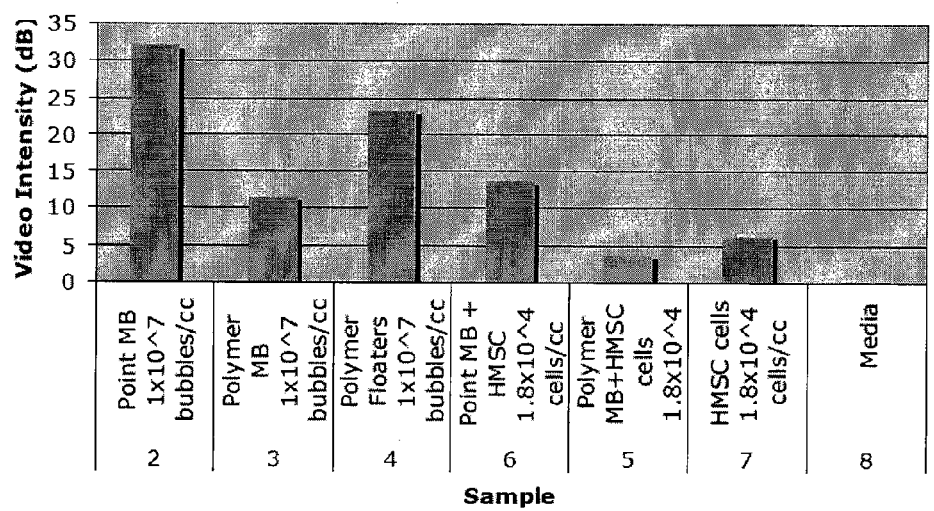
FIG. 20 presents exemplary summary data of Acoustic Video Intensity (dB) for various microbubble compositions using a Harmonic 14.0 Imaging Mode at MI=1.9.

Signal saturation occurs for the polymer contrast microbubbles at MI=0.3. This effect is reduced at MI=1.9 due to the effect of the radiation force pushing the microbubbles away from the near interface. After accounting for attenuation, the polymer contrast microbubbles produce a stronger signal than the PDLLA microparticles and the floating PDLLA microparticles. The floating portion of the PDLLA microparticle mixture produces a stronger signal than the whole PDLLA microparticle. See, FIG. 19 and FIG. 20.

H. 8 MHz Linear Imaging Mode Acoustic Video Intensity Summary

Figure 21:
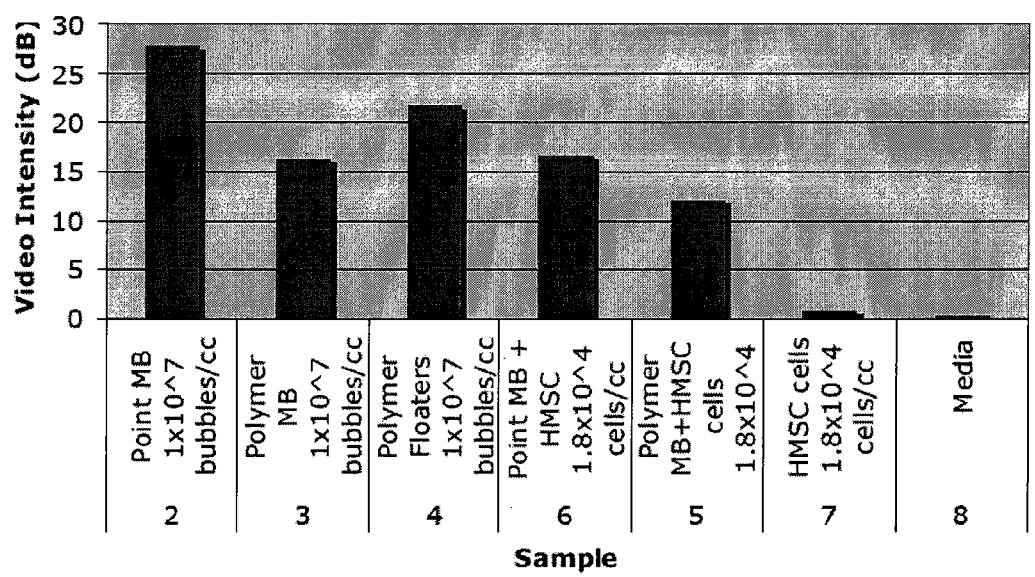
FIG. 21 presents exemplary summary data of Acoustic Video Intensity (dB) for various microbubble compositions using an 8 MHz Linear Imaging Mode at MI=0.3.
Figure 22:
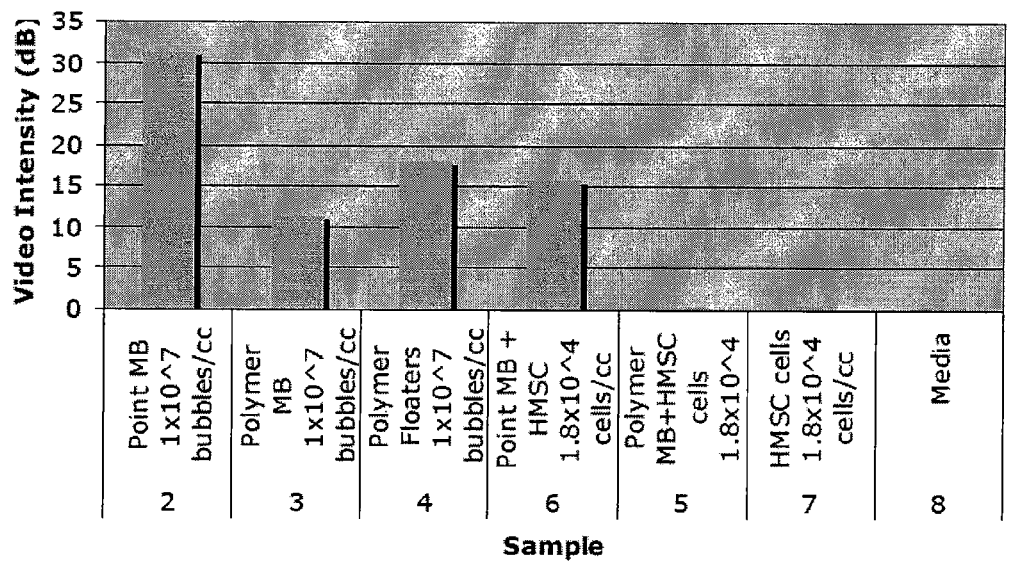
FIG. 22 presents exemplary summary data of Acoustic Video Intensity (dB) for various microbubble compositions using an 8 MHz Linear Imaging Mode at MI=1.0.

The signal for all samples is improved at MI=0.3. However, the polymer contrast microbubbles produce a stronger signal than either the total PDLLA microparticle mixture and the floating PDLLA microparticle mixture. See, FIG. 21 and FIG. 22.

I. Trend Data: CPS7, Harmonic 14.0 & 8 MHz Linear Modes

Figure 23:
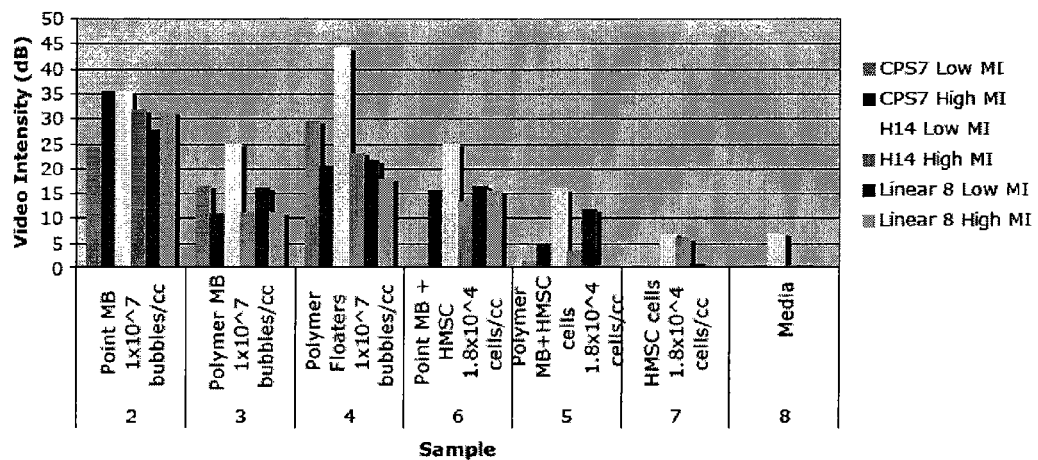
FIG. 23 presents exemplary summary data of all acoustic video intensity data presented in FIGS. 11-22.

In general, the acoustic signal tends to improve at MI=0.3, with the exception of CPS7. One explanation is that the CPS7 mode is known to suppresses background signal from cells and media better than either Harmonic 14.0 and Linear 8 MHz modes. hMSCs which internalize polymer contrast microbubbles produce a better signal than those which internalize PLLA microparticles for all imaging modes and powers, with the exception of CPS7 at MI=0.3. See, FIG. 23.

J. Maintaining Microbubble Integrity

In one embodiment, a polymer contrast microbubble as described herein is formulated to resist the loss of acoustically active gas and/or shell destruction upon uptake by a biological cell. Although it is not necessary to understand the mechanism of an invention, it is believed that if a tissue reparative effect requires a biological cell to persist for a limited time period (as opposed to indefinitely), then the presently disclosed microbubbles need to 'survive' only for a limited period of time. The data presented herein, demonstrated the retention of acoustic activity of internalized microbubbles up to at least 48 hrs after creation. See, FIGS. 29-32.

II. Conventional In Vivo Biological Cell Imaging Systems

It has been previously believed that successful in vivo imaging requires that a contrast agent associated with a biological cell exerts an "effect size" sufficient for detection by imaging hardware. Although the most attractive contrast agents for tracking are endogenous ones (i.e., for example, stem cells comprising naturally occurring components), their effect size is extremely small. However, exogenous contrast agents may have a large and controllable effect size thereby imparting additional clinical relevance because many preclinical small animal studies in the field of stem cell tracking are not translatable to clinical practice.

A. Characteristics of an Ideal Imaging Technology

Historically, approximately, eight (8) characteristics have been offered to describe an ideal imaging technology for biological cell tracking. These characteristics included; i) biocompatibility, safety, and nontoxicity; ii) no genetic modification or perturbations; iii) single-cell detection at any anatomic location; iv) quantification of cell number; v) minimal or no dilution with cell division; iv) minimal or no transfer of contrast agent to non-tracked cells; vii) noninvasive imaging in the living subject over months to years; and viii) no requirement for injectable contrast agent.

While clinically useful exogenous contrast agents are biocompatible, safe, and nontoxic, some currently available contrast agents genetically modify the biological cell or perturbate its genetic program. Several conventional imaging techniques, such as enzymatic conversion of an injected substrate and receptor-based binding, require stable integration of transgenes. This strategy may be combined with genetic manipulation of cell populations to enhance the viability, differentiation, and coupling of these cells with the myocardium. These types of manipulations add significant cost, regulatory roadblocks, and the potential to induce genetic abnormalities, including uncontrolled growth and malignancy. Hacein-Bey-Abina et al., "LMO2-associated clonal T cell proliferation in two patients after gene therapy for SCID-X1" Science 302:415-419 (2003). Although exogenous genes may not be diluted by cell division and have the potential to induce cell survival or suicide on demand, it is unclear at present if the extra step of genetic manipulation will become routine in human clinical stem cell trials. Klatzmann D, Valery C A, Bensimon G, et al. "A phase I/II study of herpes simplex virus type 1 thymidine kinase "suicide" gene therapy for recurrent glioblastoma. Study Group on Gene Therapy for Glioblastoma" *Hum Gene Ther.* 9:2595-2604 (1998).

Ideally, imaging technology used for stem cell tracking would have single-cell sensitivity and would permit quantification of exact cell numbers at any anatomic location. Single-cell sensitivity is especially important in a new field such as that of stem cells because the pattern of migration of stem cells, even after local injection, is unknown, and there is a distinct possibility that single stem cells scattered diffusely throughout the body might be effective therapeutics for certain disease states Regardless of the level of sensitivity finally achieved, quantification of cell number can be especially difficult when we consider the effects of contrast agent dilution during cell division, the propensity of some contrast agents to be transferred to nonstem cells, and certain technical limitations (discussed below). The criteria of ultra-high high sensitivity, quantification, and full-body scanning render many clinically available imaging modalities inadequate at present.

The ideal imaging technology would permit tracking of injected biological cells for months to years because clinical trials undoubtedly will require long-term follow-up of tissue function or host survival. Finally, injectable contrast agents, such as enzyme substrates, add complexity and cost to stem cell-tracking procedures. At present, no imaging technology fulfills the 8 criteria presented above, although some come close.

B. Comparisons of Currently Available Imaging Techniques

There are a variety of clinically used imaging techniques utilized as of the present day. The known disadvantages of these various imaging modalities have been reported. See, Table 1, Frangioni et al., "In Vivo Tracking of Stem Cells for Clinical Trials in Cardiovascular Disease" *Circulation* 110: 3378-3383 (2004).

TABLE 1

Disadvantages Of Conventional Contrast Agents and Detectors for In Vivo Cell Tracking

| Modality | Contrast Agent | Advantages | Disadvantages |
| --- | --- | --- | --- |
| Plain films | High-density/high-atomic number materials (e.g., iodine, gadolinium) | Inexpensive, fast, readily available, few clinical contraindications | Requires molar concentrations of contrast agent, 2D projections only, quantification difficult, ionizing radiation |
| Computed tomography | High-density/high-atomic number materials (e.g., iodine, gadolinium) | Readily available, 3D, full-body scanning | Requires molar concentrations of contrast agent, artifacts from bone and cardiac devices, ionizing radiation |
| Optical: bioluminescence | Luciferase substrates | Sensitive, no ionizing radiation | Requires genetic modification of stem cell and intravenous injection of contrast agent, limited to small animal use |
| Optical: fluorescence | Near-infrared fluorophores | Sensitive, no ionizing radiation, fast, ex vivo single-cell histological detection | Limited to small animal or intraoperative use, dilution of contrast agent with cell division, potential transfer of contrast agent to nonstem cells |
| Ultrasound/echocardiography | Microbubbles of various materials | Readily available, fast, no ionizing radiation, potential in vivo single-cell detection | Limited anatomic access, relatively low resolution, quantification difficult, dilution of contrast agent with cell division, potential transfer to nonstem cell |
| SPECT | High-energy gamma emitters (e.g., $^{99m}$Tc, $^{111}$In) | Sensitive, 3D full-body scanning, no dilution of effect size with cell division (transgenic approaches) | Requires genetic modification of stem cell and/or intravenous injection of contrast agent, ionizing radiation, quantification can be difficult |
| PET | High-energy positron emitters (e.g., $^{18}$F, $^{124}$I) | Sensitive, 3D full-body scanning, no dilution of effect size with cell division (transgenic approaches), quantification possible | Requires genetic modification of stem cell and/or intravenous injection of contrast agent, ionizing radiation, not readily available |
| MRI | Lanthanides (e.g., gadolinium), superparamagnetic iron-oxide nanoparticles (e.g., MIONs) | 3D full-body scanning, no ionizing radiation, quantification possible but can be difficult | Contraindicated with many cardiac devices, some contrast agents are insensitive, dilution of contrast agent with cell division, potential transfer to non-stem cells |
| MRI/fluorescence | Fluorophore-labeled T1 or T2/T2* agents | Intraoperative image-guided delivery of stem cells, 3D full-body scanning, no ionizing radiation, quantification possible but can be difficult, ex vivo single-cell detection | Contraindicated with many cardiac devices, some contrast agents are insensitive, dilution of contrast agents with cell division, potential transfer to nonstem cells |
| MRI/fluorescence/ultrasound | Fluorophore, perfluorocarbon, and $Gd^{3+}$-labeled liposomes | Intraoperative image-guided delivery of stem cells, 3D full-body scanning, no ionizing radiation, quantification possible but can be difficult, potential in vivo and ex vivo single-cell detection | Contraindicated with many cardiac devices, dilution of contrast agents with cell division, potential transfer to nonstem cells, unknown effects on cellular physiology |

1. X-Ray Methods

Plain films and computed tomography (CT) are the most readily available clinical imaging modalities. Unfortunately, contrast generation requires extremely high concentrations of high-density/high-atomic number materials such as iodine, gadolinium, or metals. To render a stem cell or collection of stem cells visible by using even a solid metal, the volume of metal associated with the cell volume must be equal to or greater than the inverse of its density. For example, it would take approximately one eighth of the cell volume in solid iron to generate a signal above background during CT scanning. Such contrast is difficult to achieve, rendering x-ray-based methods unlikely to play a direct role in stem cell tracking at the present time.

2. Optical Imaging

Two complementary optical imaging methods, bioluminescence and fluorescence, can be used for stem cell tracking. Bioluminescence utilizes light generated by the enzyme luciferase to detect cells in vivo. Several animal studies performed in mice and rats utilized bioluminescence to track the distribution and engraftment of stem cells in vivo. Wang et al., "Dynamic tracking of human hematopoietic stem cell engraftment using in vivo bioluminescence imaging" *Blood* 102:3478-3482 (2003); Tang et al., "In vivo tracking of neural progenitor cell migration to glioblastomas" *Hum Gene Ther.* 14:1247-1254 (2003); Cao et al., "Shifting foci of hematopoiesis during reconstitution from single stem cells" *Proc Natl Acad Sci USA.* 101:221-226 (2004); and Wu et al., "Molecular imaging of cardiac cell transplantation in living animals using optical bioluminescence and positron emission tomography" *Circulation* 108:1302-1305 (2003). Unfortunately, luciferase genes and substrates described to date generate only visible (400 to 700 nm) light, which has very high absorption and scatter in living tissue. This precludes use of the technique in animals larger than rats, and even in mice false-negative scanning can occur, dependent on cell depth. Rice et al., "In vivo imaging of light-emitting probes" *J Biomed Opt.* 6:432-440 (2001). Bioluminescence also requires the stable expression of nonhuman genes, and the injection of high concentrations of potentially immunogenic, nonhuman substrates, such as luciferin and coelenterazine. It is therefore unlikely that this technique can be used clinically.

Fluorescence imaging utilizes organic (e.g., green fluorescent protein, small-molecule polymethines) or organic/inorganic hybrids (e.g., quantum dots) as exogenous contrast agents for in vivo imaging. Frangioni J V., "In vivo near-infrared fluorescence imaging" *Curr Opin Chem Biol.* 7:626-634 (2003). Because of high photon absorption and scatter at visible wavelengths, only near-infrared (NIR) (700 to 1000 nm) fluorophores have clinical potential. The major problem with NIR fluorescence is that even with tomographic imaging methods, detection is limited to only 4 to 10 cm of tissue. Ntziachristos et al., "Fluorescence imaging with near-infrared light: new technological advances that enable in vivo molecular imaging" *Eur Radiol.* 13:195-208 (2003); and Sevick-Muraca et al., "Fluorescence-enhanced, near infrared diagnostic imaging with contrast agents" *Curr Opin Chem Biol.* 6:642-650 (2002). Hence, clinical use of NIR fluorescence likely will be limited to near-surface applications, such as intraoperative imaging. Reynolds et al., Imaging of spontaneous canine mammary tumors using fluorescent contrast agents. Photochem Photobiol. 1999; 70:87-94; Nakayama et al., "Functional near-infrared fluorescence imaging for cardiac surgery and targeted gene therapy" *Molecular Imaging* 1:365-377 (2002); and Kim et al., "Near-infrared fluorescent type II quantum dots for sentinel lymph node mapping" *Nat Biotechnol.* 22:93-97 (2004). Further disadvantages of NIR fluorescence include the dilution of the agent with each cell division and the possibility of uptake by nonstem cells after stem cell death.

3. Ultrasound

Because cardiologists likely will conduct the majority of clinical studies of stem cells in cardiovascular applications, tracking by echocardiography would be extremely convenient. Contrast for echocardiography is generated by acoustic interfaces such as water/gas (e.g., microbubbles, perfluorocarbons). Although a single unit of contrast is on the order of 0.25 to 1 μm in diameter, the generated acoustic perturbation appears much larger. Echocardiography therefore has the potential to detect a single cell loaded with a single unit of contrast. Klibanov et al. "Detection of individual microbubbles of ultrasound contrast agents: imaging of free-floating and targeted bubbles" *Invest Radiol.* 39:187-195 (2004). Nevertheless, methods to accumulate contrast intracellularly are not yet robust, and effects on cell motility, etc, are not known. An additional problem is that echogenic contrast agents cast an acoustic "shadow" below the first unit of contrast detected, thus precluding accurate quantification of cell number. Such contrast agents are subject to dilution during cell division and transfer to nonstem cells after cell death. Finally, spatial resolution of ultrasound is limited, and many anatomic sites are inaccessible.

4. Single-Photon Emission Computed Tomography

High-energy gamma rays emitted by radioactive atoms such as $^{99m}$Tc, $^{111}$In, and $^{123}$I are detected by rotating a collimated gamma camera around the subject and reconstructing a 3-dimensional image. Three strategies for in vivo stem cell detection have been described: i) direct loading with a radiometal (Gao et al., "The dynamic in vivo distribution of bone marrow-derived mesenchymal stem cells after infusion" *Cells Tissues Organs* 169:12-20 (2001); Chin et al., "$^{111}$In oxine labeled mesenchymal stem cell SPECT after intravenous administration in myocardial infarction" *Nucl Med Commun.* 24:1149-1154 (2003); and Barbash et al., "Systemic delivery of bone marrow-derived mesenchymal stem cells to the infarcted myocardium: feasibility, cell migration, and body distribution" *Circulation* 108: 863-868 (2003); and Archer et al., "Assessment of the tissue distribution of transplanted human endothelial progenitor cells by radioactive labeling" *Circulation* 107:2134-2139 (2003); ii) enzymatic conversion and retention of a radioactive substrate (Gambhir et al., "Imaging transgene expression with radionuclide imaging technologies" *Neoplasia* 2:118-138 (2000)); and iii) receptor-mediated binding. Gambhir et al., "Imaging transgene expression with radionuclide imaging technologies" *Neoplasia* 2:118-138 (2000); and Simonova et al., "Engineering of technetium-99m-binding artificial receptors for imaging gene expression" *J Gene Med.* 5:1056-1066 (2003).

Direct loading is problematic given the tradeoff between half-life and long-term exposure to ionizing radiation and given the possibility of transfer of the radiometal from stem cells to nonstem cells.

Enzymatic conversion/retention has been used for both single-photon emission CT (SPECT) and positron emission tomography (PET) (see below) substrates. The disadvantages of this strategy include the need to genetically manipulate the stem cell ex vivo and the need to administer a substrate intravenously for each imaging session.

Receptor-mediated targeting requires stable expression of a receptor not found elsewhere in the body and intravenous injection of a radioactive receptor ligand.

5. Positron Emission Tomography

PET utilizes coincident detection of 2 anti-parallel 511-keV gamma rays emitted after positron annihilation.

Tradeoffs exist between the higher energy of the photons, coincident detection, and detector efficiency, but overall, PET has a higher sensitivity than SPECT and permits more accurate quantification of cell number. Although SPECT can be used for stem cell tracking with PET, the most advanced by far is the stable integration of a mutant herpes simplex type 1 thymidine kinase (TK) into stem cells and periodic intravenous injection of the TK substrate 18FHBG. Wu et al., "Molecular imaging of cardiac cell transplantation in living animals using optical bioluminescence and positron emission tomography" *Circulation* 108:1302-1305 (2003). Although it permits tracking and quantification of stem cells over the course of months, this strategy requires genetic manipulation of the stem cells, an infrastructure for $^{18}F$ chemistry, a PET scanner, and radiation exposure (albeit intermittent) to the stem cells and subject.

Additional caveats for SPECT- and PET-based tracking of stem cells include nonspecific uptake of the radiotracer by normal tissue, relatively low efficiency of collimated SPECT cameras, and photon attenuation by tissue. Although tissue photon attenuation can be corrected in some cases, for example by employing hybrid nuclear medicine/CT systems, it reduces sensitivity, and prevents accurate quantification of stem cell number. Chin et al., "$^{111}$In oxine labeled mesenchymal stem cell SPECT after intravenous administration in myocardial infarction" *Nucl Med Commun* 24:1149-1154 (2003). Whether used for attenuation correction or not, hybrid CT systems have the major advantage that they permit coregistration of anatomic (CT) and physiological (SPECT or PET) images.

Another, and often overlooked, issue is the inherent limits of radioactive methods for stem cell detection. A typical patient dose of 10 to 20 mCi is equivalent to only 3.5 to $7 \times 10^{12}$ radioactive molecules of contrast agent. In typical clinical nuclear medicine imaging, $\sim 10^9$ radioactive molecules per milliliter are required to generate detectable signal above background To detect a single stem cell, ~0.01% of the injected dose would have to be concentrated in/on the cell, which is a formidable technical challenge.

6. Magnetic Resonance Imaging

Given its extraordinary 3-dimensional capabilities and high safety profile, magnetic resonance imaging (MRI) is the imaging modality used by most research studies to track stem cells in vivo. At this point in time, MRI imaging techniques can be divided into those generating primarily T1 contrast and those generating primarily T2/T2* contrast.

T1 contrast agents are those that utilize the lanthanide gadolinium ($Gd^{3+}$), which changes the relaxivity of protons from associated water molecules and increases the signal on T1-weighted images. Unfortunately, with presently available field strengths, $Gd^{3+}$-based contrast requires 50- to 500-μmol/L concentrations of low-molecular-weight $Gd^{3+}$-containing molecules or attachment to bulky scaffolds such as dendrimers and dextrans to increase the T1 effect. It has been reported, however, that $Gd^{3+}$-containing scaffolds, loaded via pino/endocytosis into stem cells, permit tracking for up to 6 weeks. Bulte et al., "Magnetodendrimers allow endosomal magnetic labeling and in vivo tracking of stem cells" *Nat Biotechnol.* 19:1141-1147 (2001); Bulte et al., "Monitoring stem cell therapy in vivo using magnetodendrimers as a new class of cellular MR contrast agents" *Acad Radiol.* 9:S332-S335 (2002); and Modo et al., "Tracking transplanted stem cell migration using bifunctional, contrast agent-enhanced, magnetic resonance imaging" *Neuroimage* 17:803-811 (2002).

T2/T2* contrast is by far the most widely used technique for stem cell imaging studies using MRI. It was observed in the early 1990s that superparamagnetic iron oxide nanoparticles (also known as monocrystalline iron oxide nanocrystals [MIONs], ultrasmall superparamagnetic iron oxide [US-PIOs]) congeal in endosomes after endocytosis, resulting in magnification of their susceptibility effects. More recent formulations utilize Tat peptides to improve cell loading, which can now be accomplished in ~1 hour. Josephson et al., "High-efficiency intracellular magnetic labeling with novel superparamagnetic-Tat peptide conjugates" *Bioconjug Chem.* 10:186-191 (1999); and Lewin et al., "Tat peptide-derivatized magnetic nanoparticles allow in vivo tracking and recovery of progenitor cells" *Nat Biotechnol.* 18:410-414 (2000). Because of the magnification effect, MIONs can be used to track extremely small numbers of stem cells, on the order of thousands, at high field strengths, for up to several weeks. Daldrup-Link et al., Targeting of hematopoietic progenitor cells with MR contrast agents" *Radiology* 228:760-767 (2003).

T2/T2* contrast agents and their technical improvements already have been applied to stem cell tracking in vivo. Lewin et al., "Tat peptide-derivatized magnetic nanoparticles allow in vivo tracking and recovery of progenitor cells" *Nat Biotechnol.* 18:410-414 (2000); Frank et al., "Clinically applicable labeling of mammalian and stem cells by combining superparamagnetic iron oxides and transfection agents" *Radiology* 228:480-487 (2003);. van den Bos et al., "Improved efficacy of stem cell labeling for magnetic resonance imaging studies by the use of cationic liposomes" *Cell Transplant.* 12:743-756 (2003). Garot et al., "Magnetic resonance imaging of targeted catheter-based implantation of myogenic precursor cells into infarcted left ventricular myocardium" *J Am Coll Cardiol.* 41:1841-1846 (2003); and Hinds et al., "Highly efficient endosomal labeling of progenitor and stem cells with large magnetic particles allows magnetic resonance imaging of single cells" *Blood* 102:867-872 (2003). Most superparamagnetic formulations appear to be biocompatible, safe, and nontoxic, and some already have been approved by the US Food and Drug Administration for non-stem cell applications. The problems with superparamagnetic particles include dilution of contrast with cell division; difficulty in quantification because of susceptibility artifact; and the potential transfer of contrast to nonstem cells, such as macrophages, after stem cell death.

A significant clinical problem common to all MRI methods is that certain implantable devices, such as pacemakers and defibrillators, are currently contraindications to scanning. Although a recent report suggests that patients with pacemakers can be scanned safely at 1.5 T,34 MRI's role in clinical stem cell trials remains unclear because patients with cardiac devices undoubtedly will be candidates for early stem cell clinical trials, and cardiac MRI is not readily available at all institutions.

C. Multimodality Contrast Agents

The integrated disadvantages of single contrast agent/detector pair prevent a generalized applicability to all biological cell clinical trials. As a result, dual- and multimodality contrast agents, which combine desired features of each technology, have been reported. For example, fluorophore-labeled MIONs permit injection of stem cells under optical image guidance and identification of single cells in pathological specimens ex vivo. Josephson et al., "Near-infrared fluorescent nanoparticles as combined MR/optical imaging probes" *Bioconjug Chem.* 13:554-560 (2002)' and Hill et al., Serial cardiac magnetic resonance imaging of injected mesenchymal stem cells" *Circulation* 108:1009-1014 (2003). Similar dual optical/MRI contrast has been described using visible-wavelength fluorophores and $Gd^{3+}$ chelators conjugated to high-molecular-weight scaffolds such as dextran. Modo et al., "Tracking transplanted stem cell migration using bifunctional, contrast agent-enhanced, magnetic resonance imaging" *Neuroimage* 17:803-811 (2002). Large nanoparticles generating simultaneous MRI, ultrasound, and fluorescence contrast have also been described. 37) and might prove useful for multimodality stem cell tracking. Wickline et al., "Nanotechnology for molecular imaging and targeted therapy" *Circulation* 107:1092-1095 (2003).

D. Biological Cell Tracking Techniques

Tracking the movement of different types of stem cells has been reported in a number of cellular cardiomyoplasty studies. See, Table 2.

MSCs have been performed in rodents and larger animals, and the fate and movements of the MSCs have been imaged with MRI, radioscintigraphy, and visible fluorescence. Hematopoietic cells and endothelial cells also have been targeted toward areas of infarcts within the heart and also have been visualized by various imaging modalities. With these cells, the therapeutic end point also includes neovascularization and angiogenesis, which often require other imaging modalities such as intravital microscopy and optical coherence tomography for assessment. Finally, embryonic stem cells are being tested in cardiac repair, and because their potential to differentiate and transmigrate is greater than that

TABLE 2

Conventional In Vivo Biological Cell Tracking Techniques

| Stem Cell Type/Host Species | Imaging Modality | Contrast Agent(s) | References |
|---|---|---|---|
| Mesenchymal stem/progenitor cell | | | |
| Mice | Whole-body visible fluorescence | Enhanced green fluorescent protein | Niyibizi et al., Mol Ther. 2004; 9: 955-963. |
| Rat | 3D confocal laser scanning microscopy | Calcein | Kihara et al., BBRC 2004; 316: 943-948. |
| Rat | Planar radioscintigraphy | $^{111}$In oxine | Gao et al., Cells Tissues Organs 2001 169: 12-20 |
| Rat | Planar radioscintigraphy/ex vivo visible fluorescence | $^{99m}$Tc-exametazime/PKH2 | Barbash et al., Circ, 2003; 108: 863-868. |
| Rat | MRI/ex vivo visible fluorescence microscopy | Iron oxide nanoparticles/enhanced GFP | Jendelova et al., J Neurosci Res. 2004 76: 232-243. |
| Rabbit | Radioscintigraphy | $^{125}$I- and $^{131}$I-transferrin (human) | Bai et al. Neuroreport 2004; 15: 1117-1120 |
| Pig | SPECT | $^{111}$In oxine | Chin et al., Nucl Med Commun. 2003 24: 1149-1154. |
| Pig | MRI/ex vivo visible fluorescence microscopy | Fluorescein-labeled iron nanoparticles | Hill et al., Circ, 2003 108: 1009-1014 |
| Hematopoietic/endothelial progenitor cell | | | |
| Mouse | Bioluminescence | Luciferase/luciferin | Wang et al., Blood 2003; 102: 3478-3482. |
| Mouse | Intravital visible fluorescence microscopy | PKH26 and PKH67 | Askenasy et al., Br J Haematol. 2003; 120: 505-515. |
| Rat | Planar radioscintigraphy/ex vivo visible fluorescence | $^{111}$In oxine/DiLDL | Aicher et al., Circ 2003; 107: 2134-2139. |
| Human | MRI | None | Britten et al. Circ 2003; 108: 2212-2218. |
| Endothelial cells | | | |
| Dog | Radioscintigraphy (ex vivo)/visible fluorescence microscopy | PKH26 and $^{125}$I-PKH95 | Ford et al., J Surg Res. 1996; 62: 23-28. |
| Embryonic stem cells | | | |
| Mouse | Whole-embryo visible fluorescence | DiI-conjugated acetylated LDL | Sugiyama et al., Blood 2003; 101: 4733-4738 |
| Rat | MRI/ex vivo visible fluorescence microscopy | Iron oxide nanoparticles/enhanced GFP | Jendelova et al., J Neurosci Res. 2004; 76: 232-243 |

The different types of cells in Table 2 have been reported to have specific characteristics in their mode of delivery and engraftment. For example, mesenchymal stem cells (MSCs), which can be isolated in adults and expanded in culture, have phenotypic characteristics of smooth muscle, skeletal myoblasts, and cardiac myocyte cells. A number of studies have shown that MSCs can reverse adverse remodeling when injected directly into the infarcted heart or after homing to the infarcted area when injected intravenously. Studies with of adult stem cells, multiple imaging modalities may be required to assess the overall distribution of these cells.

III. Limitations of Conventional In Vivo Biological Cell Imaging Systems

Strategic goals for imaging technology for tracking stem cells in clinical settings should be: i) the use of probes that are safe and non-toxic; ii) quantification of cell number; iii) single cell detecting sensitivity; iv) non-invasive; v) no biological cell genetic modification; vi) no radiation exposure;

vii) no significant transfer of the imaging probe to non-target cells upon target cell death; and a transmission of the probe upon cell division. Frangioni et al., "In vivo tracking of stem cells for clinical trials in cardiovascular disease" *Circulation* 110:3378-3384 (2004).

Clinical imaging modalities capable of tracking biological cells include, but are not limited to, i) magnetic resonance for example, as with MRI). Other limitations of methods not employing genetic modification of the cell include dilution of the signal with cell division, and extrusion of the probe upon cell death, resulting in signals that are not linked to cell viability. Many disadvantages are present in existing imaging strategies and are circumvented by the ultrasound imaging methods described herein. See, Table 3.

TABLE 3

Representative Current Cell Imaging Modalities.

| Imaging Modality | Probe | Disadvantages |
|---|---|---|
| Magnetic resonance - direct cell labeling | Superparamagnetic formulations - nanoparticles incorporated into stem cells | Probe dilution with cell division<br>Signal not linked to stem cell viability<br>Possible toxicity of probe<br>Cannot image patients with devices<br>Technically complex |
| Nuclear (SPECT, PET)- direct cell labeling | High energy photon emitters ($^{99m}$Tc, $^{111}$In, $^{18}$F, $^{124}$I) incorporated into stem cells | Low spatial resolution<br>Radiation to stem cells + patient<br>Signal not linked to stem cell viability<br>Decay of radioactivity limits serial imaging<br>Probe dilution with cell division<br>PET scanner - complex instrumentation |
| Nuclear (SPECT, PET) - transgenic approaches (cells modified to express reporter genes) | Reporter genes/probes - stem cell transgene encodes for enzyme, systemic injection of radioactive substrate for enzyme | Requires genetic modification of stem cell<br>Radiation to stem cells + patient<br>PET scanner - complex instrumentation |
| Optical (bioluminescence) | Luciferase/luciferin- stem cell modified to express luciferase; luciferin injected prior to imaging | Requires genetic modification of stem cell<br>Can only be performed in small animals due to high tissue attenuation of photons<br>Repetitive luciferin injection for serial imaging may be immunogenic |
| Optical (fluorescence) | Fluorescent probes (near infrared) incorporated into stem cells (e.g. GFP, quantum dots) | Limited to near-field imaging<br>Probe dilution with cell division<br>Signal not linked to viability |

Underlined disadvantages are improved or resolved using the microbubble ultrasound technology described herein.

imaging (MRI), and ii) nuclear imaging including, but not limited to, positron emission tomography (PET) and single photon emission computed tomography (SPECT). Both MRI and nuclear imaging approaches employ direct ex vivo labeling of cells with the imaging probe prior to cell delivery. Other radiation approaches employ genetic modification of the cells to stably express a reporter gene that encodes enzymatic conversion of a PET or SPECT substrate. Optical methods such as bioluminescence and fluorescence are limited to use in small animals or for superficial imaging. Beeres et al., "Role of imaging in cardiac stem cell therapy" *J Am Coll Cardiol* 49:1137-48 (2007); and Hoshino et al., "In vivo tracking in cardiac stem cell-based therapy" *Prog Cardiovasc Dis* 49:414-420 (2007).

Safety issues that potentially limit these technologies include, but are not limited to, the requirement for radiolabeling or genetically modifying the stem cells, radiation exposure to the patient, and/or toxicity of iron particles (i.e., In conclusion, x-ray techniques do not provide adequate contrast sensitivity for cardiovascular stem cell tracking in the clinical setting. Bioluminescence is limited to small animal studies and NIR fluorescence to near-surface and histological applications. Ultrasound/echocardiography has the potential for single-cell detection but has limited anatomic accessibility, resolution, and quantification. High-energy photon imaging (SPECT or PET) has high sensitivity, but for long-term tracking it requires genetic manipulation of the stem cell, stable expression of a transgene, and multiple exposures to ionizing radiation. MRI provides excellent 3-dimensional anatomy but is contraindicated for many patients and has limited availability at many institutions, and some contrast techniques have low sensitivity. Although multimodality contrast agents might improve the prospects for stem cell tracking both in vivo and ex vivo, no currently available imaging technology is ideal. Impending clinical trials utilizing stem cells must define, carefully, the limits of the imaging technology chosen.

IV. Advantages of In Vivo Contrast-Enhanced Ultrasound Imaging

Given the inherent limitations of currently available imaging technology, some embodiments of the present invention improve imaging sensitivity while minimizing patient exclusion, study cost, and study complexity. For example, paramagnetic chemical exchange saturation transfer (PARACEST) agents for MRI have the potential to improve MRI sensitivity by up to 2 orders of magnitude. Zhang et al., "PARACEST agents: modulating MRI contrast via water proton exchange" *Acc Chem. Res.* 36:783-790 (2003). While other electromagnetic frequencies offer certain advantages, compatible exogenous contrast agents do not yet exist. Ferguson et al., "Towards functional 3D T-ray imaging" *Phys Med Biol.* 47:3735-3742 (2002). Solid-state nanotechnology solutions, however remote at present, are particularly attractive because they could potentially provide noninvasive, real-time monitoring of intracellular pH, calcium, etc, as well as anatomic location, of single stem cells.

In one embodiment, the present invention contemplates a method for biological cell imaging comprising internalizing therapeutic MSCs with at least one ultrasound contrast agent thereby rendering the MSCs visible during diagnostic medical ultrasound imaging. For example, ultrasound contrast agents may comprise gas-filled microbubbles, wherein the microbubble has a biocompatible shell. Typically, these microbubbles are synthesized with precision to a specific size (i.e., for example, between approximately 100 nanometer to 10 microns, but typically between approximately 2-3 μm in diameter. Ultrasound contrast agents have been reported to opacify the blood pool during echocardiographic imaging, where the contrast agents are used as red cell tracers. Two ultrasound contrast agents are FDA approved and are comprised of a lipid shell or albumin shell encapsulating a perfluorocarbon gas as an acoustically active gas. Kaul S., "Myocardial contrast echocardiography: A 25-year retrospective" *Circulation* 118:291-308 (2008); and Becher et al., "Handbook of contrast echocardiography" 2000 New York Springer-Verlag.

When ultrasound is delivered at the natural resonance frequency of a particular polymer contrast microbubble population, the microbubbles expand and contract (e.g., oscillate) symmetrically. However, at higher acoustic powers, these oscillations become asymmetric and non-linear behavior is observed. de Jong N., "Basis acoustic properties of microbubbles" *Echocardiography* 19:229-240 (2002).

Under conditions where these ultrasound-induced polymer contrast microbubble oscillations are occurring at twice or three times the delivered ultrasound frequency (i.e., for example, the second and third harmonic frequencies, respectively), the microbubbles generate ultrasound emissions themselves, which can be detected by ultrasound scanners designed to detect harmonic frequencies or non-linear microbubble behavior. Becher et al., Handbook of contrast echocardiography. 2000. New York Springer-Verlag. Because biological tissue and/or biological cells do not oscillate in response to medical ultrasound frequencies, tissues and/or cells do not generate a harmonic signal. Consequently, when observing a 2D ultrasound image a selective detection of the microbubble signal appearing as contrast enhancement (i.e., for example, brightness) may be observed as distinct from the black appearance of the surrounding tissue.

In one embodiment, the present invention contemplates a method detecting an ultrasound contrast agent that has been internalized into biological cells. Although it is not necessary to understand the mechanism of an invention, it is believed that the internalization of polymer contrast microbubbles within biological cells will convert an otherwise ultrasonically 'invisible' biological cell to an ultrasonically 'visible' biological cell. In one embodiment, the microbubble resides within the intracellular space of the biological cell in sufficient number to generate detectable signals. In one embodiment, at least a portion of the microbubbles are passed on to daughter cells upon cell division.

Most conventional FDA-approved microbubbles comprise an albumin or lipid shell and are unlikely to withstand the endocytotic process of a viable biological cell. Consequently, it is to be expected that conventional commercially available FDA-approved microbubbles would have a short survival time within a biologically active cell, thereby being inappropriate, and unsuccessful, for use in the presently contemplated methods. Clearly, the art requires a more robust shell design. Further, this improved microbubble must also "die" if/when the cell dies, so that unlike other imaging technologies using labeling probes, the image signal does not persist beyond the lifetime of the stem cell.

In one embodiment, the present invention contemplates an improved polymer contrast microbubble comprising a biodegradable polymer shell. In one embodiment, the polymer shell comprises a tunable double shell microbubble (i.e., for example, a bi-layer microbubble). In one embodiment, the inner shell comprises a biodegradable polymer. In one embodiment, the outer shell comprises human albumin. Although it is not necessary to understand the mechanism of an invention, it is believed that the outer surface enhances biocompatibility.

In one embodiment, the methods of the present invention comprise 2D ultrasound imaging. Although it is not necessary to understand the mechanism of an invention, it is believed that 2D ultrasound imaging overcomes most of the disadvantages of existing imaging technologies as outlined above. For example, the spatial resolution of ultrasound is believed to exceed that of nuclear imaging and optical methods. Furthermore, it is a tomographic imaging method that allows three dimensional interrogation of target tissue, not possible using optical methods which summate signals emanating along a z axis (depth of tissue) into a 2D plane. The disclosed embodiments herein do not involve radiation exposure to the patient or biological cell, and do not require genetic modification of a biological cell to enable detection. In some embodiments, serial (i.e., repetitive) imaging is safe because ultrasound technology does not involve ionizing radiation. This advantage allows serial imaging of biological cell trafficking over prolonged periods of time. Furthermore, the instrumentation involved is simple (as compared to MRI or PET), and its portability confers the potential for widespread use in diverse clinical settings.

V. Development of Polymer Contrast Microbubble Enhanced Ultrasound Imaging

Development of polymer contrast microbubble-enhanced ultrasound technology for tracking biological cells is illustrated herein using culture-expanded bone marrow-derived mesenchymal stem cells (MSCs). Data presented herein demonstrate in vitro studies designed to optimize microbubble chemistry, achieve comprehensive acoustic characterization of microbubble-MSC conjugates, and identify any MSC cytotoxicity. These studies are performed with acoustic testing and cytotoxicity data that improve microbubble design on an empirical and iterative basis. The optimized microbubble design is then used for in vivo animal testing.

A. Methods for Making Biological Cells with Internalized Microbubbles

In one embodiment, the present invention contemplates a method for making a composition comprising a biological cell, wherein the biological cell comprises a plurality of ultrasound contrast agent microbubbles. In one embodiment, the biological cell comprises a stem cell. In one embodiment, the stem cell comprises a human MSCs (hMSCs). In one embodiment, the present invention contemplates a method comprising making polymer contrast microbubbles in a high efficiency, precise, and quantitative manner.

In one embodiment, the present invention contemplates a method for detecting polymer contrast microbubbles comprising an acoustically active gas during ultrasound imaging. Although it is not necessary to understand the mechanism of an invention, it is believed that the present detection method is based on the phenomenon of microbubble resonance (i.e., for example, oscillation) in an ultrasound field. For example, when microbubbles are insonified at their natural resonance frequency and sufficient acoustic power, the microbubbles oscillate, resulting in ultrasound emissions at harmonic frequencies. Ultrasound imaging systems configured to receive the harmonic ultrasound frequencies arising from the oscillating microbubbles display the signals as an increase in video intensity (i.e., for example, brightness) in comparison to tissue, which appears unenhanced (i.e., for example, darkness).

The data presented herein demonstrates that when polymer contrast microbubbles are systemically delivered, or internalized into biological cells, the microbubbles are acoustically distinct from surrounding tissue. Methods have been reported that facilitate the construction of a microbubble comprising a double layer nitrogen-filled microbubble comprised of an inner shell made of a biodegradable polymer and an outer shell made of albumin. Short R. E., "Method for preparing gas-filled polymer matrix microparticles useful for echocardiographic imaging" U.S. Pat. No. 6,919,068 (herein incorporated by reference; currently owned by the University of Pittsburgh); Villanueva et al., "Detection of coronary artery stenosis using power Doppler imaging" *Circulation* 103: 2624-2630 (2001); Raisinghani et al., "Myocardial contrast echocardiography (MCE) with triggered ultrasound does not cause premature ventricular complexes: Evidence from PB127 MCE studies" *J Am Soc Echo* 16:1037-1042 (2003); and Main et al., "Pulmonary homodynamic effects of dipyridamole infusion in patients with normal and elevated pulmonary artery systolic pressure receiving PB127" *J Am Soc Echocardiogr* 19:1038-1044 (2006). By modulating microbubble properties including, but not limited to, shell thickness, polymer composition, gas content, and size, microbubbles can be prospectively "tuned" to an appropriate resonance frequency thereby controlling microbubble survival times and/or biodegradation rates. Such control over microbubble composition maximizes internalization efficiency and permits controllable 'dosing' of microbubble content per cell. In one embodiment, the present invention contemplates a composition comprising a double shell polymer contrast microbubble measuring between approximately 100 nanometer to 10 microns, but more preferably between 2-3 μm in diameter and encapsulating a nitrogen acoustically active gas. In one embodiment, the microbubbles comprise a fluorescent label. In one embodiment, the label comprises BODIPY.

Figure 24:
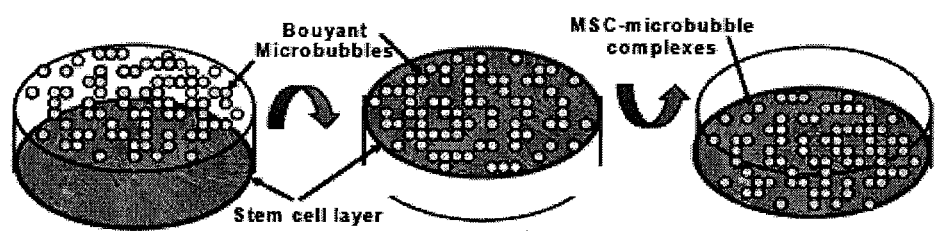
FIG. 24 presents an illustration of one embodiment for a method to make cultured biological cells (i.e., for example, hMSCs) with internalized polymer contrast microbubbles that may, or may not, be fluorescently labeled. For example, a method comprises a cell/microbubble feed ratio of 1/1000. (i.e., for example, the microbubbles may comprise).

In one embodiment, the present invention contemplates a method comprising contacting culture-expanded hMSCs with polymer contrast microbubbles under conditions such that the microbubble becomes internalized within the hMSC, thereby creating an internalized hMSC. See, FIG. 24. Such a method uses microbubble buoyancy to 'force' encounters between microbubbles and cultured hMSCs in an plastic culture dish, where the hMSCs form the roof of the dish. Subsequently, the cells are incubated after the exposure procedure and then trypsinized and washed. The percentage of labeled hMSCs (labeling efficiency) and average number of microbubbles/cell can be quantified in multiple fields using fluorescent microscopy and flow cytometry. Under conditions of low labeling efficiency a FACs cell sorting technique can be used to enrich the population by preferentially selecting out labeled hMSCs. This method is an empirical and interactive process guided by the several target outcomes. See, Table 4.

TABLE 4

Empirical Guidelines For Microbubble Composition Optimization

| Target Outcome | Justification | Experimental Manipulations | Evaluation Methods |
| --- | --- | --- | --- |
| High labeling efficiency (>90%) | To maximize image signal from a given injection of hMSCs | Vary microbubble formulation, size, charge, "feed ratio," MSC exposure conditions | Fluorescence microscopy; flow cytometry |
| Precisely titrate number of microbubbles per hMSC | To control image signal intensity; ensure adequate number of microbubbles to pass to next generation of hMSC; control of any dose-dependent cytotoxicity | Vary "feed ratio," MSC exposure conditions . . . 2.3 . . . 0202230. | Fluorescence microscopy; flow cytometry |
| Retention of microbubble acoustic activity after hMSC internalization | To allow hMSC visualization with ultrasound imaging | Vary polymer in microbubble shell, shell thickness, and type of gas in microbubble | Acoustic (spectral) and ultrasound imaging analysis |
| Persistence of microbubbles after hMSC division | To allow ultrasound visualization of daughter cells | Vary microbubble polymer to favor intracellular persistence; manipulations that enable control over number of internalized hMSCs | Serial fluorescence microscopy; acoustic (spectral) and ultrasound imaging analysis of dividing hMSCs over 1 week |

TABLE 4-continued

Empirical Guidelines For Microbubble Composition Optimization

| Target Outcome | Justification | Experimental Manipulations | Evaluation Methods |
|---|---|---|---|
| Biodegradation of microbubbles upon cell death | To link image signal to hMSC viability (avoid "false positive" signal from non-hMSC uptake of microbubbles released by dying MSCs) | Vary polymer composition of shell to respond to death signals (e.g. pH-sensitive shell degradation); modulate microbubble fragility (shell thickness, gas) | Induce necrosis or apoptosis of MSCs after microbubble internalization, perform acoustic testing and ultrasound imaging |
| Absence of cytotoxicity from microbubbles | To preserve hMSC biological function and therapeutic effects | Vary microbubble composition, size, exposure conditions, number of microbubbles/hMSC | Viability, proliferation, migration, and differentiation assays |

Optimization of microbubble formulations and labeling protocol resulting in hMSC internalization comprise methods using an empirical and iterative approach based upon microbubble responses to the acoustic and cytotoxicity target outcomes.

In one embodiment, the present invention contemplates a method for labeling hMSCs with internalized fluorescently labeled polymer contrast microbubbles. For example, hMSCs with internalized contrast microbubbles have been observed under brightfield and fluorescence microscopy. See, FIG. 25 and FIG. 26, respectively. Colocalization of fluorescent microbubbles and hMSCs and the fusion images suggest a high labeling efficiency. See, FIG. 27. The confocal microscopy image also shows that the microbubbles are located both on the surface and within the cytoplasm of the hMSCs.

B. Methods for Ultrasound Imaging with Internalized Microbubbles

Successful methods for ultrasonic cell imaging and cell tracking should have contrast agents that retain acoustic activity (i.e., for example, an ability to cause contrast enhancement) after internalization into a biological cell. For example, the gas content of the microbubble should be retained. Preservation of microbubble shell structural integrity after internalization is not the only factor regarding acoustically active gas retention. For example, internalized gas could be replaced with water through mass transfer across the shell, rendering the bubble acoustically inert. Alternatively, the shell could be hydrolyzed thereby resulting in release of the gas particularly if microbubble cell uptake is mediated by endocytosis.

Successful methods for ultrasonic cell imaging and cell tracking should also link the ultrasound signal to hMSC viability. For example, acoustic activity of the microbubble should be retained for the lifetime of the hMSC and daughter cells, but the microbubbles must "die" if/when the hMSC dies. Thus, internalized microbubble formulations should be able to generate harmonic signals over a biological cell's life cycle. The methods herein were created using an empirical and iterative use of derived data to redesign new bubbles thereby meeting established outcome criteria. See, Table 4. For example, these empirical procedures developed new driving ultrasound pulse sequences to stimulate the microbubbles, optimized detection (e.g., imaging) strategies by analyzing microbubble-hMSC acoustic "signatures," or to justify moving to in vivo testing (i.e., for example, clinical trials).

The optimized polymer microbubble internalized into bone marrow-derived cultured-expanded hMSCs described above was used to optimize the imaging conditions presented herein. Nonetheless, it should be realized that any biological cell capable of internalizing a polymer microbubble may also be used. All microbubble-hMSC experimental groups were compared to control groups with the same hMSC density but without exposure to microbubbles. All control groups were subjected to the same testing as the microbubble-hMSCs groups and analyzed in the same fashion. Tests are performed immediately after microbubble internalization and at 4, 24, 48, 72 hours and 7 days thereafter. Adjustments can be made in cell seeding concentrations to allow for proliferation and study up to 1 week after internalization. Two representative strategies can be used to acoustically test microbubble hMSC complexes in vitro: i) spectral analysis can evaluate for harmonic responses of the labeled hMSCs to ultrasound; and ii) 2D ultrasound imaging can measure the echogenicity of the internalized hMSC complexes.

Figure 28:
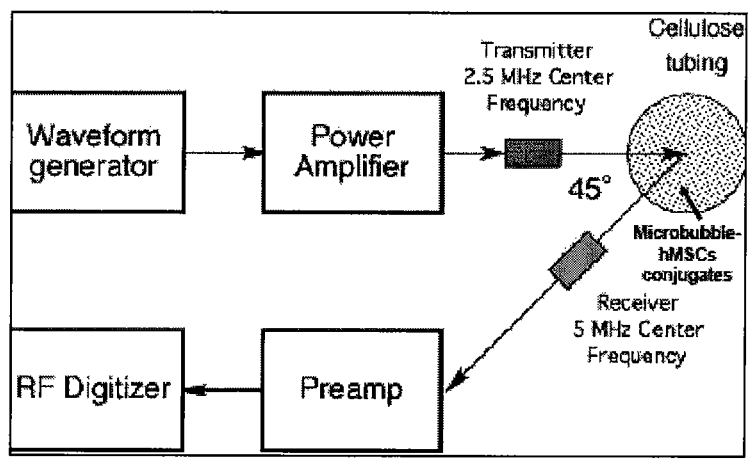
FIG. 28 presents one embodiment of a spectral analysis testbed capable of in vitro acoustic characterization of microbubble-hMSC conjugates.
Figure 29:
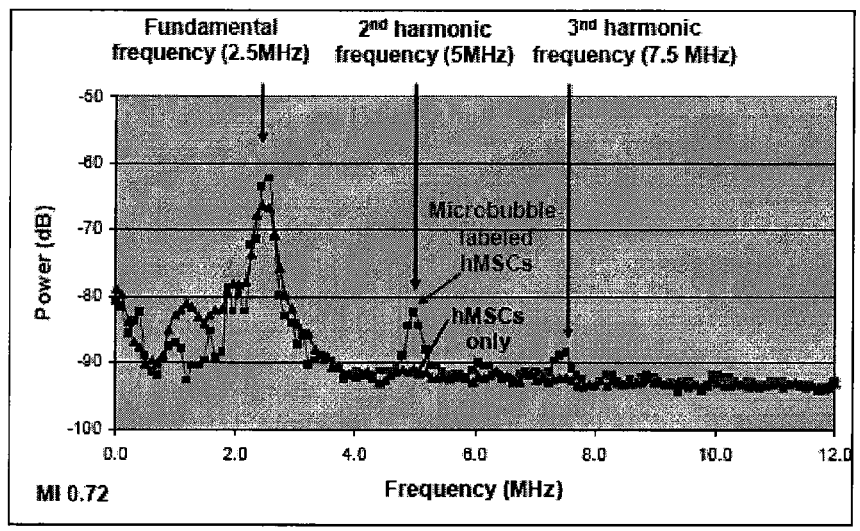
FIG. 29 presents exemplary data of a spectral analysis of hMSCs comprising internalized polymer contrast microbubbles vs hMSC alone using the setup in FIG. 28.
Figure 29:
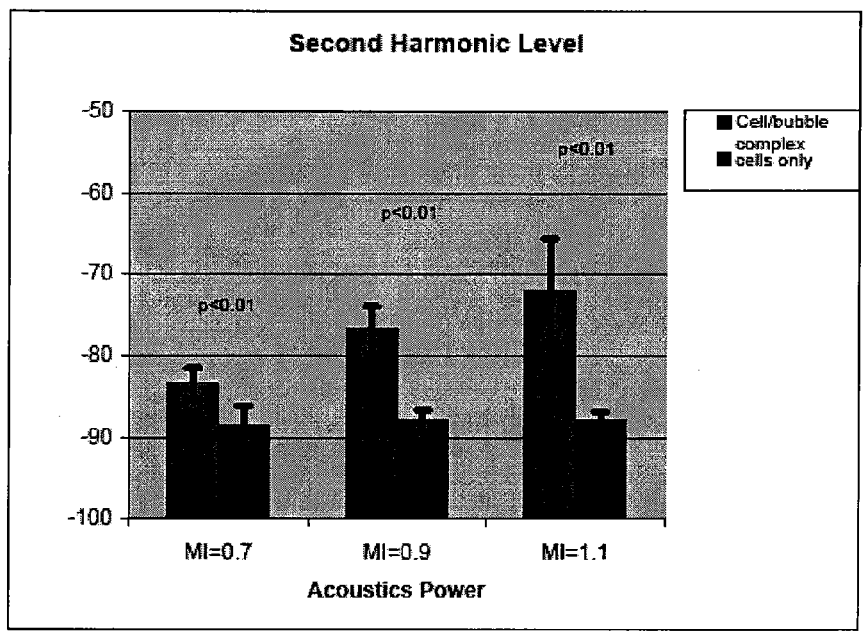
Figure 30:
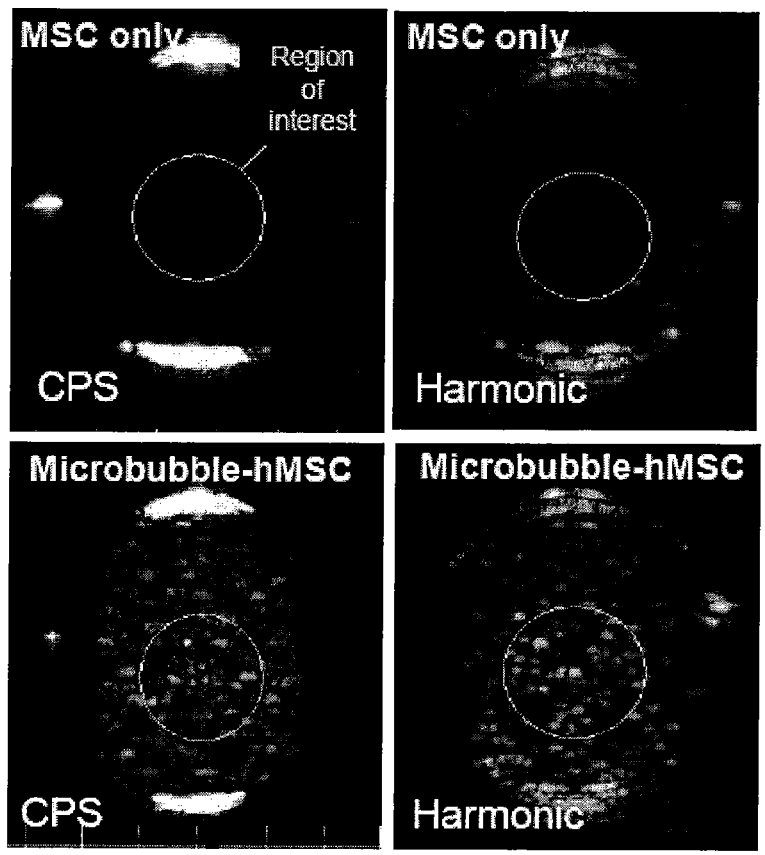
FIG. 30 presents exemplary data of 2D imaging of the same samples used in FIG. 29.
Figure 30:
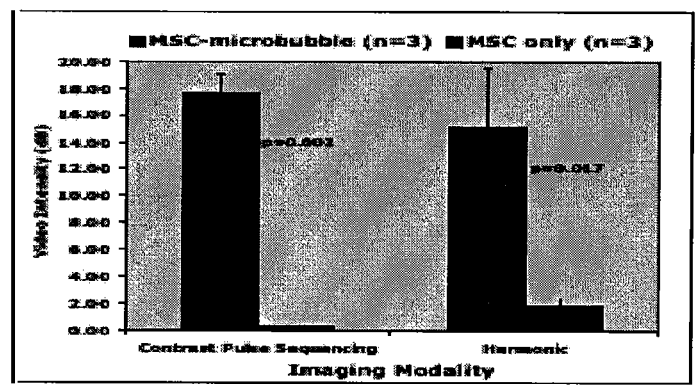
Figure 31:
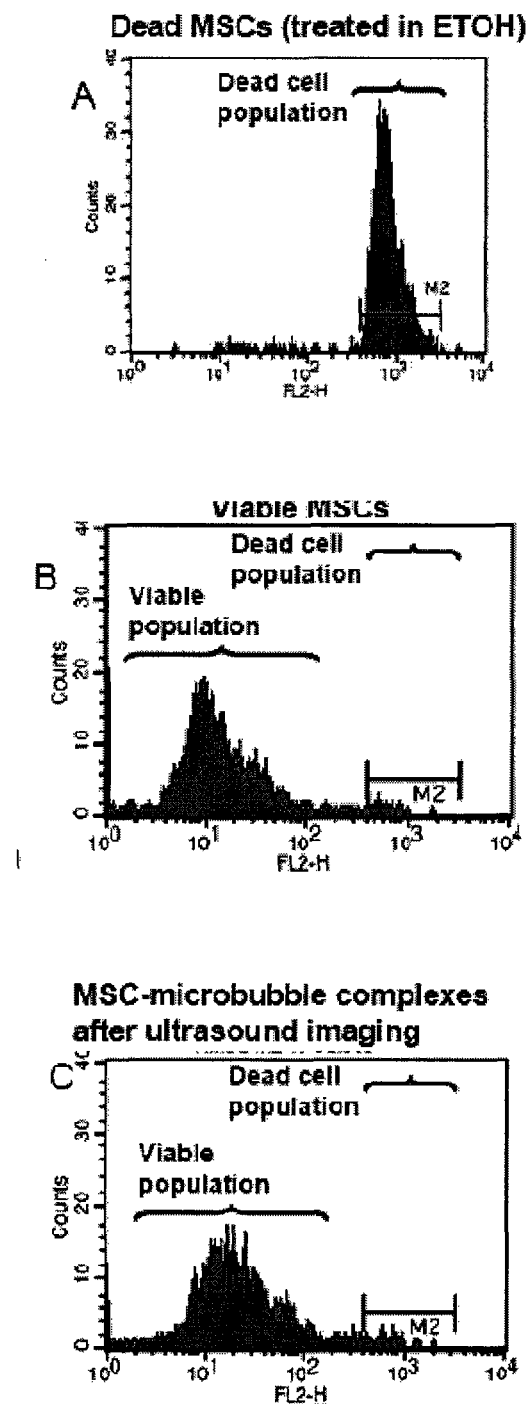
FIG. 31 presents exemplary data showing live/dead stain flow cytometry data for, control ethanol-killed hMSCs (Panel A), control viable hMSCs (Panel B), and microbubble labeled hMSCs exposed to ultrasound 24 hours after labeling (Panel C).
Figure 32:
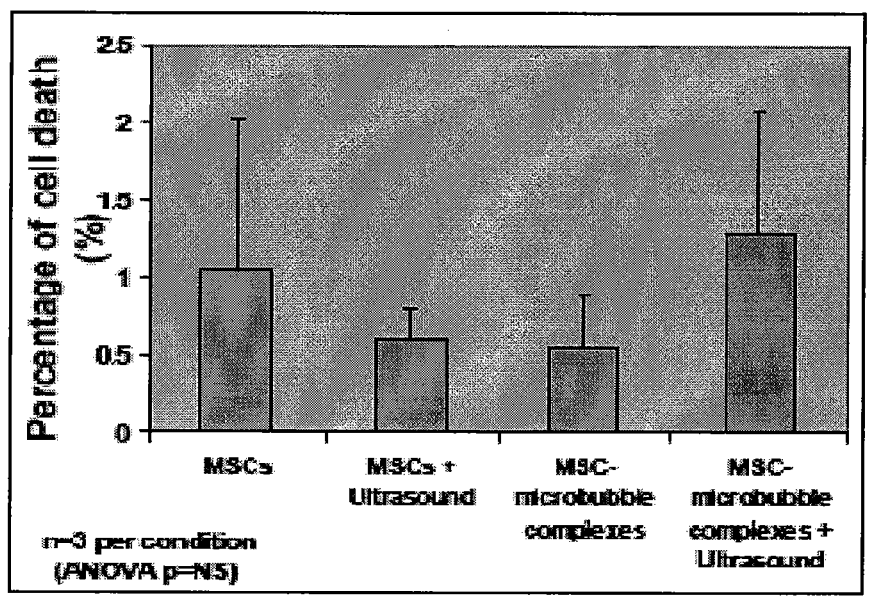
FIG. 32 presents exemplary summary data shown in FIG. 31 as a bar graph of the % dead cells for varying experimental conditions, indicating no change in viability during these studies performed at 24 hours after the initial hMSC labeling.
Figure 33:
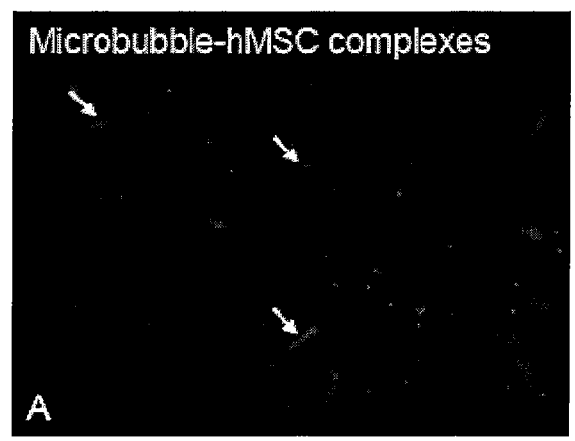
FIG. 33 presents exemplary data of the effect of fluorescently labeled (BODIPY) internalized contrast microbubbles on cell migration activity. Fluorescently labeled hMSCs (arrows) migrate through 8 μm pores (arrowheads) from a serum-free to a serum media environment.
Figure 33:
Figure 34:
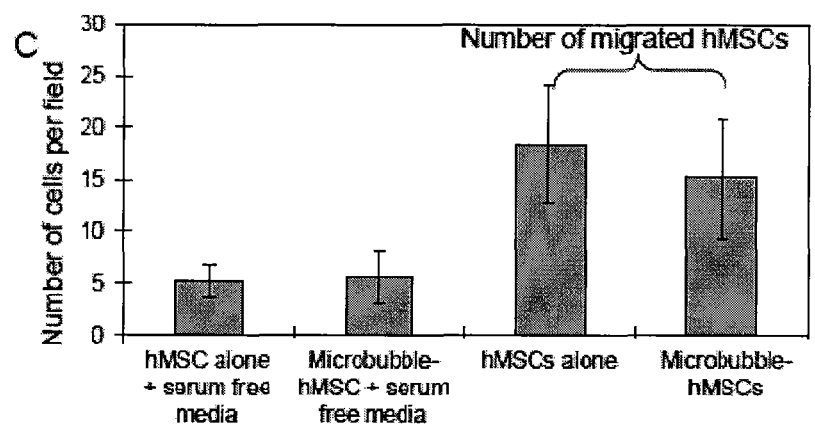
FIG. 34 presents exemplary summary data of FIG. 33 demonstrating that hMSCs comprising internalized fluorescently labeled contrast microbubbles do not appear to change cell migration 24 hours after labeling.

Spectral analysis evaluates the frequency components of the ultrasound signal returning from an object placed in an ultrasound field. This analysis facilitates the creation of a microbubble-hMSC complex that, in the presence of ultrasound, generates a video intensity signal distinct from surrounding tissue. For example, one approach is to insonify microbubble-hMSC complexes and to look for harmonic components in the returning signal, because resonating bubbles generate harmonics whereas tissue does not. A representative testbed suitable for this analysis includes a dual transducer in which microbubble-hMSC complexes are insonified with a 2.5 MHz transducer, and a 5 MHz receive transducer is confocally positioned 45° to the transmit transducer. See, FIG. 28. Fourier transformation may then be performed on the received radio frequency signal.

2D ultrasound imaging is capable of confirming if the microbubble-hMSC formulations demonstrating the strongest harmonic activity upon spectral analysis can be imaged with a clinical ultrasound scanner. Such data is also useful for optimizing ultrasound machine settings which generate the highest signal/noise ratio. In one testbed set-up an ultrasound imaging transducer is submerged in an acoustically insulated tank and affixed to a device that permits precise vertical scanning of the cells using non-linear imaging at frequencies up to 14 MHz. Image analysis is performed by measuring video intensity (dB) in regions of interest drawn around the sample holder. See, FIG. 10.

Optimization of microbubble imaging methods may be accomplished through empirical and iterative data collections evaluating the responses of microbubble-hMSC constructs to ultrasound. Several acoustic parameters are identified that are believed to achieve specific imaging outcome criteria that result in optimized imaging. Table 5.

TABLE 5

Empirical Guidelines For Microbubble Imaging Optimization

| Target Outcome | Justification | Experimental Manipulations | Evaluation Methods |
| --- | --- | --- | --- |
| High signal to noise ratio | To maximize sensitivity for detecting hMSCs in vivo | Change driving frequency, acoustic pressure, and/or tone bursts, dynamic range to identify strongest non-linear response; image processing algorithms (e.g. digital subtraction) | Comparison of background vs. microbubble-hMSC spectra; video intensity on ultrasound images |
| Minimize ultrasound-induced microbubble destruction | To maximize signal per hMSC; prolong duration of 'useful' imaging;" reduce potential cytotoxicity from cavitation | Modulate acoustic power to achieve maximum signal without microbubble destruction | Measure video intensity degradation at higher acoustic powers |
| Quantification of signal (dose response effect) | To establish relationship between signal strength and the number of hMSCs; to achieve single cell sensitivity | Vary concentration of microbubble-hMSC complexes or microbubbles per MSC in test sample; vary imaging parameters (frequency, power, dynamic range, gain) | Measure video intensity in relation to known number of microbubble-hMSC complexes or microbubbles/hMSC |

Data presented herein demonstrate that polymer contrast microbubbles retain acoustic activity after internalization by hMSCs and that hMSCs become ultrasonically visible in vitro upon internalization of microbubbles. For example, spectral analysis and imaging of the microbubble-hMSC complexes are discussed above. See, FIGS. 25-27. Further data is presented measuring the received frequency spectrum of microbubble-hMSCs vs hMSCs alone at a transmit frequency of 2.5 MHz. There is a fundamental frequency component at 2.5 MHz for hMSCs alone and microbubble-hMSCs, indicating that fundamental imaging at 2.5 MHz would not be able to distinguish hMSCs from surrounding tissue. See, FIG. 29. Discrete peaks are observed at 5 and 7.5 MHz for the microbubble-hMSCs that are not present for the hMSCs alone, indicating a unique 2nd and 3rd harmonic response from the labeled hMSCs. At higher acoustic power, the harmonic response appears to further increase (data not shown). These data suggest that a harmonic-based detection strategy should be able to distinguish the hMSCs from surrounding tissue, which does not have a strong harmonic.

2D ultrasound imaging confirmed that the harmonic signals identified during spectral analysis can be detected using a clinical scanning system. Images of samples from the above spectral analysis were subjected to two non-linear imaging modalities, harmonic and contrast pulse sequence (CPS). See, FIG. 30. There was no signal (black images) from the hMSCs-only sample, whereas there was strong video intensity signal from the microbubble-labeled hMSCs sample, thereby confirming that hHMCs become ultrasonically visible immediately upon internalization of microbubbles. With both harmonic and CPS imaging, there is a stronger signal from the microbubble-hMSCs sample.

It is expected that the present optimization methods can derive different polymer formulations that have high internalization efficiency, controllable dosing (i.e., for example, the number of internalized bubbles per cell) and a stable microbubble lifetime. For each formulation a specific set of acoustic properties are known, thereby forming a rational basis for in vivo testing. The duration of "useful imaging" (acoustic activity) can also be controlled when using biological cells with internalized microbubbles.

C. Internalized Microbubbles are Biocompatible

As with all in vivo cell tracking techniques, any effects of the tracking probe itself on the normal activities of the cell can affect the results. While preliminary data suggest that internalized hMSCs are not cytotoxic (see below), tests to determine with the internalization methods and/or the presence of intracellular microbubbles affect cellular activities. Consequently, the data presented herein also describes a systematic evaluation of the effect of microbubble internalization on hMSC viability and other stereotypical functions of hMSCs. These functions are evaluated up to 7 days after internalization.

Figure 25:
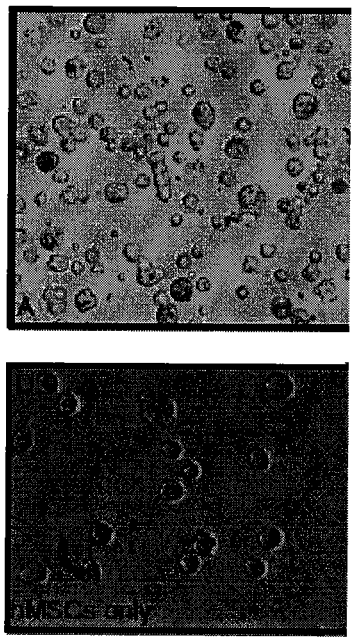
FIG. 25 presents exemplary data comparing hMSCs comprising fluorescently labeled polymer contrast microbubbles (Panel A) or alone (Panel D) under brightfield microscopy.
Figure 26:
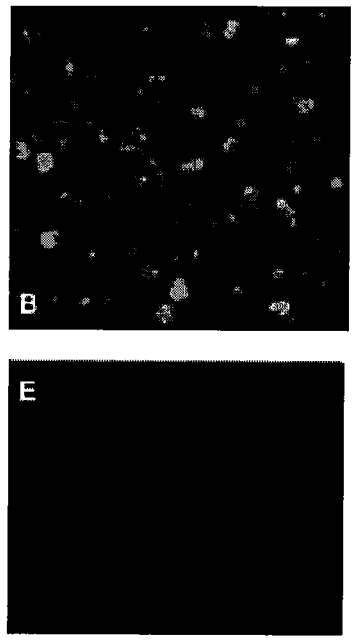
FIG. 26 presents exemplary data comparing hMSCs comprising fluorescently labeled polymer contrast microbubbles (Panel B) or alone (Panel E) under fluorescence microscopy.
Figure 27:
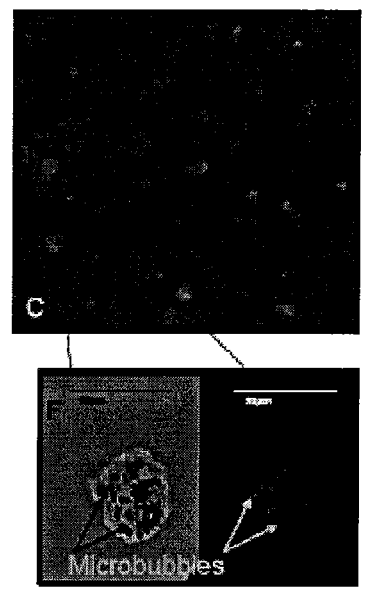
FIG. 27 presents exemplary data showing a fusion of FIG. 25 Panel A and FIG. 26 Panel B (Panel C).
Figure 27:
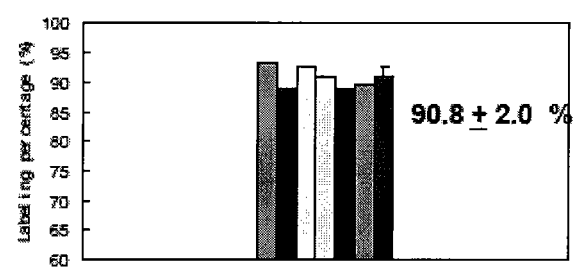

In one embodiment, the polymer microbubbles disclosed herein comprise improved biocompatibility than currently available microbubble compositions, thereby providing a safer and more clinically acceptable method of administration. For example, In one embodiment, the presently disclosed microbubbles are made of biodegradable polymers covered with albumin that minimizes toxicity. Clinical studies have reported that this polymer agent as a red cell tracer in humans. Raisinghani et al., "Myocardial contrast echocardiography (MCE) with triggered ultrasound does not cause premature ventricular complexes: Evidence from PB127 MCE studies" *J Am Soc Echo* 16:1037-1042 (2003); and Main et al., "Pulmonary homodynamic effects of dipyridamole infusion in patients with normal and elevated pulmonary artery systolic pressure receiving PB127" *J Am Soc Echocardiogr* 19:1038-1044 (2006). Additionally, the data disclosed herein suggest that, at least up to 48 hours after labeling, the microbubbles do not affect cell viability or migration. FIGS. 31-34. Further, these studies are performed with hMSCs that have an optimized number of intracellular microbubbles. FIGS. 25-27. One source of toxicity might be might be related to microbubble cavitation (bursting) in the cell during ultrasound imaging. In some embodiments described herein in vitro studies may be performed to understand mechanisms of toxicity. For example, such in vitro studies can be designed such that the acoustic powers are adjusted accordingly to avoid microbubble destruction.

One experimental design determines whether polymer microbubble internalization by hMSCs results in cytotoxicity at up to 1 week after internalization. The data was systematically performed on microbubble-hMSC constructs emerging from optimized microbubble imaging methods and compositions (supra), and is also used to modify microbubble formulations and acoustic settings. See, Table 4. Each microbubble-hMSC construct tested was compared to a corresponding control group of identical hMSC density without microbubble labeling and/or non-viable MSCs. Starting with low cell densities assays were performed before, immediately after, and 6, 24, 48, 72 hours and 7 days after microbubble internalization. See, Table 6.

TABLE 6

Methods for evaluating possible toxicity of microbubble: hMSC complexes with or without ultrasound.

| Cell Activity | Evaluation Method | Outcome Measurement |
|---|---|---|
| Proliferation | BrdU incorporation assay | Rate of DNA synthesis |
| Viability | Live/dead stain (eithidium homodimer-1) | % of dead cells by flow cytometry |
| Apoptosis | TUNEL stain | % of apoptotic cells by microscopy |
| Migration | Migration assay - CMFDA-labeled cells migrating through membrane with 8 μm pores in the presence of a serum gradient | Number of cells attached to membrane on other side of pores on fluorescence microscopy |
| Differentiation | Adipogenic and osteogenic differentiation assays | Microscopy: Adipocyte staining (Oil Red-O); ostegenic detection using tetracycline labeling and staining |

The data presented herein demonstrates viability and migration of microbubble-MSC complexes up to 48 hours after internalization. For illustrative purposes, the microbubble-hMSC construct imaged in FIG. 27 were assessed for viability and migration. The data show no difference in the small percentage of dead cells between the microbubble-hMSC and hMSC-only conditions. See, FIG. 31, Panel C and Panel B, respectively. The % dead cells remains similar for varying experimental conditions, indicating no change in viability during these studies performed at 24 hours after the initial hMSC internalization. See, FIG. 32. Similar data was observed at 48 hours (data not shown). Subsequently, migration studies were performed 24 hours after microbubble labeling of fluorescently labeled hMSCs. See, FIG. 33. hMSCs (green cells, arrows) were observed to have migrated through 8 μm pores (green dots, arrowheads) in response to a serum gradient in the culture medium. Similar numbers of microbubble-labeled hMSC complexes and non-labeled hMSCs have migrated through 8 μm pores. See, FIG. 33, Panel A and Panel B, respectively. The comparative data is summarized demonstrating the microbubble labeling of hMSCs does not appear to change cell migration 24 hours after labeling. See, FIG. 34.

Figure 39:
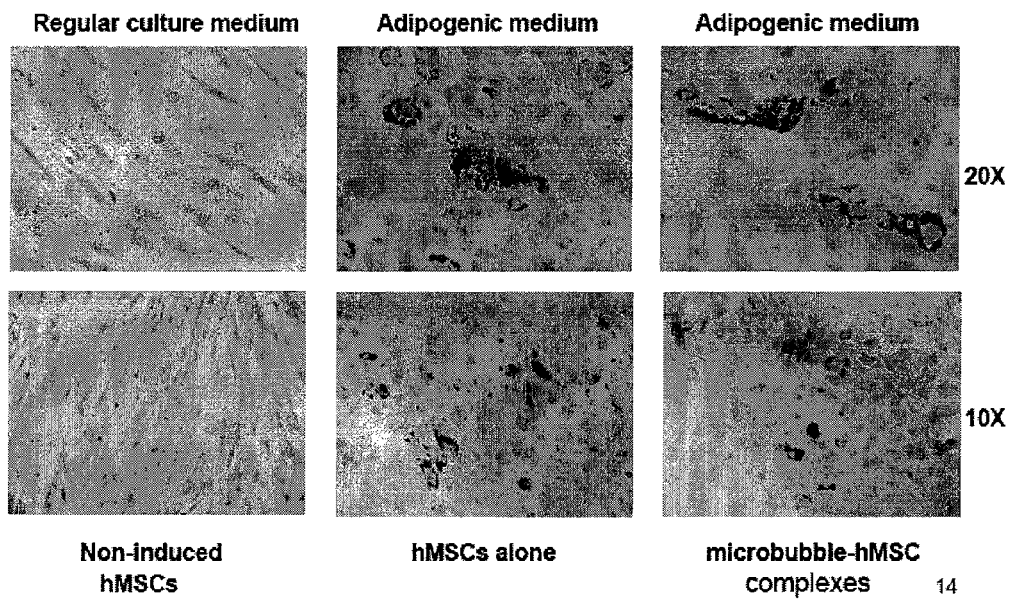
FIG. 39 presents exemplary photomicrographs comparing the effects of hMSCs and hMSC-microbubble complexes on the ability of adipocytes to differentiate. Staining: Oil Red O.
Figure 40:
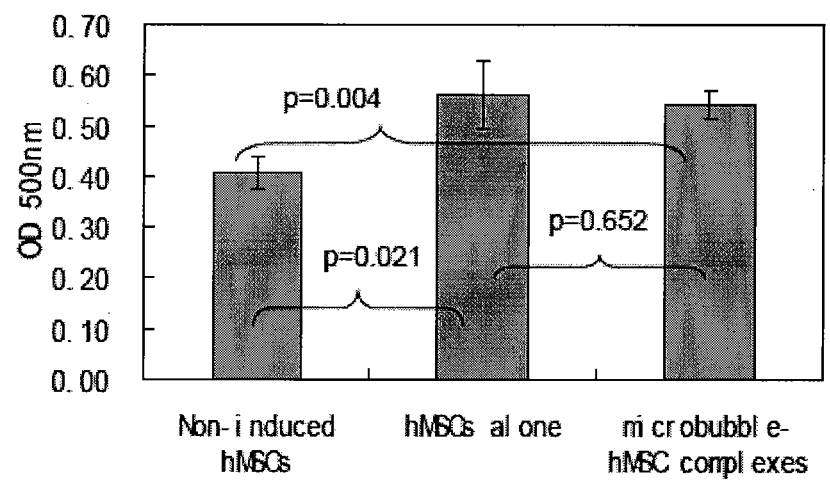
FIG. 40 presents exemplary quantitative data of the photomicrographs in FIG. 39 demonstrating that hMSC-microbubble complexes had no effect on the ability to induce adipocyte differentiation as compared to hMSCs alone.
Figure 41:
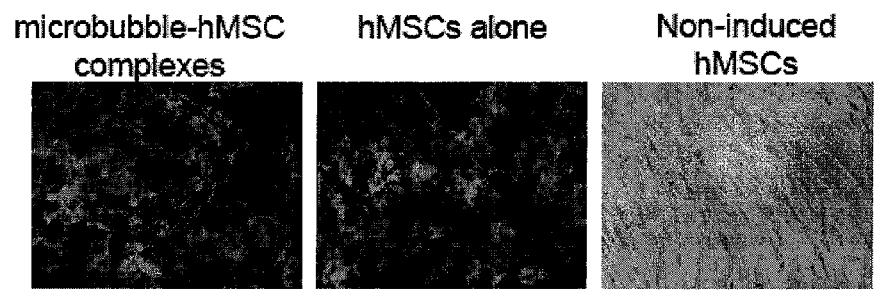
FIG. 41A presents exemplary photomicrographs comparing the effects of hMSCs and hMSC-microbubble complexes on osteogenic differentiation. Staining: Alizarin Red S.
FIG. 41B presents exemplary quantitative data of the photomicrographs in FIG. 41 demonstrating that hMSC-microbubble complexes had no effect on osteogenic differentiation as compared to hMSCs alone.
Figure 41:
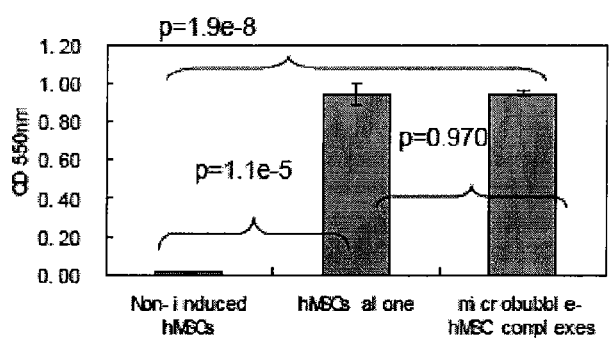
Figure 42:
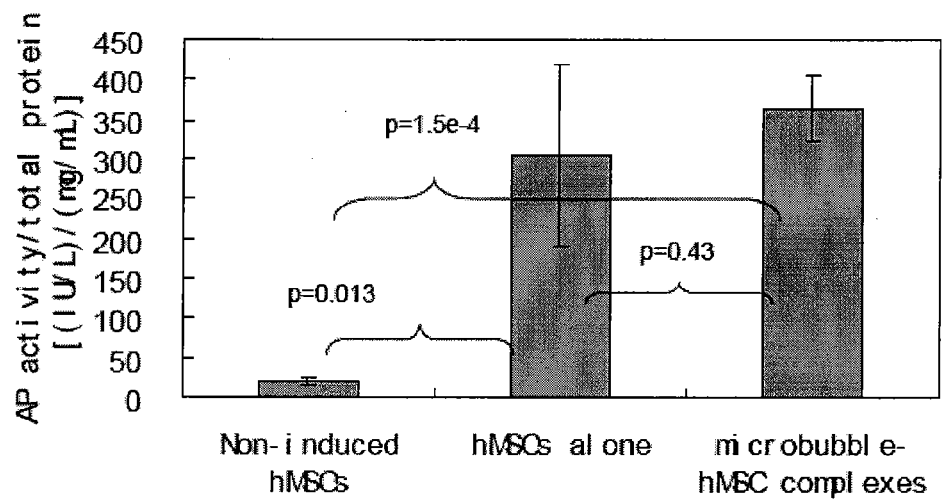
FIG. 42 presents exemplary data demonstrating that hMSC-microbubble complexes have no effect on alkaline phosphatase activity.
Figure 43:
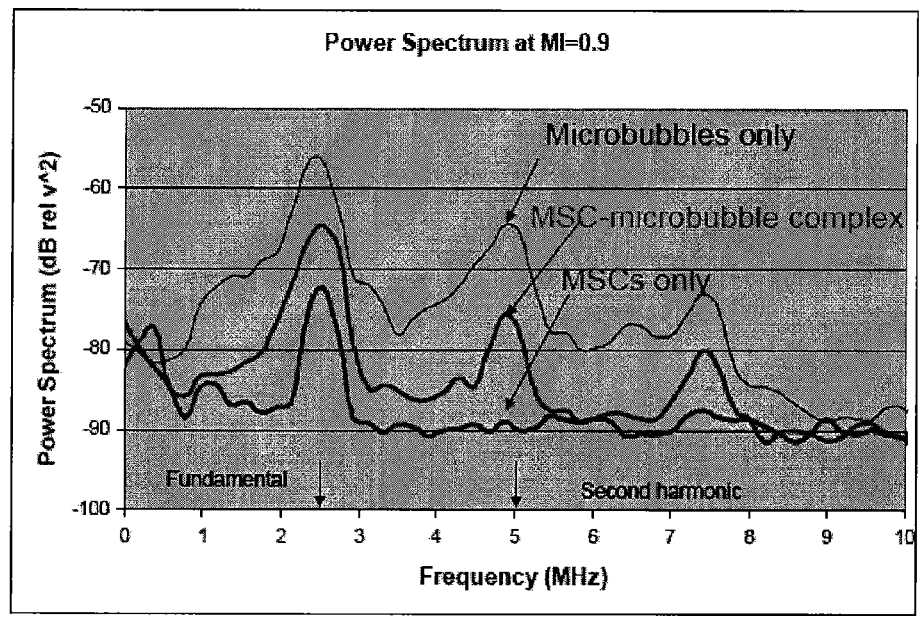
FIG. 43 presents exemplary data demonstrating the generation of second harmonic frequencies due to the induced oscillation of either microbubbles alone or hMSC-microbubble complexes. Panel A. MI=0.9. Panel B. MI=1.1.
Figure 43:
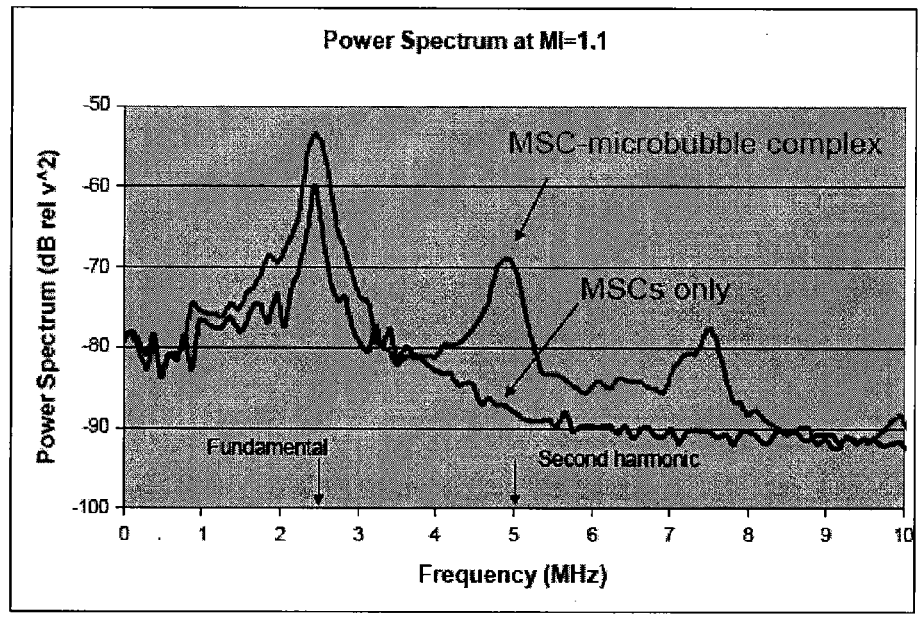

Other studies have demonstrated that hMSC:polymer contrast microbubble complexes do not: i) prevent the induced differentiation of adipocytes (See, FIGS. 39 and 40); ii) prevent osteogenic differentiation (See, FIG. 41); or iii) inhibit the activity of alkaline phosphatase (See, FIG. 42).

D. In Vivo Detection of Internalized Microbubbles Using Clinical Systems

In one embodiment, the present invention contemplates a method providing an MSC:polymer contrast microbubble complex and imaging the complex in vivo. In one embodiment, the method further comprises training to "learn" how to image the labeled cells in vivo—i.e. how to recognize what an image of microbubble-MSCs within tissue would "look like," whereby an independent standard is used to verify microbubble-MSC location, quantity, and viability. Although it is not necessary to understand the mechanism of an invention, it is believed that data collected from this method can be used to optimize ultrasound machine settings and/or processing algorithms. Further, in vivo imaging can determine the relationship between microbubble-MSC signals in tissue and MSC viability, and whether ultrasound can be used to track MSC migration. In vivo bioluminescence imaging may be used as an independent standard for localizing and quantifying MSCs.

hMSC:polymer contrast microbubble complexes (microbubble-hMSCs) or an identical number of MSCs only (control) are injected into a number of mice. Ultrasound imaging can be performed immediately after, and 4, 24, 48, 72 hours, and 7 days after injection. Ultrasound imaging may also be performed immediately after local intramuscular thigh injection of microbubble-hMSCs or hMSCs only, to facilitate positioning of the transducer. An independent in vivo method to localize hMSCs and guide ultrasound transducer placement is used to identify hMSC migration and to validate ultrasound images. In vivo bioluminescence whole body imaging can be used to localize the injected MSCs and can provide imaging information during days 1-7 after intramuscular MSC injection. One acute bioluminescent imaging technique detects luminescent signals for approximately 6 hours resulting from luciferase activity in luciferase positive cells following systemic administration of the substrate luciferin. For ultrasound imaging studies beyond 6 hours, MSCs harvested from transgenic mice expressing luciferase and green fluorescent protein are labeled. Microbubble-labeled luc+GFP+MSCs or luc+GFP+MSCs alone are injected intramuscularly into the thigh muscle of wild type mice. At 1 to 7 days after MSC delivery, luciferin are intraperitoneally injected and allowed to biodistribute. Anesthetized animals are placed within the light tight box of an IVIS200 imaging apparatus (Xenogen Corp) and images collected by a supercooled CCD camera and overlaid onto photographic images. Ultrasound imaging can be performed over the luminescent sites to determine how images appear in areas with validated localization of viable MSCs. Subsets of animals are euthanized after each imaging time point and fluorescence microscopy may be used to confirm MSC location, viability and density.

To more closely model intracoronary injections of cells, and determine the success of our method in tracking stem cell fate after intravascular delivery, these studies will also be performed after intra-arterial injection of luc+GFP+MSCs (with and without microbubble labeling).

Figure 35:
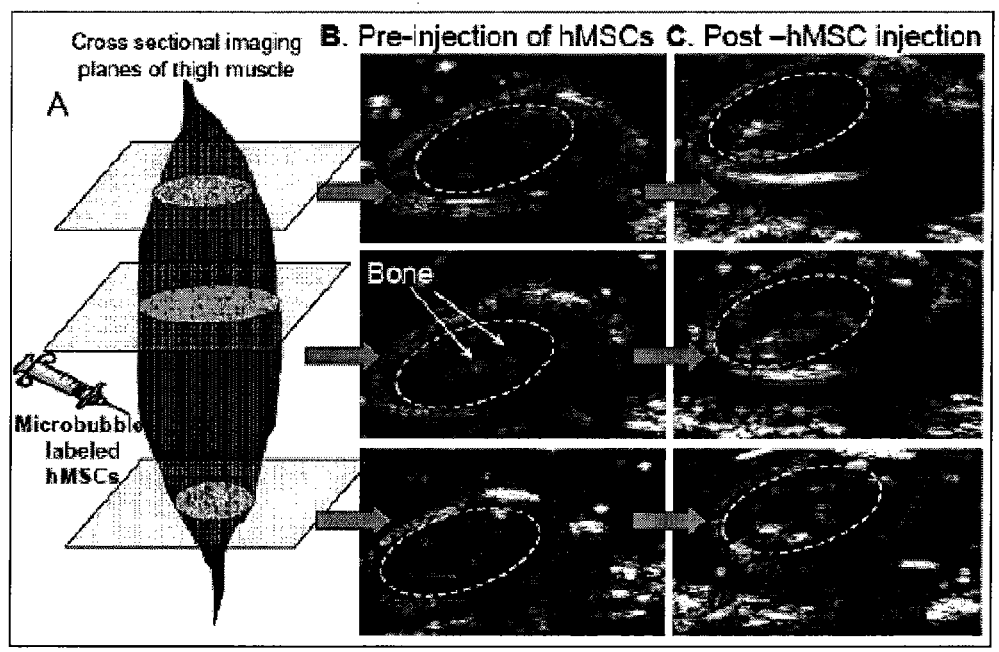
FIG. 35 presents exemplary data showing the effect of hMSCs with internalized polymer contrast microbubbles on in vivo mouse thigh muscle tissue. Panel A: Localization of injection site versus the three tomographic imaging planes. Panel B: Imaging before injection. Panel C: Imaging after injection. Yellow oval denotes inner portion of thigh muscle showing increased contrast enhancement after injection.
Figure 36:
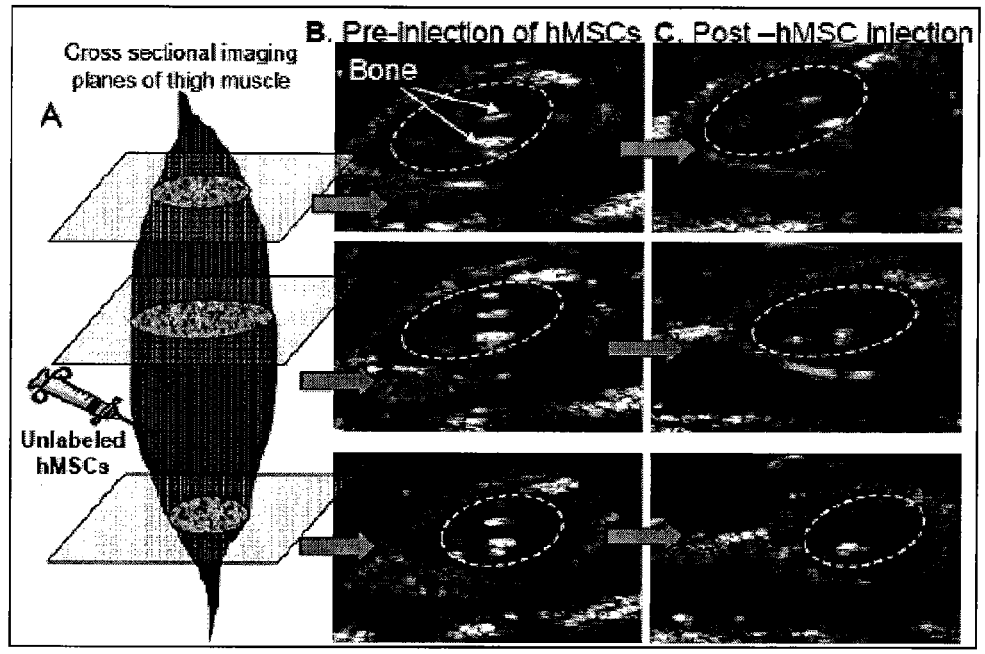
FIG. 36 presents exemplary data showing the effect of hMSCs alone on in vivo mouse thigh muscle tissue. Panel A: Localization of injection site versus the three tomographic imaging planes. Panel B: Imaging before injection. Panel C: Imaging after injection. Yellow oval denotes inner portion of thigh muscle showing no change in contrast enhancement after injection.
Figure 37:
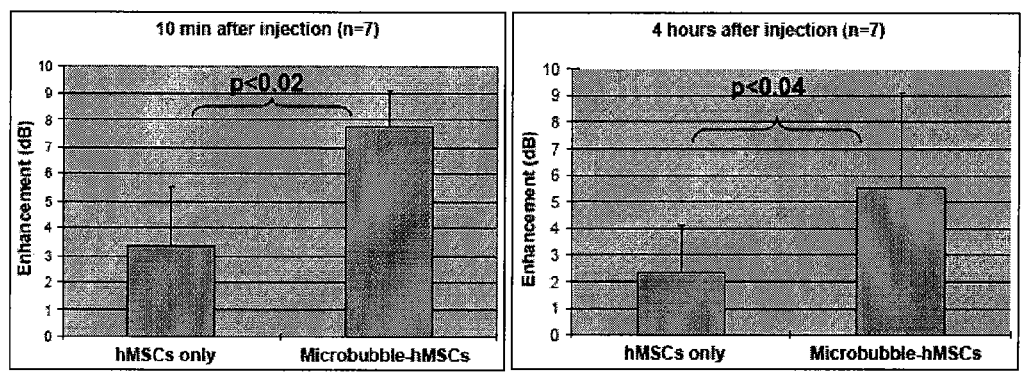
FIG. 37 presents exemplary data showing time course data following an in vivo injection of hMSCs with internalized polymer contrast microbubbles in accordance with FIG. 36. Left Panel: 10 minutes post-injection. Right Panel: 4 hours post-injection.

The data presented herein shows ultrasound imaging of hMSCs in vivo after intramuscular injection of microbubblehMSC complexes. Using the optimized microbubble formulation described above, microbubble-hMSCs or hMSCs alone were injected into thigh muscle of nude mice. See, FIG. 35, Panel A. Contrast pulse sequence ultrasound imaging was performed before and after injection. A tomographic proximal to distal cross-sectional ultrasound image of the muscle is presented before and after microbubble-labeled hMSC injection. See, FIG. 35, Panel B versus Panel C, respectively. A tomographic proximal to distal cross-sectional ultrasound image of the muscle is presented before and after injection of hMSCs alone. FIG. 36, Panel B versus Panel C, respectively. A localized muscle opacification is observed after microbubble-labeled hMSC injection that is not seen after injection of unlabeled hMSCs. FIG. 35 Panel C versus FIG. 36 Panel C, respectively.

E. Controlling Signal-to-Noise Ratios

A signal-to-noise ratio of the presently disclosed imaging technique can be determined to detect circulating microbubbles even if it is not known a priori where an observation should be made. For example, the bioluminescent imaging mouse studies presented herein demonstrate how to recognize unique microbubble-MSC signals apart from tissue when it is known where they are located (i.e., for example, the implanted tumor site). However, in clinical practice, an independent in vivo standard would not be available for locating the microbubble:cell complexes, thereby preventing an efficient use of regional ultrasound scans. One approach to improve microbubble:cell complex localization is to improve detection sensitivity.

Figure 38:
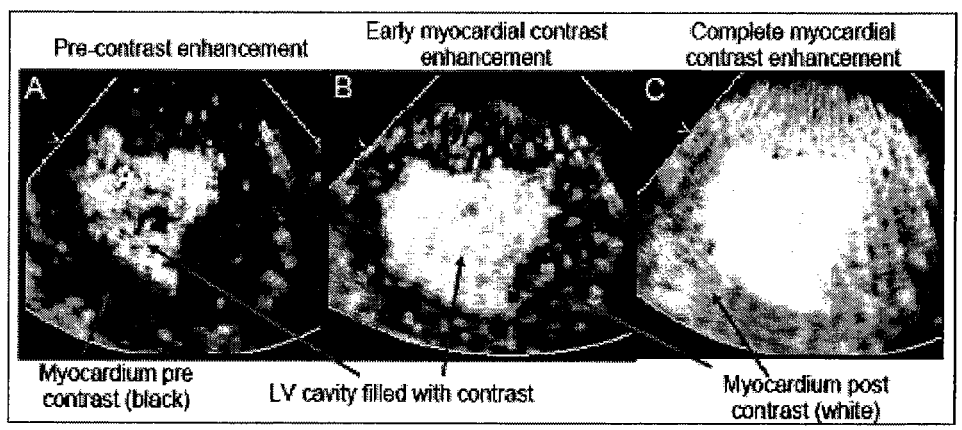
FIG. 38 presents exemplary data showing improved canine left ventricle myocardial signal-to-noise ratio with contrast echocardiography in short axis images after intravenous injection of polymer contrast microbubbles. Panel A: Pre-contrast: myocardium is black (e.g., unenhanced) with non-linear imaging. The left ventricle cavity is white as the microbubbles are injected. Panel B: Opacification of the myocardium begins as the microbubbles enter the coronary microcirculation. Panel C: Full opacification of the myocardium within seconds after microbubble injection.

One method for improved detection sensitivity has been demonstrated in the myocardium. The data presented herein demonstrates detection of microbubble-MSCs above tissue backscatter in myocardial tissue. See, FIG. 35. With non-linear imaging, myocardial tissue appears largely black in these images, and microbubble-MSCs generate a harmonic that can be distinguished from surrounding tissue. See, FIG. 29. A sequence of ultrasound images were taken in a dog left ventricle in the short axis plane where a contrast agent was injected intravenously. It was shown that the contrast agent entered the left ventricular cavity, followed by early myocardial contrast, and full myocardial opacification seconds later. See, FIG. 38, Panels A-C, respectively. The brightness of the contrast agent is distinctive against the dark myocardium as it appears prior to entry of microbubbles. These images suggest that a signal/noise ratio using the presently disclosed method allows detection of entry and migration of microbubble-labeled MSCs into tissues such as the myocardium.

VI. Clinical Treatments

In some embodiments the present invention contemplates methods for treating various diseases and/or injuries using biological cells. In one embodiment, the progress of such treatment may be monitored by interalizing the biological cells with polymer contrast microbubbles before administration to the patient. Consequently, the fate of the biological cells may be determined, with precision, as to their location and status. For example, one therapeutic biological cell may comprise a stem cell. Alternatively, a therapeutic biological cell may comprises a non-stem cell. In one embodiment, the non-stem cell comprises a cancer cell, wherein the growth and or metastasis of a tumor may be detected and/or monitored using serial ultrasound imaging.

A. Cardiovascular Disease

With the rapid increase of reported cases of biological cells (i.e., for example, stem cells) being used to treat cardiovascular disease, it has become apparent that an urgent need exists to track cells in vivo during clinical trials. For example, stem cell therapy for heart failure addresses an important problem in clinical medicine. Heart failure is a major cause of morbidity and mortality in the United States. The rates of new and recurrent heart failure events increase substantially with age. In patients aged 65 and older, congestive heart failure is the single most frequent cause of hospitalization in the United States. Despite substantial advances in the clinical management of heart failure, the diagnosis continues to carry a grave prognosis with an overall 5-year mortality rate of ~50%. This rate is substantially worse in more severely affected patient subsets. An understanding of the role of stem cells in repopulating damaged areas in the heart would help target these diseased areas. Britten et al., "Infarct remodeling after intracoronary progenitor cell treatment in patients with acute myocardial infarction (TOPCARE-AMI): mechanistic insights from serial contrast enhanced magnetic resonance imaging" *Circulation* 108:2212-2218 (2003). The problem of imaging small numbers of cells in the living subject is not limited to stem cell-based treatments in cardiology but has broad applicability in oncology, immunology, and transplantation.

Adult bone marrow-derived mesenchymal stem cells (MSCs) may be useful to treat heart diseases resulting from cardiomyocyte death. Pittenger et al., "Multilineage potential of adult human mesenchymal stem cells" *Science* 284:143-147 (1999); and Psaltis et al., "Concise Review: Mesenchymal stromal cells: Potential for cardiovascular repair" *Stem Cells* 26:2201-2210 (2008). Ischemic heart disease leading to myocardial infarction and congestive heart failure may exact a significant toll on morbidity and mortality in Western nations and constitute a major economic liability to health systems and society. Acute myocardial infarction is believed to result in the death of cardiomyocytes and decreased left ventricular function. Moreover, the loss of myocardial cell mass is believed to lead to adverse left ventricular remodeling, extending the impairment in contractile function beyond the borders of the infarct itself. Despite the benefits of current pharmacologic and mechanical therapies for congestive heart failure, none of these replete the cardiomyocyte content of the infarcted region. Furthermore, the heart has been reported to have a limited capability for self-repair or regeneration. Perin et al., "Transendocardial, autologous bone marrow cell transplantation for severe, chronic ischemic heart failure" *Circulation* 107:2294-2302 (2003); and Murry et al., "Haematopoietic stem cells do not transdifferentiate into cardiac myocytes in myocardial infarcts" *Nature* 428:664-668 (2004). Consequently, the art is in need of a method to solve these limitations such that new treatment strategies can repair the heart, including delivery of reparative cells to injured tissue. In some embodiments, the present invention contemplates methods and compositions to provide solutions to these problems.

Cell-based therapies has been considered a new approach to repair or regenerate tissue damaged by myocardial infarction. Bone-marrow derived cells have been suggested as potential candidates for this purpose as reported in clinical trials of intracoronary infusion of autologous unfractionated bone marrow. Fuchs et al., "Safety and feasibility of transendocardial autologous bone marrow cell transplantation in patients with advanced heart disease" *Am J Coll Cardiol* 97:823-829 (2006). Although it is not necessary to understand the mechanism of an invention, it is believed that how hematopoietic stem cells actually engraft remains controversial. Murry et al., "Haematopoietic stem cells do not transdifferentiate into cardiac myocytes in myocardial infarcts" *Nature* 428:664-668 (2004); and Mazhari et al., "Mechanisms of action of mesenchymal stem cells in cardiac repair: potential influences on the cardiac stem cell niche" *Nature*

*Clinical Practice Cardiovasc Med* 4:S21-S25 (2007). More recently, a subpopulation of bone marrow cells (i.e., for example, mesenchymal stem cells; MSCs), have been studied for their cardiac reparative properties. Studies in animal models of infarct or ischemia have reported diverse biological effects from delivery of bone-marrow derived MSCs, including reduction of infarct size, improvement of ventricular function, increased vascular density, and improved myocardial perfusion. Amado et al., "Cardiac repair with intramyocardial injection of allogeneic mesenchymal stem cells after myocardial infarction" *PNAS* 102:11474-11479 (2005); Toma et al., "Human mesenchymal stem cells differentiate to a cardiomyocyte phenotype in the adult murine heart" *Circulation* 105:93-98 (2002); Nagaya et al., "Transplantation of mesenchymal stem cells improves cardiac function in a rat model of dilated cardiomyopathy" *Circulation* 112:1128-1135 (2005). The mechanisms mediating the therapeutic benefits of MSC therapy are incompletely understood, and previous speculation that exogenous cells remuscularize the heart through transdifferentiation into myocytes has been recently questioned. Mazhari et al., "Mechanisms of action of mesenchymal stem cells in cardiac repair: potential influences on the cardiac stem cell niche" *Nature Clinical Practice Cardiovasc Med* 4:S21-S25 (2007). Recent data suggests that MSC stimulate paracrine release of growth factors and cytokines that promote angiogenesis, prevent cardiomyocyte apoptosis and/or stimulate endogenous self-repair. Kinnaird et al., "Marrow-derived stromal cells express genes encoding a broad spectrum of arteriogenic cytokines and promote in vitro and in vivo arteriogenesis through paracrine mechanisms" *Circ Res* 94:678-685 (2004). MSCs may also evade immune detection renders allogeneic grafting a possibility. Psaltis et al., "Concise Review: Mesenchymal stromal cells: Potential for cardiovascular repair" *Stem Cells* 26:2201-2210 (2008).

Despite these improvements, there are still no in vivo methods to sequentially track administered biological cells in mammalian populations. One advantage to these tracking methods would be to optimize treatment protocols. Recent clinical trials investigating the effects of cell therapies in patients have been limited to measuring parameters such as the biodistribution of the cells, their short/long term viability, and the extent of cell engraftment. Boyle et al., "Is stem cell therapy ready for patients? Stem cell therapy for cardiac repair—Ready for the next step" *Circulation* 114:339-352 (2006); Bartunick et al., "Intracoronary injection of CD133-positive enriched bone marrow progenitor cells promotes cardiac recovery after recent myocardial infarction: feasibility and safety" *Circulation* 112:1178-1183 (2005); and Beeres et al., "Role of imaging in cardiac stem cell therapy" *J Am Coll Cardiol* 49:1137-1148 (2007). These studies do not address unsolved medically relevant questions, including, but not limited to: i) What are the optimal therapeutic cell type and route and timing of delivery?; and ii) How many cells should be delivered?. Answers to such questions requires a method for in vivo tracking of stem cell fate using non-invasive imaging not available to those in the art until the present invention.

1. Internalized hMSC Tracking after Myocardial Infarction

In one embodiment, the present invention contemplates a method comprising performing serial echocardiographic MSC imaging for tracking biological cells after in vivo administration. In one embodiment, the administration is systemic. In one embodiment, the administration is local. In one embodiment, the local administration comprises intracoronary administration. In one embodiment, the local adminis- tration comprises endocardial administration. In one embodiment, the administration comprises a targeting moiety.

In regards to treating myocardial infarction with a biological cell (i.e., for example, an MSC), establishing an optimal route for cell delivery remains an open question. Comparative evaluation of delivery routes should serially assess parameters including, but not limited to, the fate, retention, and viability of MSCs. Although it is not necessary to understand the mechanism of an invention, it is believed that ultrasound contrast cell tracking technology as disclosed herein enables evaluation and comparison of different routes for administering MSCs. For example, methods using MSC delivery were designed to compare intracoronary (i.c.) vs. endocardial (e.c.) routes of MSC delivery. These methods allowed a determination of both MSC cell fate and functional clinical outcomes in swine with experimental myocardial infarction. A previous study in swine compared retention of intracoronary versus endocardial iridium nanoparticle-labeled MSCs delivered immediately post reperfusion. Freyman et al., A quantitative, randomized study evaluating three methods of mesenchymal stem cell delivery following myocardial infarction" *Eur Heart J* 1-9 (2006). This report showed that post mortem measurement of retained iridium 14 days later could not distinguish retention of the label by viable engrafted MSCs vs. release of the label by dying MSCs, nor serially track MSC trafficking during the 14 days following delivery. Finally, long term functional outcomes of the MSC therapy could not be measured, since assessment of the short term fate of injected MSCs required early post-mortem analysis.

Acute myocardial infarction can be produced in female domestic swine by 1 hr occlusion of the mid left anterior descending artery (LAD) using a percutaneously inserted angioplasty balloon. 3 days after reflow. The animals can then be randomized to one of 4 treatment groups (n=8 per group) to receive $50 \times 10^6$ microbubble-labeled GFP-expressing male swine bone marrow derived MCSs: 1) intracoronary (LAD) infusion; 2) endocardial injection to the peri-infarct area using NOGA mapping; 3) intracoronary infusion of vehicle control; and 4) endocardial injection of vehicle control. On the day of LAD occlusion, ultrasound imaging should be performed pre-occlusion, pre-treatment (post-infarct), and post-treatment immediately, and 4 and 8 hours after MSC delivery. Follow-up echocardiography may then be done at 2 and 7 days after MSC treatment, and weekly thereafter for approximately 2 months. Imaging evaluations may comprise 2D and/or 3D echocardiograms, tissue Doppler, and/or speckle tracking. Such techniques are believed to be capable of evaluating cardiac mechanical function and MSC imaging using harmonic methods discussed herein. The delivery route comparisons are designed to have various outcome measures. See, Table 7.

TABLE 7

Outcome Measures For Comparing Routes Of Administration

| Outcome Measurement | Evaluation Method |
| --- | --- |
| Left ventricular (LV) geometry | 3D echocardiography for LV size, volume, mass (serial) |
| Left ventricular mechanics | Echocardiography for ejection fraction and segmental wall motion; tissue Doppler and speckle tracking for LV strain (serial) |
| In vivo MSC trafficking | Serial echocardiography of microbubble-MSCs for localization and quantification of viable MSCs (i.e., for example, heart, liver, spleen) |
| Long term MSC engraftment | Immediate ante-mortem echocardiography of MSCs; compare with post mortem FISH |

TABLE 7-continued

Outcome Measures For Comparing Routes Of Administration

| Outcome Measurement | Evaluation Method |
|---|---|
| (~2 month follow-up) | staining and GFP microscopy of heart, liver, spleen |
| Infarct size (% risk area) | Post mortem triphenyl tetrazolium chloride stain; hematoxylin & eosin stain for extent of fibrosis in infarct and border zones |
| Microvascular flow | LAD Doppler wire one hour post MSC delivery Histologic evidence of no reflow (post mortem) |

Previous reports have demonstrated both NOGA mapping and endocardial delivery of MSCs, both in swine models as well as in human clinical trials of MSC therapy. Patel et al., "Improved Cell Survival in Infarcted Myocardium Using a Novel Combination Transmyocardial Laser and Cell Delivery System" *Cell Transplantation* 16:899-906 (2007); and Toma et al., "Positive effect of darbepoetin on peri-infarction remodeling in a porcine model of myocardial ischemia-reperfusion" *J Mol Cell Cardiol* 43(2):130-136 (2007). Contrast ultrasound imaging of the heart in large animals has also been reported. Villanueva et al., Detection of coronary artery stenosis using power Doppler imaging" *Circulation* 103:2624-2630 (2001). Recently, one report shows intravital microscopic observations of microvascular plugging and flow cessation after intra-arterial delivery of MSCs, in which most MSCs die within 48 hrs of injection and a small percentage engraft in a peri-vascular location. Toma et al., "Fate of culture-expanded mesenchymal stem cells in the microvasculature: in vivo observations of cell kinetics" *Circ Res.* 104:398-402 (2009). While the observed degree of engraftment may be sufficient to support the putative paracrine functions of MSCs, the effect may be offset by consequences of microvascular plugging. For example, endocardial delivery may produce less engraftment but this advantage may be offset by avoidance of microvascular plugging. Freyman et al., A quantitative, randomized study evaluating three methods of mesenchymal stem cell delivery following myocardial infarction" *Eur Heart J* 1-9 (2006).

B. Injured Cardiovascular Vessels

In one embodiment, the present invention contemplates administering endothelial stem cells and/or endothelial progenitor cells comprising internalized microbubbles to promote vessel wall healing and to track the progress of the healing by ultrasound imaging that is capable of imaging cell attachment and growth.

Injury to cardiovascular vessels can occur by a variety of insults, most notably, certain medical procedures. For example, medical procedures including, but not limited to, angioplasty or stenting may occur in the denuding of endothelial cells from the cardiovascular vessel wall. Alternatively, some surgical procedures may also leave injury to cardiovascular vessels that undergo a post-surgical healing process. Sometimes the healing process may comprises stenosis or restenosis characterized by a narrowing of the vessel.

Restenosis and/or stenosis is believed to result from mechanisms including, but not limited to, inflammation or cell proliferation at the site of injury in the stented or otherwise injured vessel wall. Drugs such as paclitaxel and sirolimus are being currently used in drug eluting stents to prevent scar tissue growth and neointima formation. In general, these drugs were chosen for potency, and general effects on suppressing cellular growth without targeting the underlying vascular disease.

Restenosis or stenosis is also believed to result from injury to an arterial wall during stent implantation and occurs within 6-12 months of the procedure. Classic restenosis occurring with bare metal stents (i.e., for example, non-drug coated) comprises progressive, instead of rapid, symptoms and affects 25-30% of the treated patients.

C. Diabetes

In one embodiment, the present invention contemplates transplanting pancreatic cells comprising internalized microbubbles to promote organ regeneration and to track the progress of the organ regeneration by ultrasound imaging.

Diabetes is a chronic (lifelong) disease marked by high levels of sugar in the blood. Insulin is a hormone produced by the pancreas to control blood sugar. Diabetes can be caused by too little insulin, resistance to insulin, or both. People with diabetes have high blood sugar. because: i) their pancreas does not make enough insulin and/or ii) their muscle, fat, and liver cells do not respond to insulin normally.

Type 1 diabetes is usually diagnosed in childhood. Many patients are diagnosed when they are older than age 20. In this disease, the body makes little or no insulin. Daily injections of insulin are needed. The exact cause is unknown. Genetics, viruses, and autoimmune problems may play a role.

Type 2 diabetes is far more common than type 1. It makes up most of diabetes cases. It usually occurs in adulthood, but young people are increasingly being diagnosed with this disease. The pancreas does not make enough insulin to keep blood glucose levels normal, often because the body does not respond well to insulin. Many people with type 2 diabetes do not know they have it, although it is a serious condition. Type 2 diabetes is becoming more common due to increasing obesity and failure to exercise.

Gestational diabetes is high blood glucose that develops at any time during pregnancy in a woman who does not have diabetes.

There are many risk factors for type 2 diabetes including, but not limited to, age over 45 years, family history, heart disease, high blood cholesterol level, obesity, or lack of exercise. Diabetic symptoms may include, but not be limited to, blurry vision, excessive thirst, fatigue, frequent urination, hunger, or unexplained weight loss Examination and testing for diabetes usually begins with a urine analysis to determine glucose and ketones levels. Diagnosing diabetes may be determined by comparing the following factors:

i) fasting blood glucose level—diabetes is diagnosed if higher than 126 mg/dL on two occasions. Levels between 100 and 126 mg/dL are referred to as impaired fasting glucose or pre-diabetes. These levels are considered to be risk factors for type 2 diabetes and its complications.

ii) oral glucose tolerance test—diabetes is diagnosed if glucose level is higher than 200 mg/dL after 2 hours. (This test is used more for type 2 diabetes.)

iii) random (non-fasting) blood glucose level—diabetes is suspected if higher than 200 mg/dL and accompanied by the classic diabetes symptoms of increased thirst, urination, and fatigue. (This test should be confirmed with a fasting blood glucose test.).

D. Cancer

In one embodiment, the present invention contemplates contacting cancer cells with microbubbles, such that the microbubbles are internalized into the cancer cells to track the progress of cancer therapy and to detect non-palpable metastasis by ultrasound imaging.

Cancer is the uncontrolled growth of abnormal cells in the body. Cancerous cells are also called malignant cells. Cancer grows out of normal cells in the body. Normal cells multiply when the body needs them, and die when the body doesn't need them. Cancer appears to occur when the growth of cells in the body is out of control and cells divide too quickly. It can also occur when cells "forget" how to die.

In one embodiment, the present invention contemplates imaging cancer progression in almost any organ or tissue, such as the lung, breast, colon, liver, prostate, breast, skin, bones, brain, nerve tissue, cervical, lymph, white blood cells, ovary, testes, thyroid, or uterus. There are many causes of cancers, including, but not limited to, chemicals (i.e, for example, benzene), poisons (i.e., for example, derived from mushrooms, or aflatoxins), viruses, radiation, sunlight, or tobacco.

Symptoms of cancer depend on the type and location of the tumor. For example, lung cancer can cause coughing, shortness of breath, or chest pain. Colon cancer often causes diarrhea, constipation, and blood in the stool. Some cancers may not have any symptoms at all. In certain cancers, such as gallbladder cancer, symptoms often do not start until the disease has reached an advanced stage. In general, symptoms occurring with most cancers include, but are not limited to, chills, fatigue, fever, loss of appetite, malaise, night sweats, or weight loss. Like symptoms, the cancer diagnosis varies based on the type and location of the tumor. Common tests include the following, biopsy, blood chemistries, x-ray, complete blood count, or computerized tomography.

Currently cancer treatment also varies based on the type of cancer and its stage. The stage of a cancer refers to how much it has grown and whether the tumor has spread from its original location. If the cancer is confined to one location and has not spread, the most common goals for treatment are surgery and cure. This is often the case with skin cancers, as well as cancers of the lung, breast, and colon. If the tumor has spread to local lymph nodes only, sometimes these can also be removed. If surgery cannot remove all of the cancer, the options for treatment include radiation, chemotherapy, or both. Some cancers require a combination of surgery, radiation, and chemotherapy.

E. Neurodegenerative Diseases

In one embodiment, the present invention contemplates contacting nerve cells with microbubbles, such that the microbubbles are internalized within the nerve cells to track the progress of neuronal regeneration and/or neurodegeneration by ultrasound imaging.

Alzheimer's Disease (AD) is a progressive neurodegenerative disorder characterized by cognitive decline, irreversible memory loss, disorientation and language impairment. It is the most common cause of dementia in the United States. AD can strike persons as young as 40-50 years of age, but because the presence of the disease is difficult to detect without histopathological examination of brain tissue, the time of onset in living subjects is unknown. The prevalence of AD increases with age, with estimates of the affected population as high as 40% by ages 85-90.

AD is only definitively diagnosed through postmortem examination of brain tissue, when pathologists examine the brain tissue for the presence of abundant senile plaques (SPs) composed of amyloid-.beta. (A.beta.) peptide aggregates and neurofibrillary tangles (NFTs) formed by filaments of highly phosphorylated tau proteins. An amyloid deposit is formed by the aggregation of amyloid peptides, followed by the further combination of aggregates and/or amyloid peptides. The fibrillar aggregates of amyloid peptides, A.beta.1-40 and A.beta.1-42, are major metabolic peptides derived from amyloid precursor protein that are found in senile plaques and cerebrovascular amyloid deposits in AD patients.

Parkinson's Disease (PD), another common neurodegenerative disease, is a progressive disorder characterized by resting tremors, bradykinesia, muscular rigidity, and postural instability. PD affects men and women without distinction, regardless of social, ethnic, economic or geographic backgrounds. PD usually develops after the age of 60, though 15% of those diagnosed are under the age of 50. Family history of PD is an etiological factor for 5-10% of patients diagnosed with the disease, yet only 1% of cases have been shown to be clearly familial. It is estimated that 1.5 million Americans are currently living with Parkinson's Disease.

Dementia with Lewy Bodies (DLB) is a progressive neurodegenerative disorder characterized by symptoms that fluctuate between various degrees of manifestation. Such symptoms include progressive dementia, Parkinsonian movement difficulties, hallucinations, and increased sensitivity to neuroleptic drugs. As with AD, advanced age is considered to be a risk factor for DLB, with average onset typically between the ages of 50-85.20% of all dementia cases are caused by DLB and over 50% of PD patients develop Parkinson's Disease Dementia (PDD), a type of DLB. DLB may occur alone or in conjunction with other brain abnormalities, including those involved in AD and PD, as mentioned above. Currently, conclusive diagnosis of DLB is made during postmortem autopsy.

PD and DLB share an etiology of dopamine deficiency, which is correlated with the death of dopaminergic neurons in the substantia nigra. Dopamine is a neurotransmitter that allows for smooth, coordinated function of the body's muscles and movement. The cause of dopaminergic neuronal death in PD is unknown, but it is recognized that in DLB, abnormal protein deposits called Lewy body proteins or "Lewy bodies" are instrumental in the death of dopaminergic neurons. Lewy bodies occur mostly in the substantia nigra and locus ceruleus sections of the brain stem and also, to a lesser extent, in the subcortical and cortical regions of the brain. Because of this specific localization in the brain, Lewy bodies also interfere with the production of acetylcholine, causing disruption in perception, thinking and behavior. Lewy bodies are also typically considered to be a type of SP, as Lewy bodies are made up of aggregated .alpha.-synuclein protein deposits.

An additional etiology of neurodegeneration can be a mixture of pathologies that involves a component of microvascular, or perfusion, deficits in the brain. Commonly referred to as "mixed dementia", this type of neurodegeneration often involves both perfusion deficits as well as amyloid plaque pathology. Different meanings have been associated with the term mixed dementia. One definition of mixed dementia encompasses a combination of AD and other pathologies such as hypothyroidism, or vitamin B-12 deficiency. However, mixed dementia is most commonly refers to the coexistence of AD and vascular dementia (VaD). Mixed dementia is clinically important because the combination of AD and VaD may have a greater impact on the brain than either by itself. Mixed dementia is traditionally difficult to diagnose, although symptoms are generally similar to those of AD or VaD or a combination of the two.

Because of the central role of the presence of A.beta. plaques in AD and death of dopaminergic neurons in PD and DLB, there has been a wide interest in developing radiolabeled ligands that bind to and allow imaging of such abnormalities. Several radioisotopically-labeled A.beta.-aggregate-specific ligands have been reported for the imaging of amyloid plaque in the living subject using positron emission tomography (PET) or single photon emission computed tomography (SPECT). These ligands are mainly targeted to nigrostriatal neurons and D2/D3 receptors in the brain. Examples of such radioisotopically-labeled A.beta.-aggregate-specific ligands include [(99m)Tc]TRODAT-1 and [(123)I]IBZM, among many others. In addition, several radiopharmaceuticals have been used for PET or SPECT imaging of regional cerebral perfusion. PET radiopharmaceuticals such as $^{15}$O-labeled water ($H_2^{15}O$) and. $^{13}$N-ammonia ($^{13}NH_3$) have been employed for perfusion imaging. SPECT radiopharmaceuticals such as Tc-99m HMPAO and Tc-99m Bicisate are also used as cerebral perfusion agents.

Dual-isotope imaging techniques have been employed in trials including parathyroid-studies to detect the existence of an adenoma on the thyroid and in myocardial imaging studies of perfusion and myocardial tissue viability. Additionally, in the brain, a simultaneous $^{18}$F-FDG and $^{99m}$Tc-HMPAO SPECT imaging technique has been utilized to image selected areas in the neuroanatomy of anxiety and depression such as the hippocampus, basal ganglia and gyri temporales superiores. There have also been studies employing a dual SPECT imaging technique with [$^{99m}$Tc]TRODAT-1 and [$^{123}$I]IBZM to image nigrostriatal neurons and D2/D3 receptors.

VII. Pharmaceutical Compositions and Formulations

The present invention further provides pharmaceutical compositions (e.g., a biological cell comprising an internalized polymer contrast microbubble). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

VIII. Kits

In another embodiment, the present invention contemplates kits for the practice of the methods of this invention. The kits preferably include one or more containers containing a biological cell. The kit can optionally include a polymer contrast microbubble comprising an acoustically active gas. The kit can optionally include a stem cell. The kit can optionally include a non-stem cell. The kit can optionally include biological cells derived from tissues including, but not limited to, brain, heart, vascular, lung, liver, kidney, muscle, bone marrow, pancreas, uterus, bladder, testicle, and/or prostate. The kit can optionally include a pharmaceutically acceptable excipient and/or a delivery vehicle. The reagents may be provided suspended in the excipient and/or delivery vehicle or may be provided as a separate component which can be later combined with the excipient and/or delivery vehicle.

The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in: i) internalizing a microbubble into a biological cell; ii) administering a biological cell comprising an internalized microbubble; and iii) imaging the administered biological cells. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXPERIMENTAL

Example I

Single Wall Polymer Contrast Microbubble Fabrication

Single wall polymer contrast microbubbles may be fabricated by double-emulsion (Water/Oil/Water) and solvent evaporation methods. Briefly, 300 mg of poly(L-lactide ((PLLA) (MW 75,000-120,000) or poly(lactide-co-glycolide) (PLGA) (50:50) (IV=0.38 dl/g) are dissolved in 10-25 ml dichloromethane. 2 ml of ammonium bicarbonate (200 mg/ml) solution is emulsified with polymer solution with a sonicator. This W/O emulsion may be dropped into PVA solution (200 ml, 1% w/v) and homogenized at 10,000 rpm for 1 hour. The resulting W/O/W emulsion is continually stirred at 500-600 rpm at room temperature for another 4 hours. Finally, the resulting microbubbles are collected by centrifugation, washed five times with deionized water, and freeze-dried using a lyophilizer to sublimate the encapsulated water and get the final products. The dried microbubbles were then maintained under vacuum conditions for at least 2 hours to complete the drying process. Purging may also be performed using perfluorocarbon gas at an adjusted rate throughout the airtight system.

The prepared perfluorocarbon-filled single walled microbubble contrast agent may then be sealed and stored under a headspace filled with perfluorocarbon gas. The physical properties of the microbubbles can be tailored by varying the shell materials composition, incorporating other components, adjusting the ratio of inner water phase to oil phase, changing the concentration of polymer solution and controlling the solvent evaporation rate, with resulting differences in acoustical activity, stability and ability to be internalized by or attached on stem cells.

By adjusting the components of the materials and fabrication parameters, microbubbles maybe made with different inner structures (i.e., for example, porous or hollow) so as to change characteristics including but not limited to, biodegradability, and acoustical activity. The data presented herein demonstrates that polymer microbubbles can be internalized by biological cells without influencing viability. In other embodiments, cell attachment to the microbubble surface may be improved by manipulating microbubble surface charges (i.e, for example, a net positive or a net negative) or binding a targeting ligand.

Example II

Polymer Contrast Microbubble Internalization

A polymer contrast microbubble suspension was transferred to a centrifuge tube and centrifuged at 1500 rpm for 10 minutes. After collecting the floating microbubbles from the supernatant and counting the number of the microbubbles with a Coulter Counter, microbubble suspension was added to a Petri dish containing media and cells which have been cultured to confluence. The Petri dish was covered with sterile paraffin film before the lid was added on top of the paraffin film. Then the whole Petri dish is turned upside down to facilitate microbubbles contact with the cells via buoyancy forces. The cells and microbubbles were kept in an incubator for 2 hours before the Petri dish is turned back to the normal position and left in the incubator overnight. After incubation, the cell-microbubble complexes were lifted using Trypsin and free microbubbles are separated by centrifugation. Several rounds of washing may be necessary to make sure there is no free microbubble in the final suspension. The final cell-microbubble association was re-suspended into culture media for subsequent testing.

Although it is not necessary to understand the mechanism of an invention, it is believed that the cellular uptake of microbubbles by either stem cells or non-stem cells may not be mutually exclusive. Normally, the uptake of particles by cells is size dependent (Langer R, et al, Adv. Mater. 2008, 20, 2285-2291). For those particles under 1 micron, the cell uptake could be receptor mediated endocytosis (K. Y. Win, S. S. Feng, Biomaterials 2005, 26, 2713; M. P. Desai, V. Labhasetwar, E. Walter, R. J. Levy, G. L. Amidon, Pharm. Res. 1997, 14, 1568; B. D. Chithrani, A. A. hazani, W. C. Chan, Nano Lett. 2006, 6, 662; L. Lacerda, G. Pastorin, D. Gathercole, J. Buddle, M. Prato, A. Bianco, K. Kostarelos, Adv. Mater. 2007, 19, 1480). For a microbubble population having an average diameter of approximately 100 nanometer to 10 microns, but more preferably between approximately 2-3 microns, it is generally believed that the microbubbles are compatible with most cellular non-specific endocytotic processes. The biological cells comprising internalized microbubbles prepared herein utilized mechanical forces (i.e., for example, inversion of a covered Petri dish) to maximize the interaction between extracellular endocytosis sites and a microbubble.

Example III

Preparation of a Bi-Layer Polymer Contrast Microbubble

Two solutions are prepared, the first being an aqueous solution of an outer biomaterial. The second is a solution of a polymer which is used to form the inner layer, in a relatively volatile water-immiscible liquid which is a solvent for the polymer, and a relatively non-volatile water-immiscible liquid which is a non-solvent for the polymer. The relatively volatile water-immiscible solvent is typically a C5-C7 ester, such as isopropyl acetate. The relatively non-volatile water-immiscible non-solvent is typically a C6-C20 hydrocarbon such as decane, undecane, cyclohexane, cyclooctane and the like. In the second solution containing the polymer for the inner layer, the polymer in water-immiscible solvents are combined so that the polymer fully dissolves and the two solvents are miscible with agitation. The polymer solution (organic phase) is slowly added to the biomaterial solution (aqueous phase) to form a liquid foam. Typically about three parts of the organic polymer solution having a concentration of about 0.5 to 10 percent of the polymer is added to one part of the aqueous biomaterial solution having a concentration of about 1 to 20 percent of the biomaterial. The relative concentrations of the solutions and the ratio of organic phase to aqueous phase utilized in this step essentially determine the size of the final microparticle and wall thickness. After thorough mixing of the liquid foam, it is dispersed into water and typically warmed to about 30-35° C. with mild agitation. While not intending to be bound by a particular theory, it is believed that the biomaterial in the foam disperses into the warm water to stabilize an emulsion of the polymer in the organic phase encapsulated within a biomaterial envelope. To render the biomaterial envelope water insoluble, a cross linking agent, such as glutaraldehyde, is added to the mixture to react with the biomaterial envelope and render it water insoluble, stabilizing the outer shell. Other cross-linking agents may be used, including the use of carbodiimide cross-linkers.

Since at this point the inner core contains a solution of a polymer, a solvent and a non-solvent with different volatilities, as the more volatile solvent evaporates, or is diluted, the polymer precipitates in the presence of the less volatile non-solvent. This process forms a film of precipitate at the interface with the inner surface of the biomaterial shell, thus forming the inner shell of the microbubble after the more volatile solvent has been reduced in concentration either by dilution, evaporation or the like. The core of the microbubble then contains predominately the organic non-solvent. The microbubbles may then be isolated by centrifugation, washed, formulated in a buffer system, if desired, and dried. Typically, drying by lyophilization removes not only the non-solvent liquid core but also the residual water to yield gas-filled hollow microbubbles.

It may be desirable to further modify the surface of a bi-layer microbubble, for example, in order to passivate surfaces against macrophages or the reticuloendothelial system (RES) in the liver. This may be accomplished, for example by chemically modifying the surface of the microbubble to be negatively charged since negatively charged particles appear to better evade recognition by macrophages and the RES than positively charged particles. Also, the hydrophilicity of the surface may be changed by attaching hydrophilic conjugates, such as polyethylene glycol (PEGylation) or succinic acid (succinylation) to the surface, either alone or in conjunction with the charge modification.

Example IV

Preparation of a Controlled Fragility Polymer Contrast Microbubble

First, two solutions are prepared. One is an aqueous solution containing an appropriate surfactant material which may be an amphiphilic biopolymer such as gelatin, collagen, albumin, or globulins. Viscosity enhancers may additionally be included. This becomes the outer continuous phase of the emulsion system. The second is made from the dissolution of a wall-forming polymer in a mixture of two water immiscible organic liquids. One of the organic liquids is a relatively volatile solvent for the polymer and the other is a relatively non-volatile non-solvent for the polymer. The relatively non-volatile non-solvent is typically a C6-C20 hydrocarbon such as decane, undecane, cyclohexane, cyclooctane and the like. The relatively volatile solvent is typically a C5-C7 ester such as isopropyl acetate. Other polymer solvents, methylene chloride for example, may be used so long as they are miscible with the accompanying non-solvent. Typically about three parts of the organic polymer solution having a concentration of about 0.5 to 10 percent of the polymer is added to one part of the aqueous biomaterial solution having a concentration of about 1 to 20 percent of the biomaterial.

The wall forming polymer may be selected for its modulus of elasticity and elongation which define the mechanical properties of the polymer. Preferred polymers useful in the fabrication of drug-carrying microbubble ultrasound contrast agent would be biodegradable polymers such as polycaprolactone, polylactic acid, polylactic-polyglycolic acid copolymers, co-polymers of lactides and lactones such as epsilon-caprolactone, delta valerolactone, polyamides, polyhydroxybutryrates, polydioxanones, poly-beta-aminoketones, polyanhydrides, poly-(ortho)esters, and polyamino acids, such as polyglutamic and polyaspartic acids or esters of same. Langer et al. (1083) Macromol. Chem. Phys. C23, 61-125.

The polymer solution (inner organic phase) is added to the aqueous solution (outer phase) with agitation to form an emulsion. A variety of devices can be used to produce the emulsion, e.g. colloid mills, rotor/stator homogenizers, high pressure homogenizers, and sonicating homogenizers. The emulsification step is carried out until the inner phase droplets are in the desired size spectrum. It is this droplet size that will determine the size of the microbubble.

The emulsion thus produced may optionally be further diluted into a water bath with moderate mixing. Mixing is continued while maintaining a bath temperature appropriate for the relatively volatile solvent to evaporate while the relatively non-volatile non-solvent remains. A typical temperature is in the range of 30°-35° C. As the solvent volatilizes, polymer concentration in the droplet increases to a point where it precipitates in the presence of the less volatile non-solvent. This process forms a film of polymer at the surface of the emulsion droplet. As the process continues, an outer shell wall is formed which encapsulates an inner core of the non-solvent liquid. Once complete, the resulting microcapsules can then be retrieved, washed, and formulated in a buffer system. Subsequent drying, preferably by freeze-drying, removes both the non-solvent organic liquid core and the water to yield airfilled hollow microbubbles.

Use of an amphiphilic biopolymer as a surfactant in the outer continuous phase as described above provides for the option of creating a microbubble having a bi-layered shell. If during processing the biopolymer is rendered insoluble, by chemical crosslinking using an aldehyde, glutaraldehyde for example, the material forms a permanent contiguous outer layer enveloping and adhering to the inner polymer layer. The advantage to this construct is to allow separate tailoring of the inner and outer layers to serve different functions. While the inner layer can be modified to provide the mechanical and acoustic properties optimized to a specific drug delivery application, the outer layer can be independently altered chemically, for example to enhance biocompatibility or to increase circulation half-life. Such chemical modifications may include pegylation, succinylation, or amidation as well as attaching to the surface a targeting moiety for binding to selected tissues.

Example V

Single Wall Protein Contrast Microbubbles

Single walled protein contrast microbubble could be made as follows:

4 ml of 5% of human serum albumin in a 10 mL glass vial is sonicated using probe type ultrasound sonicator for 1-2 minutes at room temperature. After sonication, the suspension is heated up to 60 centigrade for 5-10 minutes to harden the microbubbles.

Example VI

Polymer Microparticle Fabrication by Double Emulsion

Polymer microparticles may be fabricated by double-emulsion (Water/Oil/Water) and solvent evaporation methods. Briefly, 300 mg of poly(L-lactide) (PLLA) (MW 75,000-120,000), poly(lactide-co-glycolide) (PLGA), or poly(D,L-lactide) (PDLLA) (50:50) (IV=0.38 dl/g) was dissolved in 10-25 ml dichloromethane. 2 ml water may be emulsified with polymer solution with a sonicator. This W/O emulsion may be dropped into PVA solution (200 ml, 1% w/v) and homogenized at 10,000 rpm for 1 hour. The resulting W/O/W emulsion can be continually stirred at 500-600 rpm at room temperature for another 4 hours. Finally, the resulting microparticles can be collected by centrifugation, washed five times with deionized water, and freeze-dried using a lyophilizer. The dried microbubbles can then be maintained under vacuum conditions for at least 2 hours to complete the drying process.

Example VII

Polymer Microparticle Fabrication by Emulsion/Evaporation

Briefly, 300 mg of poly(L-lactide) (PLLA) (MW 75,000-120,000), poly(lactide-co-glycolide) (PLGA), or poly(D,L-lactide) (PDLLA) (50:50) (IV=0.38 dl/g) was dissolved in 10-25 ml dichloromethane. This solution may be dropped into PVA solution (200 ml, 1% w/v) and homogenized at 10,000 rpm for 1 hour. The resulting O/W emulsion can be continually stirred at 500-600 rpm at room temperature for another 4 hours. Finally, the resulting microparticles can be collected by centrifugation, washed five times with deionized water, and freeze-dried using a lyophilizer. The dried microbubbles can then be maintained under vacuum conditions for at least 2 hours to complete the drying process.

We claim:

1. A method comprising: a) providing;
   i) a biological cell comprising an intracellular contrast double shell microbubble, wherein said double shell microbubble comprises an inner polymer layer and an outer amphiphillic biocompatible material layer;
   ii) a patient comprising an anatomical site;
   iii) an ultrasound device emitting a frequency to said intracellular contrast microbubble, wherein said microbubble oscillates; b) administering said biological cell comprising said intracellular contrast microbubble to said patient, wherein said biological cell migrates to said anatomical site and c) oscillating said intracellular contrast microbubble with said frequency under conditions such that an image of said biological cell is created.

2. The method of claim 1, wherein said intracellular contrast microbubble comprises an acoustically active gas.

3. The method of claim 2, wherein said acoustically active gas is selected from the group consisting of air, nitrogen, and a perfluorocarbon gas.

4. The method of claim 1, wherein said biological cell is a stem cell.

5. The method of claim 4, wherein said stem cell is a mesenchymal stem cell.

6. The method of claim 1, wherein said anatomical site comprises a diseased cardiovascular tissue.

7. The method of claim 1, wherein said anatomical site comprises an injured cardiovascular tissue.

* * * * *